United States Patent
Conroy-Ben

(10) Patent No.: US 11,382,328 B2
(45) Date of Patent: Jul. 12, 2022

(54) RAPID DRUG DISCOVERY METHODS FOR PATHOGEN INACTIVATION

(71) Applicant: Arizona Board of Regents on behalf of Arizona State University, Scottsdale, AZ (US)

(72) Inventor: Otakuye Conroy-Ben, Tempe, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 36 days.

(21) Appl. No.: 16/829,329

(22) Filed: Mar. 25, 2020

(65) Prior Publication Data
US 2020/0305423 A1  Oct. 1, 2020

Related U.S. Application Data

(60) Provisional application No. 62/823,126, filed on Mar. 25, 2019.

(51) Int. Cl.
| | |
|---|---|
| A01N 33/20 | (2006.01) |
| A01N 35/02 | (2006.01) |
| A01N 57/34 | (2006.01) |
| A01N 59/16 | (2006.01) |
| A01N 57/20 | (2006.01) |
| C12N 1/18 | (2006.01) |
| C12Q 1/20 | (2006.01) |
| C12Q 1/00 | (2006.01) |
| C12N 1/20 | (2006.01) |
| C12Q 1/02 | (2006.01) |

(52) U.S. Cl.
CPC ............ *A01N 33/20* (2013.01); *A01N 35/02* (2013.01); *A01N 57/20* (2013.01); *A01N 57/34* (2013.01); *A01N 59/16* (2013.01); *C12N 1/18* (2013.01); *C12Q 1/20* (2013.01); *A01N 2300/00* (2013.01); *C12N 1/20* (2013.01); *C12Q 1/00* (2013.01); *C12Q 1/025* (2013.01)

(58) Field of Classification Search
None
See application file for complete search history.

(56) References Cited

U.S. PATENT DOCUMENTS 9,034,380 B2  5/2015  Rademacher

OTHER PUBLICATIONS

Zhao, Yan, et al. "Cytotoxicity enhancement in MDA-MB-231 cells by the combination treatment of tetrahydropalmatine and berberine derived from Corydalis yanhusuo WT Wang." Journal of intercultural ethnopharmacology 3.2 (2014): 68 (Year: 2014).*

Garza-Cervantes, Javier A., et al. "Synergistic antimicrobial effects of silver/transition-metal combinatorial treatments." Scientific reports 7.1 (2017): 1-16. (Year: 2017).*
Foucquier, Julie, and Mickael Guedj. "Analysis of drug combinations: current methodological landscape." Pharmacology research & perspectives 3.3 (2015): e00149. (Year: 2015).*
Amaral L, et al. Antimicrobial activity of phenothiazines, in vivo. 2004; 18(6):725-32.
Anjaneyulu Y, et al. Preparation, characterization and antimicrobial activity studies on some ternary complexes of Cu (II) with acetylacetone and various salicylic acids. Synthesis and Reactivity in Inorganic and Metal-Organic Chemistry. 1986;16(2):257-72.
Atria A, et al. X-ray studies and antibacterial activity in copper and cobalt complexes with imidazole derivative ligands. Journal of the Chilean Chemical Society. 2011;56(3):786-92.
Babula P, et al. Voltammetric characterization of Lawsone-Copper (II) ternary complexes and their interactions with dsDNA. International Journal of Electrochemical Science. 2012;7(8):7349-66.
Bachmann BJ. Derivations and genotypes of some mutant derivatives of *Escherichia coli* K-12. *Escherichia coli* and Salmonella: cellular and molecular biology, 2nd ed ASM Press, Washington, DC. 1996:2460-88.
Beeton ML, et al. The antimicrobial and antibiofilm activities of copper (II) complexes. Journal of inorganic biochemistry. 2014;140:167-72.
Birla S, et al. Fabrication of silver nanoparticles by Phoma glomerata and its combined effect against *Escherichia coli*. Pseudomonas aeruginosa and *Staphylococcus aureus*. Letters in Applied Microbiology. 2009;48(2):173-9.
Burygin G, et al. On the enhanced antibacterial activity of antibiotics mixed with gold nanoparticles. Nanoscale research letters. 2009;4(8):794.
Cervello M, et al. Novel combination of sorafenib and celecoxib provides synergistic anti-proliferative and pro-apoptotic effects in human liver cancer cells. PloS one. 2013;8(6):e65569.
Chen C-A, et al. In vivo cleavage of a target RNA by copper kanamycin A. Direct observation by a fluorescence assay. Chemical Communications. 2002(3):196-7.
Chou T-C. Theoretical basis, experimental design, and computerized simulation of synergism and antagonism in drug combination studies. Pharmacological reviews. 2006;58(3):621-81.
Conroy O, et al. Differing ability to transport nonmetal substrates by two RND-type metal exporters. FEMS microbiology letters. 2010;308(2):115-22.
Creaven BS, et al. Synthesis and antimicrobial activity of copper (II) and silver (I) complexes of hydroxynitrocoumarins: X-ray crystal structures of [Cu (hnc) 2 (H 2 O) 2]? 2H 2 O and [Ag (hnc)](hncH= 4-hydroxy-3-nitro-2H-chromen-2-one). Polyhedron. 2005;24(8):949-57.
Deng H, et al. Mechanistic study of the synergistic antibacterial activity of combined silver nanoparticles and common antibiotics. Environmental science & technology. 2016;50(16):8840-8.

(Continued)

*Primary Examiner* — Robert J Yamasaki
(74) *Attorney, Agent, or Firm* — Quarles & Brady LLP

(57) ABSTRACT

Provided herein are rapid, large-scale screening methods for identifying metal-biocide combinations that are synergistically effective to kill or inhibit the growth of microorganisms. Also provided herein are novel, synergistically antimicrobial metal-biocide combinations and uses of such compositions to curb or slow microbial growth.

5 Claims, 8 Drawing Sheets
(8 of 8 Drawing Sheet(s) Filed in Color)

(56) References Cited

OTHER PUBLICATIONS

Dhas SP, et al. Synergistic effect of biogenic silver nanocolloid in combination with antibiotics: a potent therapeutic agent. International Journal of Pharmacy and Pharmaceutical Sciences. 2013;5(1):292-5.
Dinger MB, et al. Organogold (III) metallacyclic chemistry. Part 4. Synthesis, characterisation, and biological activity of gold (lll)-thiosalicylate and-salicylate complexes. Journal of organometallic chemistry. 1998;560(1):233-43.
Efthimiadou EK, et al. Structure and biological properties of the copper (II) complex with the quinolone antibacterial drug N-propyl-norfloxacin and 2, 2'-bipyridine. Journal of inorganic biochemistry. 2007;101(1):64-73.
Escamilla-García E, et al. Antimicrobial Activity of a Cationic Guanidine Compound against Two Pathogenic Oral Bacteria. International journal of microbiology. 2017;2017.
Fay F, et al. SEM and EDX analysis: two powerful techniques for the study of antifouling paints. Progress in Organic Coatings. 2005;54(3):216-23.
Fayaz AM, et al. Biogenic synthesis of silver nanoparticles and their synergistic effect with antibiotics: a study against gram-positive and gram-negative bacteria. Nanomedicine: Nanotechnology, Biology and Medicine. 2010;6(1):103-9.
Fernández-González A, et al. Insights into the reaction of ß-lactam antibiotics with copper (II) ions in aqueous and micellar media: Kinetic and spectrometric studies. Analytical biochemistry. 2005;341(1):113-21.
Fox CL, et al. Mechanism of silver sulfadiazine action on burn wound infections. Antimicrobial agents and chemotherapy. 1974;5(6):582-8.
Fox CL. Silver sulfadiazine—a new topical therapy for pseudomonas in burns: therapy of pseudomonas infection in burns. Archives of surgery. 1968;96(2):184-8.
Ghosh M, et al. In vitro and in vivo genotoxicity of silver nanoparticles. Mutation Research/Genetic Toxicology and Environmental Mutagenesis. 2012;749(1):60-9.
Goh CH, et al. Interactions of antimicrobial compounds with cross-linking agents of alginate dressings. Journal of antimicrobial chemotherapy. 2008;62(1):105-8.
Gorbunova M, et al. New biocide guanidine-containing nanocomposites. Journal of nanoparticle research. 2014;16(8):2566.
Grace AN, et al. Antibacterial efficacy of aminoglycosidic antibiotics protected gold nanoparticles—A brief study. Colloids and Surfaces A: Physicochemical and Engineering Aspects. 2007;297(1):63-70.
Gu H, et al. Presenting vancomycin on nanoparticles to enhance antimicrobial activities. Nano letters. 2003;3(9):1261-3.
Gurunathan S. Biologically synthesized silver nanoparticles enhances antibiotic activity against Gram-negative bacteria. Journal of Industrial and Engineering Chemistry. 2015;29:217-26.
Hancock RE. Resistance mechanisms in Pseudomonas aeruginosa and other nonfermentative gram-negative bacteria. Clinical Infectious Diseases. 1998;27(Supplement_1):S93-S9.
Herisse M, et al. Silver potentiates aminoglycoside toxicity by enhancing their uptake. Molecular microbiology. 2017;105(1):115-26.
Hwang I-s, et al. Synergistic effects between silver nanoparticles and antibiotics and the mechanisms involved. Journal of medical microbiology. 2012;61(12):1719-26.
Iroha IR et al. Antibacterial efficacy of colloidal silver alone and in combination with other antibiotics on isolates from wound Infections. Scientific Research and Essays. 2007;2(8):338-41.
Jezowska-Bojczuk M, et al. Metal ion-tetracycline interactions in biological fluids. 10. Structural investigations on copper (II) complexes of tetracycline, oxytetracycline, chlortetracycline, 4-(dedimethylamino) tetracycline, and 6-desoxy-6-demethyltetracycline and discussion of their binding modes. Inorganic Chemistry. 1993;32(4):428-37.
Kaatz GW, et al. Phenothiazines and thioxanthenes inhibit multidrug efflux pump activity in *Staphylococcus aureus*. Antimicrobial agents and chemotherapy. 2003;47(2):719-26.
Kalinowska-Lis U, et al. Synthesis, characterization and antimicrobial activity of water-soluble silver (I) complexes of metronidazole drug and selected counter-ions. Dalton Transactions. 2015;44(17):8178-89.
Kashyap DR, et al. Peptidoglycan recognition proteins kill bacteria by inducing oxidative, thiol, and metal stress. PLoS pathogens. 2014;10(7):e1004280.
Kumar V, et al. Designing, syntheses, characterization, computational study and biological activities of silver-phenothiazine metal complex. Journal of Molecular Structure. 2015;1099:135-41.
Li W-R, et al. Antibacterial activity and mechanism of silver nanoparticles on *Escherichia coli*. Applied microbiology and biotechnology. 2010;85(4):1115-22.
Li X-Z, et al. Silver-resistant mutants of *Escherichia coli* display active efflux of Ag+ and are deficient in porins. Journal of bacteriology. 1997;179(19):6127-32.
Marques LL, et al. New gold (I) and silver (I) complexes of sulfamethoxazole: Synthesis, X-ray structural characterization and microbiological activities of triphenylphosphine (sulfamethoxazolato-N2) gold (I) and sulfamethoxazolato) silver (I). Inorganic Chemistry Communications. 2007;10(9):1083-7.
Martins, M, et al. Enhanced killing of intracellular pathogenic bacteria by phenothiazines and the role of K+ efflux pumps of the bacterium and the killing macrophage. Anti-Infective Agents in Medicinal Chemistry 2008;7(1):63-72.
Melnik M, et al. Copper (II) carboxylates and their antimicrobial effect. Inorganica Chimica Acta. 1982;67:117-20.
Mijnendonckx K, et al. Antimicrobial silver: uses, toxicity and potential for resistance. Biometals. 2013;26(4):609-21.
Mo S, et al. An antimicrobial guanidine-bearing sesterterpene from the cultured Cyanobacterium scytonema sp. Journal of natural products. 2009;72(11):2043-5.
Molnar J, et al. Antiplasmid activity: loss of bacterial resistance to antibiotics. APMIS Supplementum. 1992;30:24-31.
Molnar J, et al. Inhibition of the transport function of membrane proteins by some substituted phenothiazines in *E. coli* and multidrug resistant tumor cells. Anticancer research. 1997;17(1A):481-6.
Molnar J, et al. Synergism between Antiplasmid Promethazine and Antibiotics. Vitro; 2014.
Morioka H, et al. Polymyxin B binding sites in *Escherichia coli* as revealed by polymyxin B-gold labeling. Journal of Histochemistry & Cytochemistry. 1987;35(2):229-31.
Morones-Ramirez JR, et al. Silver enhances antibiotic activity against gram-negative bacteria. Science translational medicine. 2013;5(190):190ra81-ra81.
Naqvi SZH, et al. Combined efficacy of biologically synthesized silver nanoparticles and different antibiotics against multidrug-resistant bacteria. International journal of nanomedicine. 2013;8:3187.
Nazeem S, et al. Plumbagin induces cell death through a copper-redox cycle mechanism in human cancer cells. Mutagenesis. 2009;24(5):413-8.
Nunes JHB, et al. Silver complexes with sulfathiazole and sulfamethoxazole: Synthesis, spectroscopic characterization, crystal structure and antibacterial assays. Polyhedron. 2015;85:437-44.
Padhye S, et al. Perspectives on medicinal properties of plumbagin and its analogs. Medicinal research reviews. 2012;32(6):1131-58.
Panacek A, et al. Strong and nonspecific synergistic antibacterial efficiency of antibiotics combined with silver nanoparticles at very low concentrations showing no cytotoxic effect. Molecules. 2015;21(1):26.
Perontsis S, et al. Characterization and biological properties of copper (II)-ketoprofen complexes. Journal of inorganic biochemistry. 2016;162:22-30.
Prasad M, et al. Synthesis, Spectral, Cyclic Voltammetric and Antimicrobial Studies of Copper (II) Complexes with Tetradentate Bis-Benzomidazole Based Diamide Ligand. International Journal of Chemical Sciences. 2012;10(1).
Quinlan GJ, et al. DNA base damage by ß-lactam, tetracycline, bacitracin and rifamycin antibacterial antibiotics. Biochemical pharmacology. 1991;42(8):1595-9.

(56) References Cited

OTHER PUBLICATIONS

Quinlan GJ, et al. Oxidative damage to DNA and deoxyribose by ß-lactam antibiotics in the presence of iron and copper salts. Free radical research communications. 1988;5(3):149-58.
Rai M, et al. Silver nanoparticles as a new generation of antimicrobials. Biotechnology advances. 2009;27(1):76-83.
Randall CP, et al. Silver resistance in Gram-negative bacteria: a dissection of endogenous and exogenous mechanisms. Journal of Antimicrobial Chemotherapy. 2015;70(4):1037-46.
Rane S, et al. Effect of ligand conformation on the reactivity of copper (II) complexes of lawsone and its derivatives. Synthesis and Reactivity in Inorganic and Metal-Organic Chemistry. 1988;18(6):609-27.
Rensing C, et al. *Escherichia coli* mechanisms of copper homeostasis in a changing environment. FEMS microbiology reviews. 2003;27(2-3):197-213.
Richards RME, et al. An evaluation of the antibacterial activities of combinations of sulfonamides, trimethoprim, dibromopropamidine, and silver nitrate compared with their uptakes by selected bacteria. Journal of pharmaceutical sciences. 1991;80(9):861-7.
Rodrigues L, et al. Inhibition of drug efflux in mycobacteria with phenothiazines and other putative efflux inhibitors. Recent patents on anti-infective drug discovery. 2011;6(2):118-27.
Rodriguez-Arguelles MC, et al. Copper complexes of imidazole-2-, pyrrole-2-and indol-3-carbaldehyde thiosemicarbazones: inhibitory activity against fungi and bacteria. Journal of inorganic biochemistry. 2005;99(11):2231-9.
Roshmi T, et al. Effect of biofabricated gold nanoparticle-based antibiotic conjugates on minimum inhibitory concentration of bacterial isolates of clinical origin. Gold Bulletin. 2015;48(1-2):63-71.
Rowan R, et al. 'Silver bullets' in antimicrobial chemotherapy: Synthesis, characterisation and biological screening of some new Ag (I)-containing imidazole complexes. Polyhedron. 2006;25(8):1771-8.
Ruden S, et al. Synergistic interaction between silver nanoparticles and membrane-permeabilizing antimicrobial peptides. Antimicrobial agents and chemotherapy. 2009;53(8):3538-40.
Saenz Y, et al. Mechanisms of resistance in multiple-antibiotic-resistant *Escherichia coli* strains of human, animal, and food origins. Antimicrobial agents and chemotherapy. 2004;48(10):3996-4001.
Saha DK, et al. Antimycobacterial activity of mixed-ligand copper quinolone complexes. Transition metal chemistry. 2003;28(5):579-84.
Said M, et al. Synthesis, structural characterization and antibacterial studies of trisubstituted guanidines and their copper (II) complexes. Inorganica Chimica Acta. 2015;434:7-13.
Santo CE, et al. Contribution of copper ion resistance to survival of *Escherichia coli* on metallic copper surfaces. Applied and environmental microbiology. 2008;74(4):977-86.
Shahverdi AR, et al. Synthesis and effect of silver nanoparticles on the antibacterial activity of different antibiotics against *Staphylococcus aureus* and *Escherichia coli*. Nanomedicine: Nanotechnology, Biology and Medicine. 2007;3(2):168-71.
Singh P, et al. Biosynthesis of anisotropic silver nanoparticles by Bhargavaea indica and their synergistic effect with antibiotics against pathogenic microorganisms. Journal of Nanomaterials. 2015;2015:4.
Smit H, et al. Mode of action of copper complexes of some 2, 2'-bipyridyl analogs on Paracoccus denitrificans. Antimicrobial agents and chemotherapy. 1980;18(2):249-56.
Strydom SJ, et al. Poly (amidoamine) dendrimer-mediated synthesis and stabilization of silver sulfonamide nanoparticles with increased antibacterial activity. Nanomedicine: nanotechnology, biology and medicine. 2013;9(1):85-93.
Szczepanik W, et al. Oxidative activity of copper (II) complexes with aminoglycoside antibiotics as implication to the toxicity of these drugs. Bioinorganic chemistry and applications. 2004;2(1-2):55-68.
Tabrizi L, et al. Nickel (II) and cobalt (II) complexes of lidocaine: Synthesis, structure and comparative in vitro evaluations of biological perspectives. European journal of medicinal chemistry. 2015;103:516-29.
Tom RT, et al. Ciprofloxacin-protected gold nanoparticles. Langmuir. 2004;20(5):1909-14.
Veal JM, et al. Noncovalent DNA binding of bis (1, 10-phenanthroline) copper (I) and related compounds. Biochemistry. 1991;30(4):1132-40.
Vidal MT, et al. Inhibitory effect of copper and dichlofluanid on Oenococcus oeni and malolactic fermentation. American Journal of Enology and Viticulture. 2001;52(3):223-9.
Wang Y-W, et al. Enhanced bactericidal toxicity of silver nanoparticles by the antibiotic gentamicin. Environmental Science: Nano. 2016;3(4):788-98.
Wu G, et al. Synthesis, crystal structure, stacking effect and antibacterial studies of a novel quatemary copper (II) complex with quinolone. Molecules. 2003;8(2):287-96.
Zhao Y, et al. Cytotoxicity enhancement in MDA-MB-231 cells by the combination treatment of tetrahydropalmatine and berberine derived from Corydalis yanhusuo WT Wang. Journal of intercultural ethnopharmacology. 2014;3(2):68.
Zhao Y, et al. Synergy of non-antibiotic drugs and pyrimidinethiol on gold nanoparticles against superbugs. Journal of the American Chemical Society. 2013;135(35):12940-3.
Zivec P, et al. Different types of copper complexes with the quinolone antimicrobial drugs ofloxacin and norfloxacin: Structure, DNA-and albumin-binding. Journal of inorganic biochemistry. 2012;117:35-47.
Lesniak W, et al. Solution Chemistry of Copper (II)—Gentamicin Complexes: Relevance to Metal-Related Aminoglycoside Toxicity. Inorganic chemistry. 2003;42(5):1420-9.

\* cited by examiner

RAPID DRUG DISCOVERY METHODS FOR PATHOGEN INACTIVATION

CROSS-REFERENCE TO RELATED APPLICATIONS

This application claims the benefit of U.S. Provisional Application No. 62/823,126, filed Mar. 25, 2019, which is incorporated herein by reference in its entirety.

STATEMENT REGARDING FEDERALLY SPONSORED RESEARCH

Not applicable.

BACKGROUND

The World Health Organization has listed antimicrobial resistance as one of the top threats facing health today. The over-prescription of antibiotics, use of biocides in commercial products, and misuse of antimicrobials has led to microbes surviving drug application. Consequently, stronger pharmaceuticals are often necessary to fight infections. Accordingly, there remains a need in the art for rapid drug discovery methods to identify drug combinations that inactivate bacteria. Moreover, there is a need for additional combinations of antimicrobial compounds having enhanced activity to provide effective control of the microorganisms. The problems addressed by this disclosure include providing such additional combinations of antimicrobial compounds.

SUMMARY

In a first aspect, provided herein is an antimicrobial composition comprising: (a) a biocide; and (b) a Group IB metal; wherein the composition has a coefficient of drug interaction (CDI) less than or equal to 0.5. The metal can be gold and the biocide can be disulfiram, thiosalisylic acid, novobiocin, chlorpromazine, or a biocide selected from the group consisting of a glycopeptide, a macrolide, and a sodium channel inhibitor. The glycopeptide can be selected from bleomycin and vancomycin. The macrolide can be selected from the group consisting of erythromycin, josamycin, oleandomycin, spiramycin, troleandomycin, and tylosin. The sodium channel inhibitor can be lidocaine or procaine. The metal can be silver and the biocide can be selected from the group consisting of 5,7-dichloro-8-hydroxyquinaldine, 5,7-dichloro-8-hydroxyquinoline, 5-chloro-7-iodo-8-hydroxyquinoline, 8-hydroxyquinoline, 9-aminoacridine, acriflavine, novobiocin, proflavine, nordihydroguaiaretic acid, dichlofluanid, tolylfluanid, lidocaine, procaine, D,L-serine hydroxamate, D,L-methionine hydroxamate, L-glutamic-γ-hydroxamate, erythromycin, josamycin, oleandomycin, troleandomycin, tylosin, benserazide, chlorpromazine, promethazine, thioridazine, trifluoperazine, dodine, guanidine hydrochloride, atropine, orphenadrine, 2-nitroimidazole, ornidazole, methyl viologen, D,L-propanolol, patulin, sanguinarine, and iodoacetate. The metal can be copper and the biocide can be selected from the group consisting of chlorodinitrobenzene, methyl viologen, thioctic acid, iodonitrotetrazolium violet, fusidic acid, nordihydroguaiaretic acid, a nitrofuran, a triazole, a fenicol, lauryl sulfobetaine, niaproof, menadione, and lidocaine.

In another aspect, provided herein is a method of killing a microorganism or inhibiting its growth by the application of an effective amount of an antimicrobial composition as provided herein. The microorganism can be a bacterium.

In another aspect, provided herein is a method for inhibiting microbiological growth on, or in, a medium which comprises coating the medium with an antimicrobial composition as provided herein. The medium can be a medical device. Coating the medium with the antimicrobial composition can inhibit growth of one or more types of microorganisms.

In a further aspect, provided herein is a method of screening for synergistically effective metal-biocide combinations. The method can comprise or consist essentially of contacting microorganisms to test biocides deposited on a solid surface, wherein the microorganisms are in a culture medium comprising a soluble Group IB metal; culturing the contacted microorganisms in the culture medium for a predetermined length of time; and screening for synergistically effective combinations of a test biocide and the metal, wherein screening comprises measuring relative growth and determining a coefficient of drug interaction (CDI) for each metal-biocide combination, wherein a combination is synergistically effective against the microorganisms if CDI<0.5. The soluble Group IB metal can be silver, gold, or copper. The microorganisms can be bacteria. The contacted microorganisms can be cultured in the culture medium for about 12 to about 24 hours. The contacted microorganisms can be cultured in the culture medium for about 16 hours. The test biocides can comprise radioactive isotopes, toxic metal ions, nanomaterials, or plasmid curing agents.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
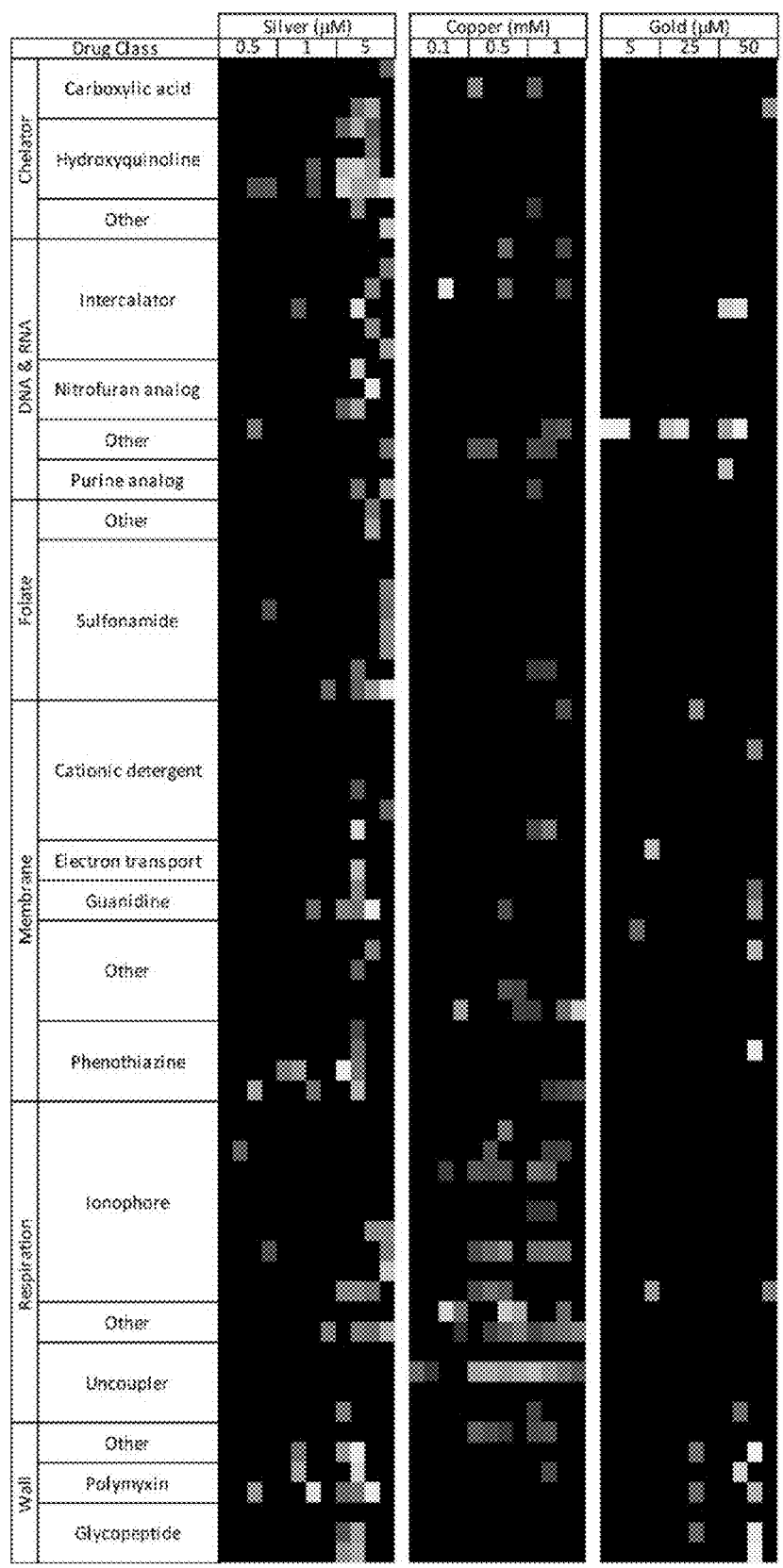
FIG. 1 presents drug-metal combinations that resulted in synergistic coefficient of drug interaction (CDI) values.
Figure 1:
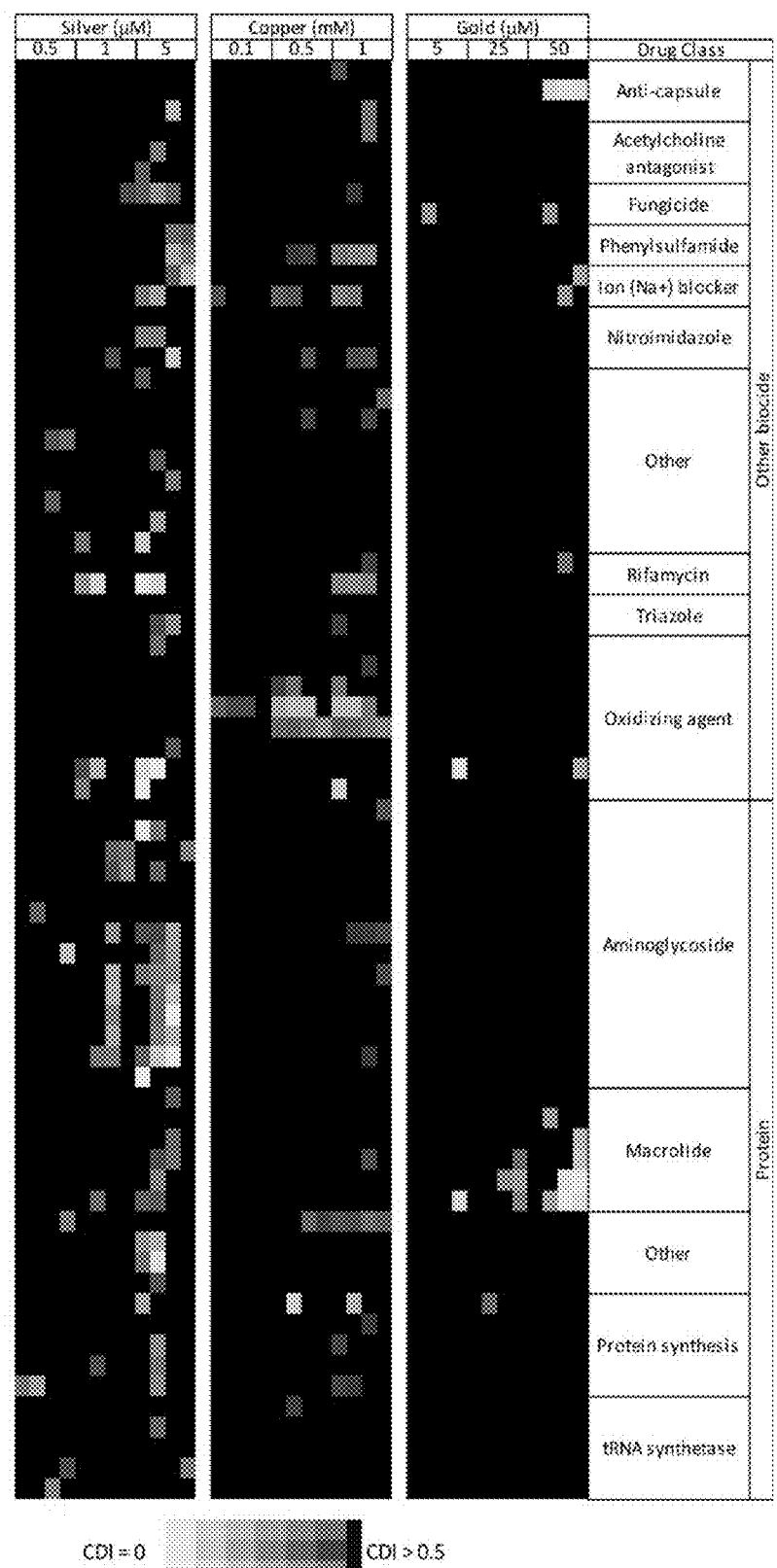
Figure 2:
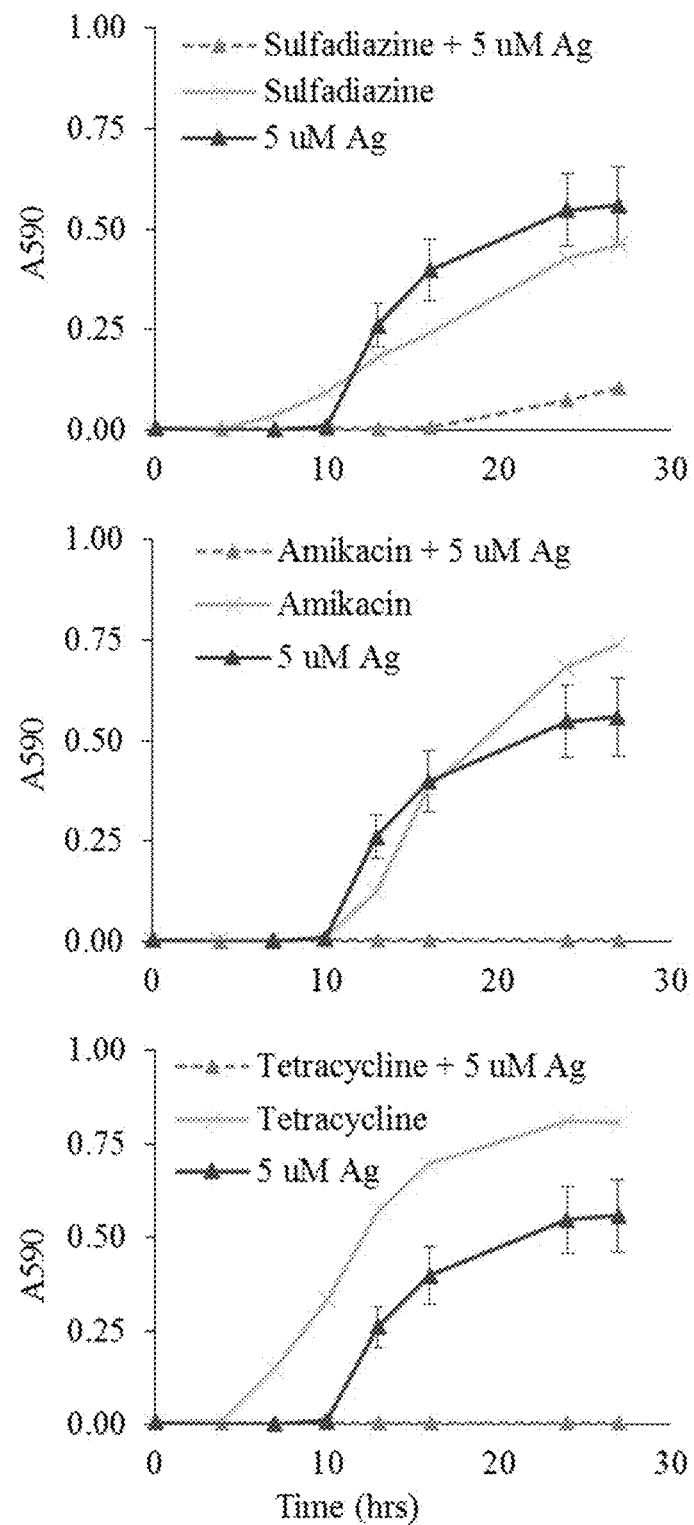
FIG. 2 demonstrates enhanced cell toxicity when grown on sulfonamide (sulfadiazine), amikacin (an aminoglycoside), and tetracycline with and without silver.
Figure 3:
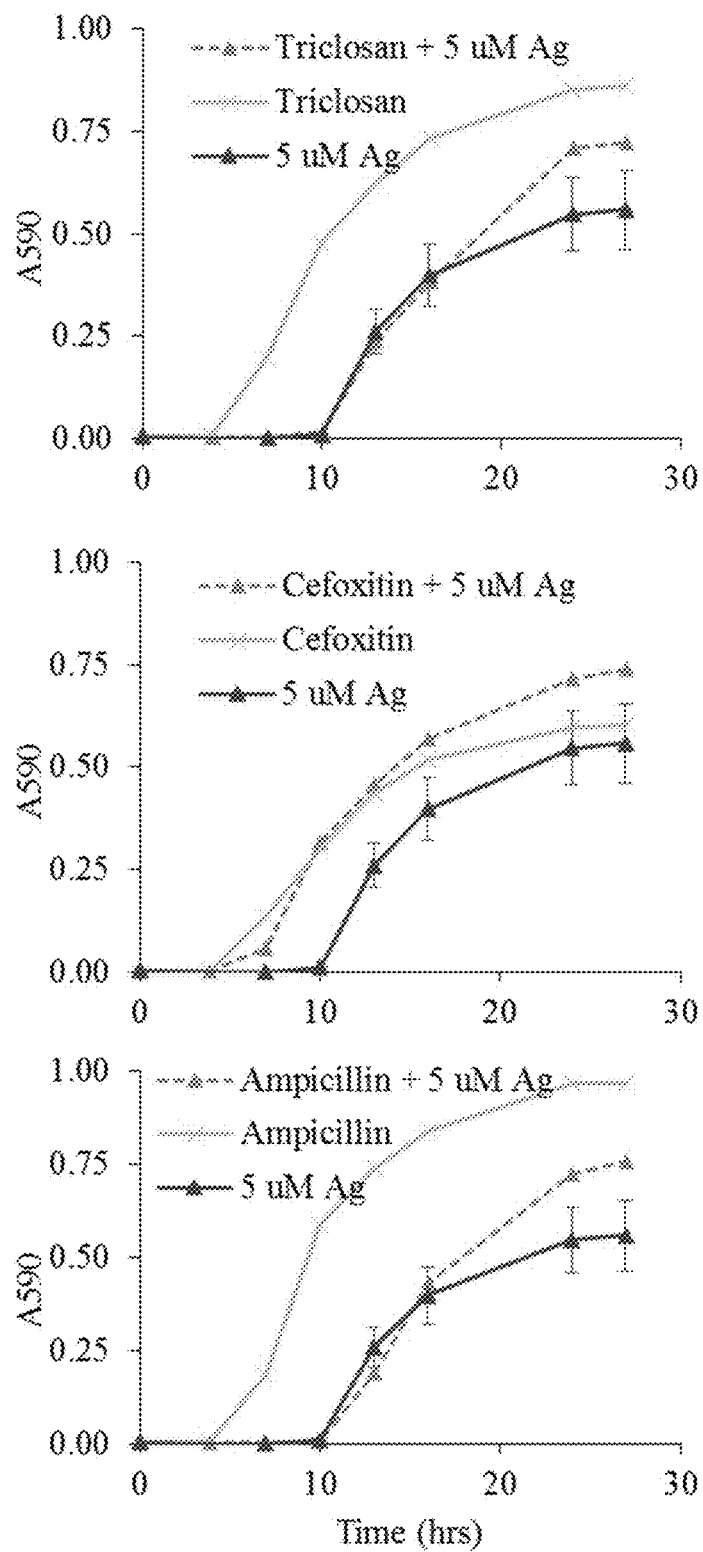
FIG. 3 presents growth curves demonstrating that certain antibiotic classes did not exhibit synergy when combined with, and instead are similar to, silver or the antibiotic alone.
Figure 4:
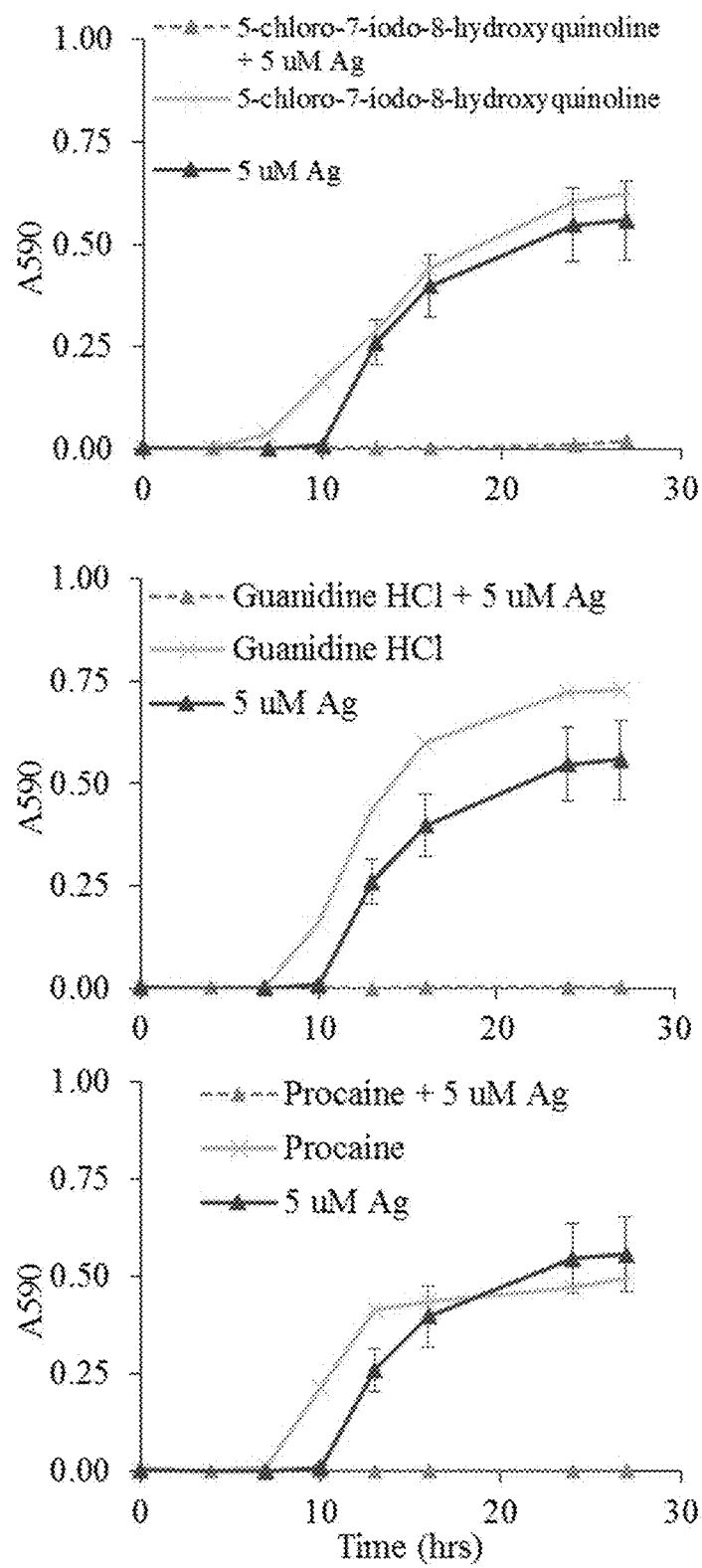
FIG. 4 presents 24-hour growth curves demonstrating growth inhibition of certain silver-biocide combinations.
Figure 5:
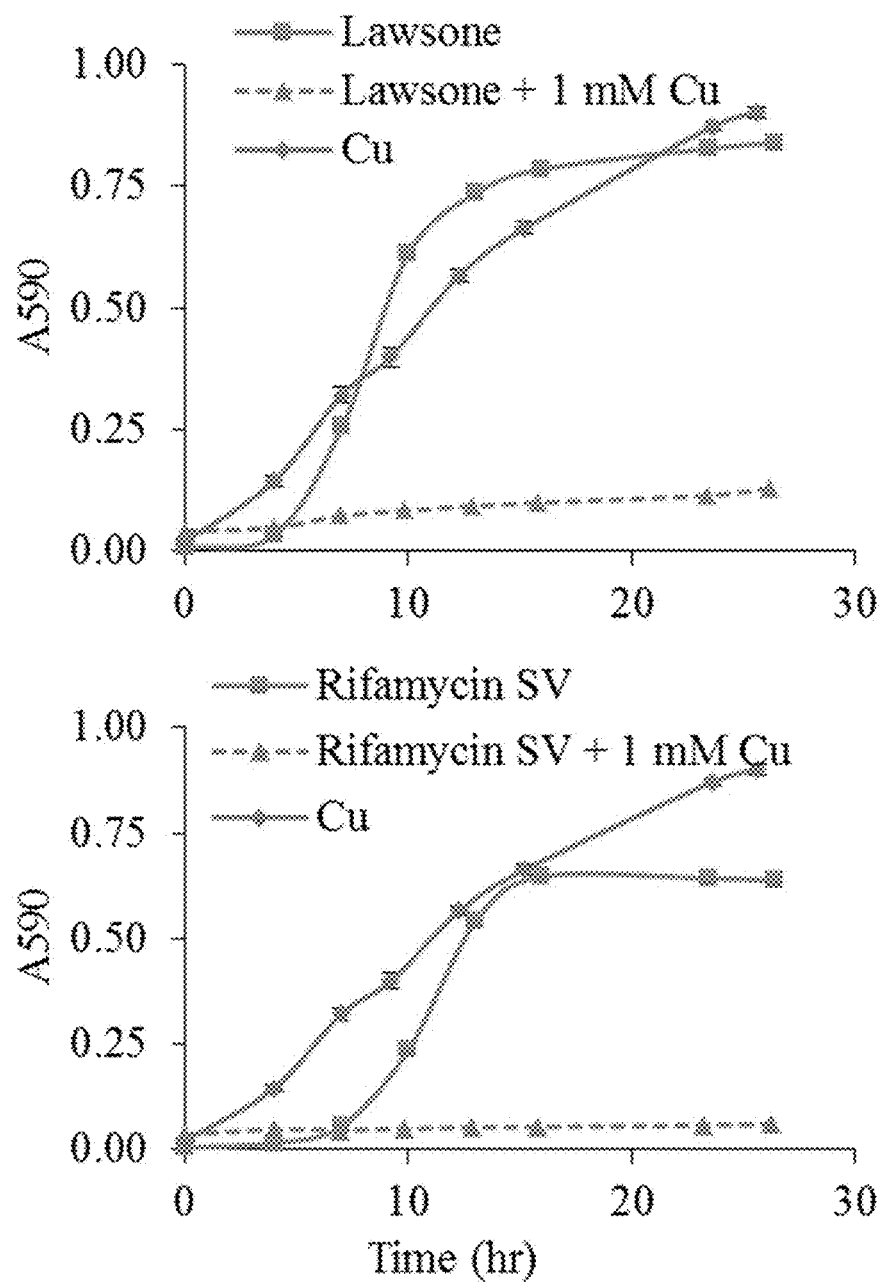
FIG. 5 presents copper-biocide interactions that resulted in synergistic CDI values.
Figure 6:
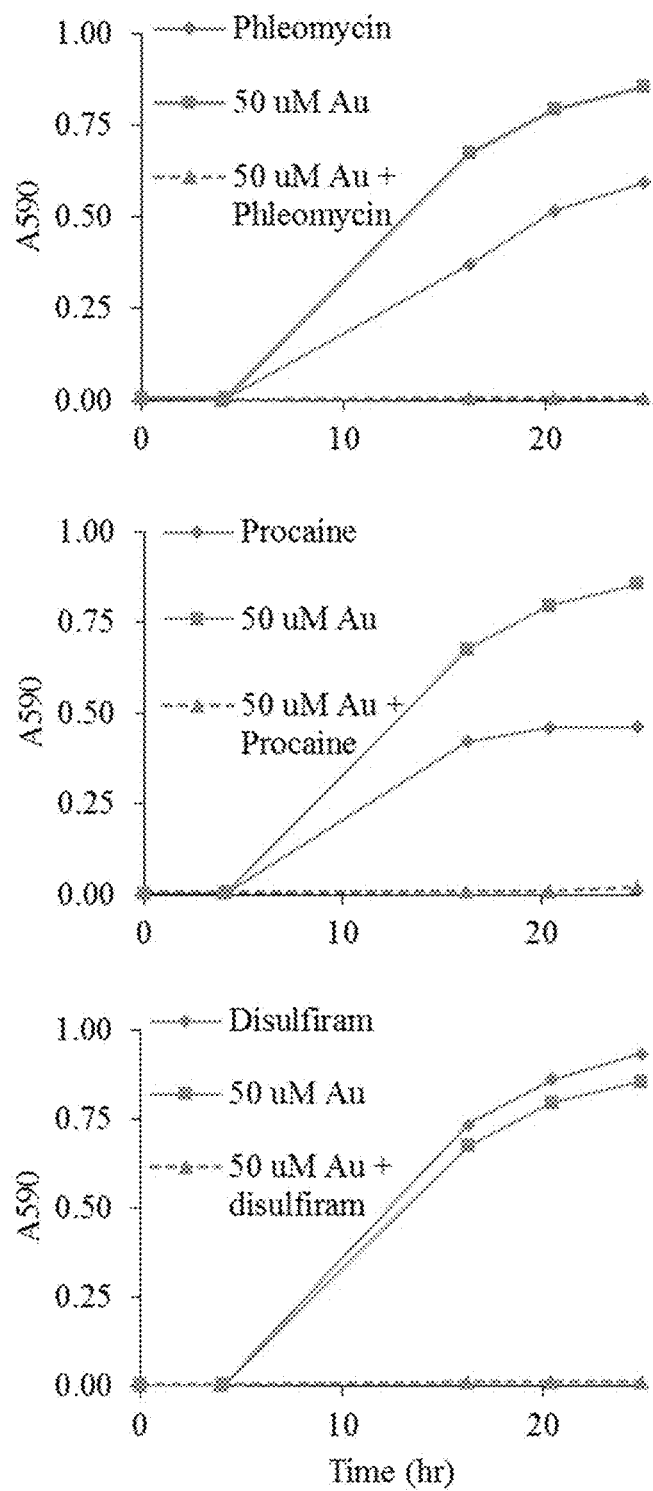
FIG. 6 demonstrates synergistic toxic interactions between gold and phenothiazines, glycopeptides, macrolides, and polymyxins.

All publications, including but not limited to patents and patent applications, cited in this specification are herein incorporated by reference as though set forth in their entirety in the present application.

The methods and compositions provided herein are based at least in part on the inventors' development of a rapid, large-scale screening method for identifying metal-biocide combinations that are synergistically effective to kill and/or inhibit the growth of microorganisms.

Compositions

Accordingly, in a first aspect, provided herein are antimicrobial compositions comprising (a) an antimicrobial agent; and (b) a Group IB metal, the composition having a coefficient of drug interaction (CDI) less than 0.5 (CDI<0.5). The synergistic antimicrobial compositions presented herein have not been previously described. CDI is used to evaluate whether responses to drug combinations are additive, synergistic, or antagonistic. Using Equation 1, combinations are considered to be additive if CDI about 1, synergistic if CDI is less than (<) 1, and antagonistic if CDI is greater than (>) 1. A CDI of less than 0.5 is considered to have significantly synergistic effects on bacterial growth as demonstrated in the Examples. A metal-biocide combination is considered to be strongly synergistic against a microorganism if CDI<0.1. Relative growth, meaning growth normalized to that in LB media or chloride-free LB, was calculated for cultures grown in the antibiotic (A) alone, the metal ion alone (B), or the metal-antibiotic mixture (A+B).

$$CDI = \frac{A+B}{A \times B} \quad \text{(Equation 1)}$$

Agents that inhibit the growth of a microorganism or culture of microorganisms can be any agent that reduces growth, inhibits reproduction, and/or causes death upon contact or exposure to the microorganism or culture of microorganisms. As used herein, the terms "antimicrobial," "microbicidal," or "biocidal" refer to the ability to kill at least some types of microorganisms, or to inhibit the growth or reproduction of at least some types of microorganisms. The terms "antimicrobial agent" or "biocide" refer to any compound or substance that kills, inhibits, or slows the growth or propagation of at least some types of microorganisms which include, for example, bacteria, fungi (such as yeasts and mold), mycoplasma, viruses, parasites, and algae. Antimicrobial agents include, without limitation, bactericides, bacteristats, fungicides, fungistats, algaecides and algistats, depending on the dose level applied, system conditions, and the level of microbial control desired.

As used herein, the term "group IB metal" refers to elements of group IB (also referred to as Group 11) of the Periodic Table of Elements. Exemplary group IB metals are copper, silver, and gold, also known as "coinage metals." Group IB metals include metal oxides and metal salts. In some embodiments, the group IB metal is $AgNO_3$, $CuSO_4$, or $HAuCl_4$.

In some embodiments, the metal is gold and the biocide is selected from the group consisting of a glycopeptide, a macrolide, and a sodium channel inhibitor. Exemplary glycopeptides that act synergistically with gold include bleomycin, and vancomycin.

In some embodiments, the metal is silver and the biocide is selected from 5,7-dichloro-8-hydroxyquinaldine, 5,7-dichloro-8-hydroxyquinoline, 5-chloro-7-iodo-8-hydroxyquinoline, 8-hydroxyquinoline, 9-aminoacridine, acriflavine, novobiocin, proflavine, nordihydroguaiaretic acid, dichlofluanid, tolylfluanid, lidocaine, procaine, D,L-serine hydroxamate, D,L-methionine hydroxamate, L-glutamic-γ-hydroxamate, erythromycin, josamycin, oleandomycin, troleandomycin, tylosin, benserazide, chlorpromazine, promethazine, thioridazine, trifluoperazine, dodine, guanidine hydrochloride, atropine, orphenadrine, 2-nitroimidazole, ornidazole, methyl viologen, and iodoacetate.

In some embodiments, the metal is silver and the biocide is selected from doxycycline, rolitetracycline, penimepicycline, and tetracycline.

In some embodiments, the metal is copper and the biocide is selected from the group consisting of chlorodinitrobenzene, methyl viologen, thioctic acid, iodonitrotetrazolium violet, fusidic acid, nordihydroguaiaretic acid, a nitrofuran analog, a triazole, a phenicol, lauryl sulfobetaine, niaproof, menadione, and lidocaine. Exemplary nitrofuran analogs include, without limitation, 5-Nitro-2-furaldehyde semicarbazone, furaltadone, and nitrofurantoin. Exemplary triazoles include, without limitation, guanazole and 3-amino-1,2,4-triazole. Exemplary phenicols include, without limitation, chloramphenicol and thiamphenicol.

Screening Methods

In another aspect, provided herein is a method of screening for synergistically effective metal-biocide combinations. As demonstrated in this disclosure, the method can be used to screen a large number of test agents in a short amount of time with reproducible results. In some cases, the method comprises contacting microorganisms to test biocides deposited on a surface (e.g., a solid surface), where the microorganisms are provided in a culture medium comprising a soluble Group IB metal. As described herein, the soluble Group IB metal is preferably silver, gold, or copper. In some cases, the soluble metal is silver nitrate, copper sulfate, and gold chloride.

In a next step, the method comprises culturing the contacted microorganisms in the culture medium for a predetermined length of time; and then screening the cultures for synergistically effective combinations of a test agent (e.g., candidate biocide) and the metal. In some cases, screening comprises measuring relative growth of the microorganism culture and determining a CDI for each metal-biocide combination, where a combination is synergistically effective against the microorganisms if CDI<0.5. A metal-biocide combination is considered to be strongly synergistic against a microorganism if CDI<0.1.

In some cases, the contacted microorganisms are cultured in the culture medium for about 12 to about 24 hours, and preferably 16 hours. As described in the Examples, absorbance after about 16 hours in culture can be measured and used to compare the growth of the bacteria in the presence of metal alone, biocide alone, and metal-biocide combinations. Relative growth can be converted to the combination drug index as described herein.

As used herein, the term "surface" refers to a material upon which a sample or specimen (e.g., a sample of microorganism) can be placed for the methods described herein. Surfaces may in principle be of any type. In some cases, the surface is a solid material or substantially solid (e.g., porous) material. Exemplary surfaces include, without limitation, a petri dish, a multiwell plate, a microscope slide, a microtiter plate, a cartridge, a test tube, a probe, a membrane, a film, and a filter.

Any microorganism that can be grown in liquid culture can be used for the screening methods. In some cases, the microorganisms comprise one or more species of bacteria, virus, fungus, mycoplasma, or parasite. Bacteria include, without limitation, clinically relevant species such as *E. coli, M. tuberculosis, Salmonella, Streptococci, Staphylococci, Enterobacteriaceae*, Carbapenem-resistant *Enterobacteriaceae* (CRE), *Pseudomonas aeruginosa, Stenotrophomonas maltophilia, Burkholderia cepacia, Alcaligenes xylosoxidans, Acinetobacter, Haemophilus, Neisseria species, Francisella tularensis, Yersinia pestis, Burkholderia pseudomallei, Burkholderia mallei, Rickettsia prowazekii, Coxiella burnetti, Campylobacter jejuni, Shigella, Moraxella catarrhalis*, and *Chlamydia trachomatis*. Other microorganisms for use according to the screening methods include clinically relevant species of fungi (e.g., *Candida* species, *Aspergillus* species), viruses, mycoplasma, and parasites (e.g., protozoan and metazoan pathogens such as *Plasmodia* species, *Leishmania* species, *Schistosoma* species, *Trypanosoma* species).

In some cases, the test biocides include, without limitation, radioactive isotopes, metal ions (e.g., iron (Fe)), nanomaterials, or plasmid curing agents.

Methods of Use

According to another aspect, provided herein are methods of killing a microorganism or inhibiting its growth by the application of an effective amount of a synergistic antimicrobial composition. As used herein, the term "effective amount" refer to the quantity of active therapeutic agent sufficient to yield a desired response without undue adverse side effects such as toxicity, irritation, or allergic response. The specific "effective amount" will, obviously, vary with such factors as the particular microorganism, the duration of the treatment, and the specific formulations employed and the structure of the compounds or its derivatives. The optimum effective amounts can be readily determined by one of ordinary skill in the art using routine experimentation.

In another aspect, provided herein is a method for inhibiting microbiological growth on or in an object or medium where the method comprises coating the object or medium with an effective amount of a synergistic antimicrobial composition. In some cases, compositions of this disclosure are used as antimicrobial surface coatings for objects including, without limitation, healthcare-associated products, medical devices and components, medical electronics, products used in dental and veterinary fields, products used in food preparation or food storage, consumable products, products for cell culture (e.g., growth media), and other products for which the prevention of bacterial and/or fungal growth and spread is important.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior invention.

As used herein and in the appended claims, the singular forms "a," "an," and "the" include plural reference, unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

In the specification and in the claims, the terms "including" and "comprising" are open-ended terms and should be interpreted to mean "including, but not limited to." These terms encompass the more restrictive terms "consisting essentially of" and "consisting of."

As used herein, the terms "approximately" or "about" in reference to a number are generally taken to include numbers that fall within a range of 5% in either direction (greater than or less than) the number unless otherwise stated or otherwise evident from the context (except where such number would exceed 100% of a possible value). Where ranges are stated, the endpoints are included within the range unless otherwise stated or otherwise evident from the context.

It should also be understood that, unless clearly indicated to the contrary, in any methods claimed herein that include more than one step or act, the order of the steps or acts of the method is not necessarily limited to the order in which the steps or acts of the method are recited.

Various embodiments and aspects of the present invention as delineated hereinabove and as claimed in the claims section below find experimental support in the following examples which, together with the above descriptions, illustrate some embodiments of the invention in a non-limiting fashion.

EXAMPLES

Example 1: Rapid, Large-Scale Screening of Metal-Biocide Combinations to Inactivate Pathogens

*E. coli* is a gram-negative bacterium that expresses resistant genes in response to toxin exposure. Intrinsic mechanisms exist that allow *E. coli* to survive toxic environments, and it can acquire resistance operons through horizontal and vertical gene transfer. *E. coli* harbors multiple antibiotic and metal resistance efflux proteins, as well as enzymes, which export and or/destroy copper, silver, bile salts, hormones, antibiotics and biocides. Proteins such as exporter AcrAB-TolC are constitutively expressed, while others are epigenetically regulated by exposure to the biocide, resulting in overexpression of the designated protein. The combination of acquired and intrinsic resistance allows for the survival of *E. coli* in natural, engineered, and toxic environments.

Due to the high level of resistance conferred by *E. coli* and other pathogens, both traditional and novel methods of inactivation have been aggressively pursued. These include use of antibiotics, metals, enzymes, phages, peptides, efflux pump inhibitors, physical methods (thermo-spectral energy), electron ionization, and nanomaterials, among others. Synergistic combinations with Group IB metals show promise as treatment options, and is the focus of this report. Silver ion is a biocide, and in combination with antibiotics, can work synergistically to inactivate *E. coli*. These include combinations with efflux pump inhibitors, aminoglycosides, glycopeptides, sulfa drugs, and fluoroquinolones, with varying mechanisms of action. Copper can also act synergistically with β-lactams, cationic detergents, aminoglycosides and macrolides. Gold ion interactions with antibiotics are limited to phenothiazines, salicylates, and polymyxins, likely due to lack of toxicity imparted by the gold ion.

Interactions with Silver—Silver is among the most lethal of metals to microorganisms. Silver ion has the ability to generate reactive oxygen species, induce DNA damage, and bind to sulfur-containing proteins. Adverse effects on microbes differ from eukaryotic cells in severity, making silver application an attractive option for pathogen elimination, while inducing little damage to the host organism. Combinations of silver with antimicrobials enhances the activity of both, a strategy employed when bacteria develop resistance mechanisms and survive pharmaceutical therapy. For example, *E. coli* have developed resistance mechanisms to silver, including the intrinsically expressed CusCFBA and loss of expression of outer membrane porins.

Antibiotics with silver: Herisse et al. (*Molecular Microbiology*. 2017; 105(1):115-26) reported that silver enhances the activity of aminoglycosides, and oxidative stress caused by silver ion was not necessary for elevated toxicity. Membrane permeability also increased with silver application, allowing vancomycin (a glycopeptide) inhibition to be enhanced. Sulfonamides interfere with folate synthesis, and interactions with silver enhance the antimicrobial effects. Silver sulfadiazine is inhibitory against *E. coli* and *Staphylococcus*, a combination that is available commercially and is typically used to treat *Pseudomonas aeruginosa* infected burn wounds. The combination is more effective with nanoparticle delivery. Silver and gold sulfamethoxazole were effective against *E. coli* greater than the sulfonamide alone, along with silver sulfathiazole and sulfamethoxazole. Trimethoprim and silver are synergistic towards a number of pathogens. Elevated activity with the fluoroquinolone ofloxacin has been reported. Diamide, an oxidizing agent, in combination with metals and ROS acted synergistically towards *E. coli*.

Metal chelators with silver: As a transition metal, silver can form complexes with heteroatoms, leading to a complicated mechanism of lethality. The complex could tie up silver internally, preventing efflux, or the complex itself is toxic. Previously, silver complexes of hydroxycoumarins and phenanthroline act synergistically on *E. coli*. Imidazole-derivatives with silver were inhibitory towards *E. coli*, where silver complexes with the nitrogen of imidazole heteroatoms. These studies did not report antimicrobial pathways.

Efflux pump inhibitors with silver: Silver mixed with ionophores such as Carbonyl cyanide m-chlorophenylhydrazone (CCCP) and Carbonyl cyanide-p-trifluoromethoxyphenylhydrazone (FCCP) have been used to test the real-time efflux of silver by metal exporters. Efflux of the ion is halted by the ionophore, which then increased intracellular toxicity by silver ions. Phenothiazines are also efflux pump inhibitors, and may prevent the resistance nodulation cell division (RND) protein CusCFBA from exporting silver ions. Silver phenothiazine activity was measured using the zone of inhibition method and minimum inhibitory concentration in a separate study, but the complex was not effective compared to the control (as determined by the zone of inhibition).

Interactions with Copper—Like silver, copper is toxic to microorganisms due to the development of reactive oxygen species, or ROS. In order to combat intracellular toxicity, various redox and efflux mechanisms are induced in *E. coli*, including expression of CopA, a P-type ATP-ase that transports $Cu^+$ from the cytoplasm to the periplasm, expression of CusCFBA, which exports $Cu^+$ out of the periplasm, and CueO, which oxidizes $Cu^+$ to $Cu^{2+}$, thereby eliminating the monovalent copper's ability to generate hydroxyl radicals, the presumed ROS species.

Antibiotics with copper: Kanamycin-copper has been shown to degrade RNA, while gentamicin-copper degrades DNA and is involved in lipid peroxidation. Copper complexes to tetracycline act synergistically and damage DNA. Copper and cationic detergent synergism was observed in tests against *Staphylococcus aureus* and *Pseudomonas aeruginosa*. Reported combinations included copper with the detergent cetrimide, a quaternary ammonium salt (QAS) and cationic detergent. A formulation of biocidal paint containing copper and the antifungal tolylfluanid that supports chemical interactions between the two was reported; however, the analysis lacked microbial evidence. Other copper-biocide interactions include copper-salicylates, copper ketoprofen, which likely binds to DNA, copper imidazole complexes, which are bacteriostatic in gram-negative bacteria, DNA-damaging copper-rifamycin, and copper complexes of substituted guanidines.

Metal chelators with copper: Copper chelators may bind the metal and eliminate toxicity by preventing the Fenton-like ROS generation, thereby enhancing growth. Copper bound to phenanthroline is an oxidizing agent and mimics DNAse intracellularly, while copper complexes of 2,2'bi-pyridyl inhibit the electron transport chain in bacteria. The copper chelating classes imidazoles and pyrroles increase antimicrobial effectiveness in molds, yeast, and fungi, and was observed with ornidazole, a nitroimidazole antibiotic, on *E. coli*.

Oxidizing agents with copper: Oxidizing agents may play multiple roles in increasing toxicity when applied with copper, including maintaining copper as $Cu^{2+}$, preventing export of the monovalent ion by CusCFBA. Of the inhibitory combinations in this screen, mechanisms have been previously reported, including copper complexes to lawsone, where it binds to double stranded DNA. Copper complexes to plumbagin are cytotoxic to cancer cells, and those to plumbagin derivatives are antimicrobial through R-plasmid curing. Plumbagin is also involved in redox cycling of copper. Other oxidants have increased antimicrobial activity, including mixtures of Cu-iodoacetate and Cu-diamide derivatives.

Interactions with $Au^{3+}$—Little is reported on gold toxicity, perhaps because as a rare earth metal, intracellular mechanisms are unknown, or it is not harmful to *E. coli*. However, *Salmonella typhimurium* expresses the gold efflux complex GesABC in response to $Au^{3+}$ (and other antibiotics). A protein alignment of the inner-membrane protein GesB that is responsible for substrate specificity (accession # Q8ZRG9) showed that it shares homology with *E. coli* multi-drug RND transporter permease subunit OqxB (Accession # Q69HW2, 74% positives, 56% identity). *E. coli* likely has the machinery to respond to gold ion accumulation. While the application of gold in antibiotics could be costly, this is a largely unexplored area with potential to control pathogenic *E. coli*.

The reported number of biocides that synergistically interact with gold (III) was much lower than that for silver and copper. Gold polymyxin complexes have been used to identify the site location of the antibiotic in *E. coli*. Phenothiazines alone are inhibitory towards gram-negative bacteria, act by intercalating with DNA, and contribute to in vitro plasmid elimination. Gold-phenothiazines are not mutagenic (DNA) in the host, but are anti-plasmid to the vector. Guanidine is used to bind gold ions, and guanidine itself is antimicrobial. Gold thiosalicylate has been synthesized and can inhibit growth in bacteria.

While these studies cover numerous antibiotic classes, each report is limited in the number of analytes, synergistic combinations, and bacteria strains tested. Accordingly, as described in this disclosure, a high-throughput method has been developed that validates published reports discussed herein, and reveals the identification of new Group IB-antibiotic combinations. These data demonstrate that this high-throughput approach can be used to study biocide mixtures, and should be considered to combat pathogenic survival.

TABLE 1

Biocides present in Biolog's chemical sensitivity tests. Toxic cations and anions, also plated in the panels, were not evaluated for this study.

| Biocide | Class: chemicals |
|---|---|
| Chelator | Carboxylic acid: EDTA, EGTA, fusaric acid |
| | Hydroxyquinoline: 5,7-dichloro-8-hydroxyquinaldine, 5,7-dichloro-8-hydroxyquinoline, 5-chloro-7-iodo-8-hydroxyquinoline, 8-hydroxyquinoline |
| | N-heterocycle: 1,10-phenanthroline, 2,2'-dipyridyl |
| | Other: sodium pyrophosphate decahydrate |
| DNA & RNA | DNA alkylation: chlorambucil, 5-Azacytidine |
| | Fluoroquinolone: ciprofloxacin, enoxacin, lomefloxacin, norfloxacin, ofloxacin |
| | Intercalator: 2-phenylphenol, 4-hydroxycoumarin, 9-aminoacridine, acriflavine, coumarin, novobiocin, proflavine, umbelliferone |
| | Nitrofuran analog: 5-nitro-2-furaldehyde semicarbazone, furaltadone, nitrofurantoin |
| | Purine analog: 6-mercaptopurine, azathioprine |
| | Pyrimidine analog: 5-fluoro-5'-deoxyuridine, 5-fluoroorotic acid, 5-fluorouracil, cytosine-1-beta-D-arabino-furanoside, trifluorothymidine |
| | Quinolone: cinoxacin, nalidixix acid, oxolinic acid, pipemidic acid |
| | Other: Disulfiram, myricetin, hydroxylamine, hexammine cobalt (III) chloride |
| Folate | Sulfonamide: sulfachloropyridazine, sulfadiazine, sulfamethazine, sulfamethoxazole, sulfamonomethoxine, sulfanilamide, sulfathiazole, sulfisoxazole |
| | Other: hydroxyurea, 2,4-diamino-6,7-diisopropyl-pteridine, trimethoprim |
| Fungicide | Phenylsulfamide: dichlofluanid, tolylfluanid |
| | Other: chloroxylenol, nordihydroguaiaretic acid |
| Ion channel | K+ inhibitor: 4-Aminopyridine |
| | Na+ inhibitor: lidocaine, procaine |
| Membrane | Anionic detergent: niaproof |
| | Cationic detergent: benzethonium chloride, cetylpyridinium chloride, dodecyltrimethyl ammonium bromide, domiphen bromide, methyltrioctylammonium chloride, poly-L-lysine, dequalinium chloride |
| | Electron transport: alexidine, chlorhexidine, hexachlorophene |
| | Guanidine (permeability): dodine, guanidine hydrochloride |
| | Phenothiazine chlorpromazine, promethazine, thioridazine, trifluoperazine |
| | Other: 1-hydroxypyridine-2-thione, protamine sulfate, amitriptyline |
| | Zwitterionic detergent: lauryl sulfobetaine |
| Other biocides | Acetylcholine antagonist: atropine, orphenadrine, pridinol |
| | Anti-capsule: ketoprofen, sodium salicylate, thiosalicylic acid |
| | Fatty acid synthesis: triclosan |
| | Nitroimidazole: 2-nitroimidazole, ornidazole, tinidazole |
| | Rifamycin: rifampicin, rifamycin SV |
| | Triazole: guanazole, 3-amino-1,2,4-triazole |
| | Other: D,L-propranolol, ethionamide, tannic acid, sanguinarine, semicarbazide, caffeine, humane, patulin, captan, Compound 48/80, chelerythrine, thioglycerol, phenylarsine oxide |
| Oxidation | Glutathione: 1-chloro-2,4-dinitrobenzene, diamide |
| | Oxidizing agent: d,1-thioctic acid, lawsone, methyl viologen, plumbagin, 3,4-dimethoxybenzyl alcohol |
| | Sulfhydryl: Iodoacetate |
| Protein | Aminoglycoside: amikacin, apramycin, capreomycin, dihydrostreptomycin, geneticin (G418), gentamicin, hygromycin B, kanamycin, neomycin, paromomycin, sisomicin, spectinomycin, streptomycin, tobramycin |
| | Lincosamide: lincomycin |
| | Macrolide: erythromycin, josamycin, oleandomycin, spiramycin, troleandomycin, tylosin |
| | Protein synthesis: blasticidin S, chloramphenicol, thiamphenicol, puromycin, fusidic acid |
| | Tetracycline: chlortetracycline, demeclocycline, doxycycline, minocycline, oxytetracycline, penimepicycline, rolitetracycline, tetracycline |
| | tRNA synthetase: D,L-serine hydroxamate, DL-methionine hydroxamate, glycine hydroxamate, L-Aspartic-β-hydroxamate, L-glutamic-g-hydroxamate |
| | Other: PMSF, β-chloro-L-alanine hydrochloride, benserazide |
| Respiration | $Ca^{2+}$ transporter: ruthenium red |
| | Ionophore: 18-Crown-6 ether, 2,4-dintrophenol, 3,5-dinitrobenzene, CCCP, cinnamic acid, FCCP, gallic acid, pentachlorophenol, sodium caprylate, sorbic acid |
| | Uncoupler: crystal violet, menadione, sodium azide, tetrazolium violet |
| | Other: oxycarboxin, iodonitro tetrazolium violet |
| Wall | Cephalosporin: cefamandole nafate, cefazolin, cefmetazole, cefsulodin, cefuroxime, cephalothin, moxalactam, cefoperazone, cefotaxime, cefoxitin, ceftriaxone |
| | Glycopeptide: bleomycin, phleomycin, vancomycin |
| | Monobactam: aztreonam |
| | Penicillin: amoxicillin, Ampicillin, aziocillin, carbenicillin, cloxacillin, nafcillin, oxacillin, penicillin G, phenethicillin, piperacillin |
| | Peptidoglycan synthesis: D-cycloserine, D-serine, glycine |
| | Polymyxin: colistin, polymyxin B |
| | Other: phosphomycin |

Materials and Methods for Data Analysis

Metal sensitivity tests. *E. coli* strain W3110 was pre-cultured in LB media or chloride-free LB (for silver ion studies) and seeded ($5 \times 10^5$ cell/mL) in increasing amounts of silver nitrate (Sigma Aldrich, >99%), copper sulfate (Sigma Aldrich, >99%), and gold chloride (Sigma Aldrich). Cultures were grown for 16 hours, after which the minimum inhibitory concentration (MIC) was determined.

Synergy assays. Four sub-lethal levels of $AgNO_3$ (0, 1, and 5 µM), $CuSO_4$ (0, 0.1, 0.5, and 1 mM), and $HAuCl_4$ (0, 5, 25, and 50 µM) were selected from the 16-hour sensitivity test for use in metal-antibiotic combination growth tests. Sterile metal solutions were dispensed in Biolog chemical sensitivity panels (PM11-PM20, summarized in Table 1), *E. coli* ($5 \times 10^5$ CFU/mL), Dye Mix A (1×, Biolog Catalog #74221), and LB media (final volume 100 µL, chloride-free for silver tests). The solution was dispensed in blank 96-well assay plates, which served as the metal control. A metal-free mixture (bacteria+media) was also dispensed into the Biolog panels, which served as the antibiotic control. Bacteria grown in LB or chloride-free LB served as the negative control. Growth curves were developed over a 24-hour period. Absorbance ($\lambda_{max}$=590 nm) at 16 hours was used to compare the growth of the bacteria in metal alone, antibiotic alone, and metal/antibiotic combination.

Coefficient of Drug Interaction. The coefficient of drug interaction (CDI) was used to evaluate if responses to drug combinations were additive, synergistic, or antagonistic. Using Equation 1, combinations were labelled additive if CDI≈1, synergistic if CDI<1, and antagonistic if CDI>1. An upper limit of 0.5 for a significantly synergistic effect (CDI<0.5), where relative growth (at 16 hours) was the test response. Relative growth, the growth normalized to that in LB media or chloride-free LB, was calculated for cultures grown in the antibiotic (A) alone, the metal ion alone (B), or the metal-antibiotic mixture (A+B). Data presented are the average of the two runs.

$$CDI = \frac{A+B}{A \times B} \quad \text{(Equation 1)}$$

Checkerboard analyses. Isobolograms were constructed from checkerboard assays to validate results generated from the high-throughput screen. Concentration combinations where toxicity was greater than 90% were extrapolated and plotted (chemical A. versus chemical B). A deflection of the curve towards the datum is indicative of synergism, while deflection away represents antagonism. A linear response connecting the MICs of two chemicals represents additivity.

Figure 7:
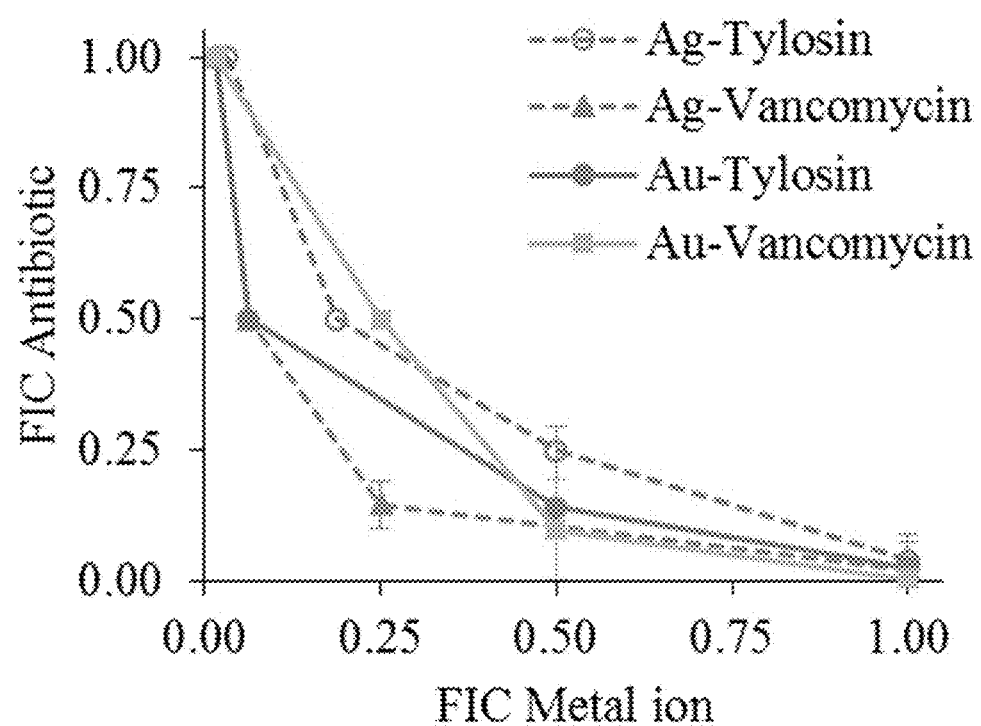
FIG. 7 presents data from checkerboard assays of four metal-antibiotic combinations.

Verification through isobolograms. Four metal-antibiotic combinations were subjected to checkerboard assays for validation of synergy (FIG. 7). Metal-antibiotic concentrations that inhibited growth were converted to fraction of inhibitory concentration (FIC) values according to:

$$FIC = \frac{C_{applied}}{MIC}, \quad \text{(Equation 2)}$$

where $C_{applied}$ is the final in-well concentration of antibiotic or metal, and MIC is the minimum inhibitory concentration of the respective metal or antibiotic. The isobologram generated shows the lines deflect towards the origin, indicating synergism. Integration of growth curve analysis, CDI values at 16 hours of the Biolog panels, and additional testing of individual chemicals on the checkerboard provides substantial evidence for synergism.

Results & Discussion

The objective of using a high-throughput screen was to evaluate the applicability of coefficient of drug interaction analysis on a commercially available set of microbial toxins. Comparable results were observed between published results and synergistic chemical pairs with this assay (FIG. 1, Tables 2-4), indicating that the biocide classes and plated concentrations are employable in combination tests. We also sought to use this as a preliminary screen to discover new Group IB/biocide pairs, laying the groundwork to pursue toxic mechanisms and optimal metal/biocide ratios.

Synergistic silver-biocide combinations. Silver with the metal chelating carboxylic acids and hydroxyquinolines, nucleic acid antibiotics (intercalators and nitrofurans), folate synthesis inhibitors (sulfonamides), membrane active biocides (guanidines, phenothiazines, a limited number of cationic detergents), protein antibiotics (aminoglycosides, macrolides, fenicols), respiration disruptors (ionophores and uncouplers) and biocides acting on the cell wall (polymyxins and glycopeptides) generated synergistic CDI values (FIG. 1, Table 2). Individual chemicals are also listed. Many combinations are reported in literature and were discussed here, including the silver-sulfonamides, silver-aminoglycosides, and silver-efflux pump inhibitors. Unique combinations that worked synergistically with soluble silver are shown in Table 2 (italicized therein).

Synergistic copper-biocide combinations. Copper-biocide interactions that resulted in synergistic CDI values included mixtures with oxidizing agents and respiration disruptors (FIG. 1, Table 3). Novel biocide-copper mixtures discovered with this screen (see italicized biocides in Table 3) include copper with chlorodinitrobenzene, thioctic acid, iodonitrotetrazolium violet, fusidic acid, nordihydroguaiaretic acid, triazole, thiamphenicol, zwitterionic (lauryl sulfobetaine) detergents, anionic detergents (niaproof), menadione, and lidocaine.

Synergistic Au-biocide combinations. In this screen, toxic interactions were observed between gold and macrolides, guanidines, glycopeptides, and polymyxins and other individual chemicals (FIG. 1, Table 4). Combinations of gold ion with glycopeptides, polymyxins, macrolides, and the individual chemicals disulfiram (a purine analog), thiosalisylic acid, novobiocin, and chlorpromazine generated strongly synergistic (CDI<0.1) effects and should be pursued further. Unique combinations uncovered here included those with macrolides, glycopeptides, and sodium channel blockers (see italicized biocides in Table 4).

TABLE 2

Synergistic silver-biocide combinations that inactivated *E. coli* W3110

| Biocide class | Chemical |
|---|---|
| Chelator | Carboxylic acid: EDTA, EGTA<br>Hydroxyquinoline: *5,7-dichloro-8-hydroxyquinaldine, 5,7-dichloro-8-hydroxyquinoline, 5-chloro-7-iodo-8-hydroxyquinoline, 8-hydroxyquinoline*<br>N-heterocycle: 1,10-phenanthroline<br>Other: sodium pyrophosphate decahydrate |
| DNA & RNA | Intercalator: 4-hydroxycoumarin, *9-aminoacridine, acriflavine, novobiocin, proflavine*<br>Nitrofuran analog: 5-Nitro-2-furaldehyde semicarbazone, furaltadone, nitrofurantoin<br>Other: disulfiram, myricetin<br>Purine analog: azathioprine<br>Pyrimidine analog: 5-Fluorouracil |
| Folate | Other: 2,4-Diamino-6,7-diisopropylpteridine, hydroxyurea<br>Sulfonamide: sulfachloropyridazine, sulfadiazine, sulfamethazine, sulfamethoxazole, sulfamonomethoxine, sulfathiazole |
| Fungicide | *Lipoxygenase: nordihydroguaiaretic acid*<br>*Phenylsulfamide: dichlofluanid, tolylfluanid* |
| Ion channel | *Na+ blocker: lidocaine, procaine* |
| Membrane | Cationic detergent: benzethonium chloride, dequalinium chloride, dodecyltrimethyl ammonium bromide<br>Electron transport: alexidine<br>*Guanidine: dodine, guanidine hydrochloride*<br>Other: 1-hydroxypyridine-2-thione, amitriptyline<br>*Phenothiazine: chlorpromazine, promethazine, thioridazine, trifluoperazine* |
| Other biocide | Anti-capsule: ketoprofen<br>*Acetylcholine antagonist: atropine, orphenadrine*<br>*Nitroimidazole: 2-nitroimidazole, ornidazole*<br>Other: chelerythrine, Compound 48/80, *D,L-propranolol*, ethionamide, *patulin, sanguinarine*, tannic acid<br>Rifamycin: rifamycin SV<br>Triazole: 3-Amino-1,2,4-triazole |
| Oxidation | Glutathione: 1-chloro-2,4-dinitrobenzene, diamide<br>Oxidizing agent: 3,4-dimethoxybenzyl alcohol, *methyl viologen*<br>*Sulfhydryl: iodoacetate* |
| Protein | Aminoglycoside: amikacin, apramycin, capreomycin, geneticin (G418), gentamicin, hygromycin B, kanamycin, paromomycin, sisomicin, spectinomycin, streptomycin, tobramycin<br>Lincosamide: lincomycin<br>*Macrolide: erythromycin, josamycin, oleandomycin, troleandomycin, tylosin*<br>Other: *benserazide*, PMSF, β-Chloro-L-alanine HCl<br>Protein synthesis: chloramphenicol, fusidic acid, puromycin, thiamphenicol<br>Tetracycline: penimepicycline<br>*tRNA synthetase: D,L-serine hydroxamate, D,L-methionine hydroxamate, L-glutamic-γ-hydroxamate* |
| Respiration | Ca2+ transporter: ruthenium red<br>Ionophore: 18-crown-6 ether, CCCP, FCCP, pentachlorophenol, sorbic acid<br>Other: Oxycarboxin<br>Uncoupler: Tetrazolium violet |
| Wall | β-lactam: oxacillin<br>Cephalosporin: cefotaxime, cephalothin<br>Glycopeptide: bleomycin, phleomycin, vancomycin<br>Other: phosphomycin<br>Polymyxin: colistin, polymyxin B |

* Chemicals in italics are combinations with silver that have not been previously reported

TABLE 3

Synergistic copper-biocide combinations that inactivated *E. coli* W3110.

| Biocide class | Chemical |
|---|---|
| Chelator | Carboxylic acid: fusaric acid<br>N-heterocycle: 1,10-phenanthroline |
| DNA & RNA | Intercalator: 2-phenylphenol, 4-hydroxycoumarin<br>Other: disulfiram, myricetin<br>Purine analog: azathioprine |
| Fungicide | *Lipoxygenase: nordihydroguaiaretic acid*<br>Phenylsulfamide: dichlofluanid |
| Ion channel | *Na+ blocker: lidocaine* |
| Membrane | Cationic detergent: benzethonium chloride, methyltrioctylammonium chloride<br>*Anionic detergent: Niaproof*<br>Guanidine: guanidine hydrochloride<br>Phenothiazine. trifluoperazine<br>*Zwitterionic detergent: lauryl sulfobetaine* |

TABLE 3-continued

Synergistic copper-biocide combinations that inactivated *E. coli* W3110.

| Biocide class | Chemical |
|---|---|
| Other biocide | Anti-capsule: ketoprofen, sodium salicylate |
| | Acetylcholine antagonist: atropine, pridinol |
| | Nitroimidazole: ornidazole, tinidazole |
| | Other: captan, semicarbazide |
| | Rifamycin: rifampicin, rifamycin SV |
| | *Triazole: 3-amino-1,2,4-triazole* |
| Oxidation | *Glutathione: 1-chloro-2,4-dinitrobenzene* |
| | Oxidizing agent: *D,L-thioctic acid*, lawsone, plumbagin |
| | Sulfhydryl: iodoacetate |
| Protein | Aminoglycoside: capreomycin, dihydrostreptomycin, geneticin (G418), paromomycin |
| | Macrolide: oleandomycin |
| | Other: PMSF |
| | Protein synthesis: blasticidin S, *fusidic acid*, puromycin, *thiamphenicol* |
| | Tetracycline: demeclocycline |
| | tRNA synthetase: glycine hydroxamate |
| Respiration | $Ca^{2+}$ transporter: Ruthenium red |
| | Ionophore: 2,4-dintrophenol, 3,5-dinitrobenzene, CCCP, FCCP, pentachlorophenol, sodium caprylate |
| | *Other: iodonitro tetrazolium violet* |
| | Uncoupler: *menadione*, tetrazolium violet |
| Wall | Cephalosporin: cefazolin, cefmetazole, cefoxitin, ceftriaxone |
| | Monobactam: aztreonam |
| | Polymyxin: colistin |

* Chemicals in italics are combinations with copper that have not been previously reported

TABLE 4

Synergistic gold-biocide combinations that inactivated *E. coli* W3110.

| Biocide class | Chemical |
|---|---|
| Chelator | Carboxylic acid: EDTA |
| DNA & RNA | Intercalator: novobiocin |
| | Other: *disulphiram* |
| Ion channel | Na+ channel blocker: lidocaine, procaine |
| Membrane | Cationic detergent: methyltrioctyl ammonium bromide, domiphen bromide |
| | Guanidine: dodine, guanidine hydrochloride |
| | Other: 1-hydroxypyridine-2-thione, protamine sulfate |
| | Phenothiazine: chlorpromazine |
| Other biocide | Anti-capsule: thiosalicylic acid |
| | Rifamycin: rifampicin |
| Oxidation | Oxidizing agent: methyl viologen |
| Protein | *Macrolide: erythromycin, oleandomycin, spiramycin, troleandomycin, tylosin* |
| | Protein synthesis: fusidic acid |
| Respiration | Ionophore: CCCP |
| | Uncoupler: tetrazolium violet |
| Wall | β-lactam: aziocillin, cloxacillin |
| | Cephalosporin: ceftriaxone, cefuroxime |
| | Glycopeptide: bleomycin, vancomycin, phleomycin |
| | Other: phosphomycin |
| | Polymyxin: colistin, polymyxin B |

* Chemicals in italics are combinations with gold that have not been previously reported.

Table 5 presents CDI data for silver, copper, and gold mixed with biocides. Values calculated as described above. "Tox" entries represent toxic biocides for which there was no growth, leading to errors in CDI calculation. Synergistic combinations (CDI<0.5) were determined from this CDI data of combinations of Ag/Cu/Au (3 concentrations each) with 240 biocides (four concentrations each), which was the average of two independent experiments.

The precise mechanism of lethality for all metal-biocide combinations will vary as biocides act on different bacteria structures, which may be distinct from a metal complex, if formed. Due to the large amount of biocides reviewed and screened, one can generally speculate on the mechanism of certain classes. Mechanistic studies will provide additional insight into antimicrobial modes of action.

Conclusions. In summary, this example describes development of a streamlined screening process to find synergistic combinations of soluble Group IB metals with biocides to inactivate *E. coli*. Results were reproducible when compared to conventional MIC, checkerboard, and time-kill tests reviewed in literature. Silver not only works synergistically with antimicrobials, but also with chelators and efflux pump inhibitors. Further convincing results validated copper synergism with ionphores and oxidizing agents. Finally, gold synergy with macrolides and glycopeptides reveals a new direction in antimicrobial therapy. Because our findings support previous studies, the high-throughput method can be used as a preliminary screen to evaluate other combinations of antimicrobials, including those with radiation, toxic ions, nanomaterials, and plasmid curing agents. This high-throughput screen lays the foundation to apply fundamental microbial toxicity tests and to further study mechanisms of inactivation.

The present disclosure has been described in terms of one or more preferred embodiments, and it should be appreciated that many equivalents, alternatives, variations, and modifications, aside from those expressly stated, are possible and within the scope of the disclosure.

TABLE 5

CDI data for silver, copper, and gold mixed with biocides.
Values calculated as described in manuscript. Tox = toxic biocide
(no growth), leading to error in CDI calculation.

| Drug Class | | Chemical | Silver ($\mu$M) | | | | | | | | | | | |
|---|---|---|---|---|---|---|---|---|---|---|---|---|---|---|
| | | | 0.5 | | | | 1.0 | | | | 5.0 | | | |
| Chelator | Carboxylic acid | EGTA | 0.74 | 0.86 | 0.82 | 0.92 | 1.02 | 1.07 | 1.01 | 1.02 | 1.13 | 0.98 | 0.72 | 0.4 |
| | | Fusaric acid | 1.12 | Tox | Tox | Tox | 0.91 | Tox | Tox | Tox | 0.6 | Tox | Tox | Tox |
| | | EDTA | 1.05 | 0.97 | 0.85 | Tox | 0.84 | 0.86 | 0.89 | Tox | 0.61 | 0.38 | 0.23 | Tox |
| | Hydroxyquinoline | 5,7-Dichloro-8-hydroxyquinoline | 0.97 | 0.91 | 0.77 | 0.58 | 1.01 | 0.79 | 0.85 | Tox | 0.43 | 0.23 | 0.45 | Tox |
| | | 8-Hydroxyquinoline | 0.77 | 0.69 | 0.64 | Tox | 0.75 | 0.78 | 0.74 | Tox | 0.53 | 0.58 | 0.37 | Tox |
| | | 5,7-Dichloro-8-hydroxyquinaldine | 0.89 | 0.66 | 0.6 | Tox | 0.74 | 0.68 | 0.46 | Tox | 0.16 | 0.11 | 0.25 | Tox |
| | | 5-Chloro-7-iodo-8-hydroxyquinoline | 0.55 | 0.59 | 0.48 | 0.46 | 0.77 | 0.55 | 0.5 | 0.54 | 0.1 | 0.2 | 0.2 | 0.05 |
| | Other | 2,2'-Dipyridyl | 1.55 | Tox | Tox | Tox | 1.07 | Tox | Tox | Tox | 1.21 | Tox | Tox | Tox |
| | | 1,10-Phenanthroline | 0.79 | 0.68 | Tox | Tox | 0.90 | 0.70 | Tox | Tox | 0.56 | 0.31 | Tox | Tox |
| | | Sodium pyrophosphate decahydrate | 0.98 | 0.96 | 0.84 | 0.69 | 0.82 | 0.83 | 0.74 | 0.63 | 1.13 | 0.88 | 0.70 | 0.13 |
| DNA & RNA | DNA Alkylation | 5-Azacytidine | 1.05 | 0.97 | 0.99 | 0.87 | 0.98 | 0.97 | 1.00 | 0.95 | 1.06 | 0.94 | 0.99 | 0.87 |
| | | Chlorambucil | 0.79 | 0.95 | 1.46 | 1.04 | 0.90 | 1.02 | 1.18 | 0.74 | 0.63 | 0.56 | 0.57 | 0.63 |
| | Fluoroquinolone | Enoxacin | 0.99 | 2.65 | Tox | Tox | 1.06 | Tox | Tox | Tox | 1.04 | Tox | Tox | Tox |
| | | Ciprofloxacin | 0.98 | 1.05 | Tox | Tox | 0.94 | 1.00 | Tox | Tox | 1.08 | 0.90 | Tox | Tox |
| | | Lomefloxacin | 0.81 | 0.98 | Tox | Tox | 1.05 | 1.08 | Tox | Tox | 1.08 | 0.90 | Tox | Tox |
| | | Norfloxacin | 0.95 | 1.00 | 1.35 | Tox | 0.91 | 1.00 | 1.35 | Tox | 0.52 | 0.55 | 1.03 | Tox |
| | | Ofloxacin | 0.78 | 0.82 | 1.01 | Tox | 0.89 | 0.93 | 0.98 | Tox | 1.03 | 1.01 | 0.61 | Tox |
| | Intercalator | 2-Phenylphenol | 0.95 | 0.98 | Tox | Tox | 1.01 | 1.14 | Tox | Tox | 1.12 | 1.38 | Tox | Tox |
| | | Umbelliferone | 0.92 | 1.34 | 1.20 | 0.78 | 0.92 | 0.99 | 1.01 | 1.00 | 1.37 | 1.06 | 0.84 | 1.21 |
| | | Coumarin | 0.81 | 0.88 | 0.73 | Tox | 0.82 | 0.80 | 0.81 | Tox | 1.31 | 1.41 | 1.21 | Tox |
| | | Proflavine | 1.00 | 1.04 | 1.00 | 0.98 | 0.84 | 1.00 | 1.00 | 0.63 | 1.07 | 1.14 | 0.76 | 0.36 |
| | | 4-Hydroxy-coumarin | 1.18 | 1.07 | 0.99 | Tox | 1.05 | 0.88 | 0.74 | Tox | 0.95 | 0.57 | 0.33 | Tox |
| | | Novobiocin | 0.84 | 0.62 | 1.05 | 1.04 | 0.82 | 0.46 | 1.08 | 0.93 | 0.70 | 0.06 | 1.33 | 1.43 |
| | | 9-Aminoacridine | 0.96 | 0.89 | 0.82 | Tox | 0.94 | 0.88 | 0.80 | Tox | 1.13 | 0.98 | 0.32 | Tox |
| | | Acriflavine | 0.99 | 1.03 | 0.86 | 0.73 | 0.97 | 0.95 | 0.87 | 0.59 | 0.96 | 1.02 | 0.54 | 0.24 |
| | Nitrofuran analog | Furaltadone | 1.01 | 0.69 | Tox | Tox | 0.98 | 0.76 | Tox | Tox | 0.96 | 0.13 | Tox | Tox |
| | | Nitrofurantoin | 0.88 | 0.86 | 0.56 | Tox | 0.90 | 0.91 | 0.56 | Tox | 0.93 | 0.52 | 0.03 | Tox |
| | | 5-nitro-2-furaldehyde semicarbazone | 1.00 | 0.88 | Tox | Tox | 0.85 | 0.69 | Tox | Tox | 0.43 | 0.23 | Tox | Tox |
| | Other | Hydroxylamine | 0.76 | 0.77 | 0.68 | 2.32 | 0.93 | 0.90 | 0.83 | 1.67 | 1.40 | 1.44 | 1.25 | 0.86 |
| | | Hexammine cobalt (III) chloride | 0.98 | 1.05 | 0.97 | 0.82 | 0.98 | 1.03 | 1.04 | 0.39 | 1.26 | 1.43 | 1.00 | 1.17 |
| | | Disulphiram | 0.87 | 0.52 | 0.36 | Tox | 1.10 | 1.04 | 1.07 | Tox | 1.40 | 1.37 | 1.05 | Tox |
| | | Myricetin | 0.94 | 0.85 | 1.24 | 1.22 | 0.98 | 0.97 | 0.98 | 0.75 | 1.04 | 0.82 | 1.05 | 0.39 |
| | Purine analog | 6-Mercapto-purine | 1.04 | 0.96 | 1.46 | 1.25 | 0.96 | 1.04 | 1.66 | 1.14 | 1.68 | 1.61 | 1.61 | 1.60 |
| | | Azathioprine | 0.87 | 0.72 | 0.81 | 0.57 | 0.82 | 0.74 | 0.58 | 0.58 | 0.68 | 0.38 | 0.53 | 0.23 |
| | Pyrimidine analog | 5-fluoro-5'-deoxyuridine | 0.82 | 0.86 | 0.88 | 0.95 | 0.96 | 1.05 | 1.07 | 1.09 | 1.08 | 1.18 | 1.25 | 1.43 |
| | | Trifluorothymidine | 0.97 | 1.01 | 1.09 | 1.01 | 0.98 | 0.94 | 0.93 | 0.84 | 1.20 | 1.07 | 1.15 | 0.97 |
| | | Cytosine-1-$\beta$-D-arabinofuranoside | 0.91 | 0.94 | 0.94 | 0.90 | 0.95 | 0.93 | 1.01 | 1.00 | 1.07 | 0.91 | 0.95 | 1.19 |
| | | 5-Fluorouracil | 1.16 | 0.94 | Tox | Tox | 0.98 | 1.04 | Tox | Tox | 1.00 | 0.46 | Tox | Tox |
| | | 5-Fluoroorotic acid | 0.92 | 0.76 | 0.76 | 0.54 | 1.04 | 0.87 | 1.00 | 0.79 | 0.91 | 0.83 | 1.03 | 0.97 |
| | Quinolone | Cinoxacin | 0.97 | 1.37 | Tox | Tox | 1.06 | 1.21 | Tox | Tox | 1.05 | 0.94 | Tox | Tox |
| | | Pipemidic Acid | 1.25 | 1.25 | 1.16 | 1.09 | 1.00 | 0.99 | 0.88 | 0.88 | 0.97 | 1.00 | 0.95 | 1.08 |
| | | Nalidixic Acid | 0.71 | 0.93 | Tox | Tox | 0.92 | 0.94 | Tox | Tox | 1.00 | 0.98 | Tox | Tox |
| | | Oxolinic acid | 0.91 | 0.93 | 0.80 | 0.76 | 0.85 | 0.87 | 0.84 | 0.89 | 0.97 | 0.77 | 0.89 | 1.03 |
| Folate | Other | 2,4-Diamino-6,7-diisopropylpteridine | 1.46 | 0.97 | 0.86 | Tox | 1.13 | 0.96 | 0.76 | Tox | 1.13 | 0.56 | 0.37 | Tox |
| | | Hydroxyurea | 0.91 | 0.94 | 0.94 | Tox | 0.88 | 1.08 | 0.86 | Tox | 1.09 | 0.83 | 0.25 | Tox |
| | | Trimethoprim | 0.90 | Tox | Tox | Tox | 0.87 | Tox | Tox | Tox | 0.55 | Tox | Tox | Tox |
| | Sulfonamide | Sulfanilamide | 1.23 | 1.17 | 1.07 | 0.91 | 1.01 | 0.98 | 0.86 | 0.72 | 0.87 | 0.98 | 1.04 | 1.19 |
| | | Sulfamethoxazole | 1.01 | 0.79 | 0.80 | 0.60 | 1.14 | 1.08 | 1.04 | 0.72 | 1.14 | 0.97 | 0.94 | 0.51 |
| | | Sulfamethazine | 0.98 | 0.97 | 1.00 | 0.78 | 0.91 | 0.93 | 0.97 | 0.60 | 0.97 | 1.04 | 0.94 | 0.35 |
| | | Sulfathiazole | 1.00 | 0.91 | 0.84 | 0.49 | 1.11 | 1.06 | 0.90 | 0.64 | 1.20 | 1.01 | 0.90 | 0.38 |
| | | Sulfadiazine | 0.97 | 0.97 | 0.82 | 0.71 | 0.99 | 1.07 | 0.78 | 0.72 | 1.00 | 0.86 | 0.59 | 0.29 |
| | | Sulfachloro-pyridazine | 1.02 | 0.95 | 0.83 | 0.88 | 0.91 | 0.89 | 0.73 | 0.58 | 0.78 | 0.76 | 0.62 | 0.30 |
| | | Sulfisoxazole | 1.08 | 0.96 | Tox | Tox | 0.77 | 0.68 | Tox | Tox | 0.58 | 0.40 | Tox | Tox |
| | | Sulfamono-methoxine | 0.85 | 0.70 | 0.59 | 0.76 | 0.86 | 0.83 | 0.67 | 0.41 | 0.70 | 0.43 | 0.26 | 0.01 |

TABLE 5-continued

| | | | | | | | | | | | | | | |
|---|---|---|---|---|---|---|---|---|---|---|---|---|---|---|
| Mem-brane | Cationic detergent | Methyltrioctyl NH4+ Br− | 1.01 | 0.90 | Tox | Tox | 1.04 | 1.09 | Tox | Tox | 1.66 | 1.73 | Tox | Tox |
| | | Poly-L-lysine | 0.92 | 0.96 | Tox | Tox | 0.88 | 0.88 | Tox | Tox | 1.01 | 1.04 | Tox | Tox |
| | | Domiphen bromide | 0.98 | 1.14 | Tox | Tox | 0.93 | 0.97 | Tox | Tox | 0.72 | 0.62 | Tox | Tox |
| | | Cetylpyridinium chloride | 0.88 | 0.72 | Tox | Tox | 1.00 | 0.95 | Tox | Tox | 0.89 | 0.60 | Tox | Tox |
| | | Dodecyltrimethyl NH$_4^+$ Br− | 0.63 | 0.91 | Tox | Tox | 1.00 | 1.04 | Tox | Tox | 0.59 | 0.47 | Tox | Tox |
| | | Benzethonium chloride | 0.94 | 0.84 | Tox | Tox | 0.90 | 0.61 | Tox | Tox | 0.96 | 0.07 | Tox | Tox |
| | Electron transport | Chlorhexidine | 0.96 | 0.83 | 0.82 | Tox | 0.98 | 0.91 | 0.90 | Tox | 1.59 | 1.53 | 1.46 | Tox |
| | | Hexa-chlorophene | 0.72 | 0.65 | 0.69 | 0.54 | 0.87 | 0.81 | 0.86 | 0.70 | 0.80 | 0.78 | 1.03 | 0.77 |
| | | Alexidine | 0.89 | 0.81 | Tox | Tox | 0.80 | 0.55 | Tox | Tox | 0.91 | 0.17 | Tox | Tox |
| | Guanidine | Dodine | 0.85 | 0.77 | Tox | Tox | 0.92 | 0.89 | Tox | Tox | 0.94 | 0.31 | Tox | Tox |
| | | Guanidine hydrochloride | 1.11 | 0.95 | 0.95 | Tox | 0.85 | 0.61 | 0.41 | Tox | 0.33 | 0.36 | 0.00 | Tox |
| | Other | Protamine sulfate | 1.10 | 1.15 | Tox | Tox | 0.95 | 1.00 | Tox | Tox | 0.84 | 0.90 | Tox | Tox |
| | | 1-Hydroxy-pyridine-2-thione | 1.14 | 1.03 | 0.96 | Tox | 0.99 | 0.97 | 1.41 | Tox | 0.80 | 0.55 | 0.34 | Tox |
| | | Amitriptyline | 0.84 | 1.11 | Tox | Tox | 0.89 | 1.10 | Tox | Tox | 0.91 | 0.43 | Tox | Tox |
| | | Niaproof | 1.07 | 1.17 | 1.04 | 1.74 | 1.04 | 1.17 | 0.99 | 1.45 | 0.89 | 0.99 | 0.78 | 0.55 |
| | | Lauryl sulfobetaine | 0.83 | 0.56 | Tox | Tox | 0.91 | 0.79 | Tox | Tox | 1.42 | 1.41 | Tox | Tox |
| | Phenothiazine | Promethazine | 0.85 | 0.88 | Tox | Tox | 0.99 | 1.05 | Tox | Tox | 1.28 | 0.49 | Tox | Tox |
| | | Chlorpromazine | 0.83 | 1.10 | Tox | Tox | 0.83 | 0.95 | Tox | Tox | 0.72 | 0.39 | Tox | Tox |
| | | Thioridazine | 1.06 | 1.05 | 0.89 | Tox | 0.35 | 0.27 | 0.75 | Tox | 0.01 | 0.35 | 1.19 | Tox |
| | | Trifluoperazine | 0.79 | 0.86 | 0.23 | Tox | 0.97 | 0.98 | 0.39 | Tox | 0.78 | 0.19 | 0.53 | Tox |
| Other biocide | Anti-capsule | Sodium salicylate | 0.99 | Tox | Tox | Tox | 1.44 | Tox | Tox | Tox | 0.85 | Tox | Tox | Tox |
| | | Thiosalicylic acid | 0.83 | 0.82 | 0.82 | Tox | 0.86 | 0.83 | 0.86 | Tox | 1.44 | 1.52 | 1.53 | Tox |
| | | Ketoprofen | 0.88 | 0.90 | 0.82 | Tox | 0.81 | 0.82 | 0.87 | Tox | 0.83 | 0.58 | 0.18 | Tox |
| | Acetylcholine antagonist | Pridinol | 0.76 | Tox | 1.22 | Tox | 0.84 | Tox | 1.06 | Tox | 0.61 | Tox | 1.29 | Tox |
| | | Atropine | 1.02 | 1.01 | Tox | Tox | 0.91 | 0.89 | Tox | Tox | 0.97 | 0.36 | Tox | Tox |
| | | Orphenadrine | 1.01 | Tox | Tox | Tox | 0.83 | Tox | Tox | Tox | 0.44 | Tox | Tox | Tox |
| | Glycopeptide | Phleomycin | 0.81 | 0.61 | 0.68 | Tox | 0.89 | 0.81 | 0.81 | Tox | 1.32 | 1.43 | 1.37 | Tox |
| | | Vancomycin | 1.04 | 0.95 | Tox | Tox | 0.80 | 0.76 | Tox | Tox | 0.46 | 0.23 | Tox | Tox |
| | | Bleomycin | 0.75 | 1.32 | Tox | Tox | 0.80 | 0.50 | Tox | Tox | 0.27 | 0.18 | Tox | Tox |
| | Fungicide | Nordihydroguaia retic acid | 0.84 | 0.85 | 1.31 | 0.90 | 0.91 | 0.87 | 1.00 | 0.49 | 0.43 | 0.29 | 0.41 | 0.64 |
| | | Chloroxylenol | 0.85 | 0.64 | Tox | Tox | 0.89 | Tox | Tox | Tox | 1.06 | Tox | Tox | Tox |
| | Phenylsulfamide | Tolylfluanid | 0.89 | 0.87 | 0.77 | 0.72 | 0.87 | 0.88 | 0.83 | 0.82 | 0.59 | 0.61 | 0.39 | 0.43 |
| | | Dichlofluanid | 0.58 | Tox | 0.87 | 0.90 | Tox | Tox | 0.90 | 0.54 | Tox | Tox | 0.22 | 0.31 |
| | Ion (K+) blocker | 4-Aminopyridine | 0.96 | 0.91 | 1.08 | 1.21 | 0.95 | 0.92 | 0.96 | 1.02 | 0.99 | 1.11 | 0.67 | 0.52 |
| | | Dequalinium chloride | 1.01 | 1.04 | 0.82 | 0.81 | 0.82 | 0.85 | 0.81 | 0.88 | 0.79 | 0.81 | 0.56 | 0.41 |
| | Ion (Na+) blocker | Procaine | 0.95 | 1.17 | 1.10 | 0.88 | 0.95 | 0.95 | 1.05 | 0.67 | 0.77 | 0.82 | 0.41 | 0.16 |
| | | Lidocaine | 0.73 | 0.55 | Tox | Tox | 0.79 | 0.77 | Tox | Tox | 0.36 | 0.24 | Tox | Tox |
| | Nitroimidazole | Tinidazole | 1.03 | 1.17 | 0.74 | Tox | 1.01 | 1.03 | 0.95 | Tox | 1.06 | 0.89 | 0.52 | Tox |
| | | 2-Nitroimidazole | 0.99 | 0.98 | Tox | Tox | 0.91 | 0.62 | Tox | Tox | 0.35 | 0.34 | Tox | Tox |
| | | Ornidazole | 0.73 | 0.57 | 0.52 | Tox | 0.81 | 0.75 | 0.48 | Tox | 0.91 | 0.59 | 0.13 | Tox |
| | Other | Tannic acid | 1.10 | 1.17 | 1.09 | 1.53 | 0.95 | 0.95 | 1.45 | 1.27 | 0.45 | 1.34 | 1.92 | 1.52 |
| | | Semicarbazide | 0.87 | 1.27 | Tox | Tox | 0.96 | 0.96 | Tox | Tox | 1.17 | 0.98 | Tox | Tox |
| | | Captan | 1.08 | 0.79 | 0.90 | Tox | 0.79 | 1.16 | 1.02 | Tox | 1.03 | 1.87 | 0.57 | Tox |
| | | Ethionamide | 0.87 | 1.00 | 0.46 | 0.40 | 0.85 | 0.82 | 0.86 | 0.58 | 1.40 | 1.48 | 0.94 | 1.14 |
| | | D,L-Propranolol | 1.03 | 1.15 | Tox | Tox | 0.82 | 0.87 | Tox | Tox | 0.89 | 0.46 | Tox | Tox |
| | | Compound 48/80 | 0.84 | 0.82 | 0.83 | Tox | 0.94 | 0.93 | 0.76 | Tox | 1.01 | 0.79 | 0.37 | Tox |
| | | Chelerythrine | 0.76 | 0.77 | 0.45 | 0.51 | 1.03 | 0.99 | 0.76 | 0.74 | 0.99 | 0.96 | 0.60 | 0.52 |
| | | Sanguinarine | 0.65 | 0.69 | Tox | Tox | 0.76 | 0.64 | Tox | Tox | 0.66 | 0.26 | Tox | Tox |
| | | Patulin | 0.68 | Tox | Tox | Tox | 0.38 | Tox | Tox | Tox | 0.12 | Tox | Tox | Tox |
| | Rifamycin | Rifampicin | 0.73 | 0.72 | Tox | Tox | 0.99 | 0.96 | Tox | Tox | 1.06 | 1.07 | Tox | Tox |
| | | Rifamycin SV | 1.12 | 0.91 | 1.27 | 1.07 | 0.28 | 0.10 | 1.22 | 1.14 | 0.03 | 0.08 | 1.73 | 1.54 |
| | Triazole | Guanazole | 0.95 | 1.12 | Tox | Tox | 1.01 | 1.03 | Tox | Tox | 0.97 | 0.73 | Tox | Tox |
| | | 3-Amino-1,2,4-triazole | 1.22 | 1.18 | 1.17 | Tox | 1.05 | 1.10 | 0.89 | Tox | 0.74 | 0.48 | 0.31 | Tox |
| | Oxidizing agent | Diamide | 1.19 | 1.07 | Tox | Tox | 1.01 | 0.90 | Tox | Tox | 0.97 | 0.40 | Tox | Tox |
| | | 1-Chloro-2,4-dinitrobenzene | 0.93 | 0.92 | 0.92 | 0.74 | 0.85 | 0.91 | 0.97 | 0.90 | 0.67 | 0.60 | 0.65 | 1.06 |
| | | D,L-Thioctic Acid | 1.26 | 1.00 | Tox | Tox | 1.07 | 0.97 | Tox | Tox | 1.53 | 1.44 | Tox | Tox |
| | | Lawsone | 0.92 | 0.95 | 0.55 | Tox | 1.01 | 0.98 | 0.92 | Tox | 1.40 | 1.31 | 1.02 | Tox |
| | | Plumbagin | 1.01 | 0.95 | 1.01 | 0.99 | 1.01 | 1.06 | 1.05 | 0.98 | 0.80 | 0.94 | 0.82 | 0.85 |
| | | 3,4-Dimethoxybenzyl alcohol | 0.98 | 1.17 | 1.20 | Tox | 0.88 | 1.16 | 0.87 | Tox | 0.97 | 0.87 | 0.46 | Tox |
| | | Methyl viologen | 0.89 | 0.73 | Tox | Tox | 0.48 | 0.20 | Tox | Tox | 0.07 | 0.01 | Tox | Tox |
| | | Iodoacetate | 1.04 | Tox | Tox | Tox | 0.36 | Tox | Tox | Tox | 0.00 | Tox | Tox | Tox |
| Protein | Aminoglycoside | Dihydro-streptomycin | 1.00 | 0.83 | 0.80 | Tox | 1.08 | 1.04 | Tox | Tox | 1.58 | 1.56 | Tox | Tox |
| | | Hygromycin B | 1.26 | 2.06 | Tox | Tox | 0.63 | 1.47 | Tox | Tox | 0.03 | 0.37 | Tox | Tox |
| | | Gentamicin | 0.87 | 0.86 | 0.81 | 0.79 | 1.04 | 0.98 | 0.42 | 0.38 | 1.00 | 0.82 | 0.74 | 0.34 |
| | | Sisomicin | 0.70 | 0.93 | 1.01 | 0.47 | 0.83 | 1.01 | 0.45 | 0.32 | 0.88 | 0.43 | 0.73 | 0.65 |
| | | Neomycin | 0.80 | 0.73 | 0.59 | 0.51 | 0.97 | 0.83 | 0.50 | 0.34 | 0.88 | 0.76 | 0.59 | 0.45 |
| | | Spectinomycin | 0.78 | 0.42 | Tox | Tox | 0.95 | 0.81 | Tox | Tox | 0.70 | 0.51 | Tox | Tox |
| | | Geneticin (G418) | 1.04 | 0.96 | 0.76 | Tox | 0.94 | 0.82 | 0.31 | Tox | 0.48 | 0.49 | 0.23 | Tox |
| | | Tobramycin | 0.78 | 0.90 | 1.02 | 0.15 | 0.89 | 1.07 | 0.57 | Tox | 0.57 | 0.42 | 0.25 | Tox |
| | | Paromomycin | 0.92 | 0.96 | 1.04 | Tox | 0.83 | 0.71 | 0.23 | Tox | 0.38 | 0.32 | 0.29 | Tox |

TABLE 5-continued

| | | | | | | | | | | | | | | |
|---|---|---|---|---|---|---|---|---|---|---|---|---|---|---|
| | | Amikacin | 0.97 | 0.93 | 0.71 | Tox | 0.93 | 0.56 | 0.20 | Tox | 0.85 | 0.37 | 0.13 | Tox |
| | | Kanamycin | 0.87 | 0.79 | 0.69 | Tox | 0.99 | 0.76 | 0.32 | Tox | 0.83 | 0.36 | 0.00 | Tox |
| | | Apramycin | 1.10 | 0.94 | 0.61 | Tox | 0.83 | 0.54 | 0.24 | Tox | 0.79 | 0.32 | 0.18 | Tox |
| | | Capreomycin | 0.95 | 0.92 | 0.96 | Tox | 0.69 | 0.37 | 0.35 | Tox | 0.41 | 0.11 | 0.02 | Tox |
| | | Streptomycin | 0.96 | Tox | Tox | Tox | 0.54 | Tox | Tox | Tox | 0.00 | Tox | Tox | Tox |
| | Macrolide | Josamycin | 0.90 | 0.92 | 0.72 | Tox | 0.83 | 0.84 | 0.56 | Tox | 1.56 | 1.44 | 0.46 | Tox |
| | | Spiramycin | 0.83 | Tox | Tox | Tox | 0.96 | Tox | Tox | Tox | 0.83 | Tox | Tox | Tox |
| | | Erythromycin | 0.80 | 0.67 | 0.80 | Tox | 0.99 | 0.97 | 0.86 | Tox | 1.03 | 0.79 | 0.40 | Tox |
| | | Oleandomycin | 0.97 | 1.03 | 0.97 | Tox | 0.88 | 0.93 | 0.74 | Tox | 0.75 | 0.48 | 0.38 | Tox |
| | | Tylosin | 0.70 | 0.53 | Tox | Tox | 0.92 | 0.86 | Tox | Tox | 0.59 | 0.33 | Tox | Tox |
| | | Troleandomycin | 0.70 | 0.77 | Tox | Tox | 0.81 | 0.40 | Tox | Tox | 0.43 | 0.45 | Tox | Tox |
| | Other | PMSF | 0.91 | 0.92 | 1.10 | 0.35 | 1.03 | 1.10 | 1.06 | 0.55 | 1.17 | 1.15 | 1.25 | 0.60 |
| | | Benserazide | 0.76 | 0.80 | 1.02 | 0.91 | 0.78 | 0.74 | 1.09 | 1.08 | 0.28 | 0.18 | 1.46 | 1.54 |
| | | β-Chloro-L-alanine HCl | 0.81 | 0.51 | Tox | Tox | 0.69 | 0.58 | Tox | Tox | 0.36 | 0.04 | Tox | Tox |
| | | Lincomycin | 0.81 | 0.51 | Tox | Tox | 0.84 | 0.78 | Tox | Tox | 0.73 | 0.46 | Tox | Tox |
| | Protein synthesis | Fusidic acid | 1.24 | Tox | Tox | 1.11 | 1.11 | Tox | Tox | 1.61 | 0.23 | Tox | Tox | 2.59 |
| | | Blasticidin S | 1.04 | 0.90 | 0.92 | Tox | 1.01 | 1.02 | Tox | Tox | 1.52 | 1.40 | Tox | Tox |
| | | Chloramphenicol | 0.86 | Tox | Tox | Tox | 0.86 | Tox | Tox | Tox | 0.46 | Tox | Tox | Tox |
| | | Puromycin | 1.05 | 0.52 | Tox | Tox | 1.05 | 0.83 | Tox | Tox | 0.61 | 0.30 | Tox | Tox |
| | | Chloramphenicol | 0.67 | 0.69 | Tox | Tox | 1.00 | 0.48 | Tox | Tox | 0.73 | 0.37 | Tox | Tox |
| | | Thiamphenicol | 0.36 | 0.24 | Tox | Tox | 0.62 | 0.63 | Tox | Tox | 0.61 | 0.31 | Tox | Tox |
| | Tetracycline | Doxycycline | 1.10 | Tox | Tox | Tox | 1.16 | Tox | Tox | Tox | 0.65 | Tox | Tox | Tox |
| | | Chlortetracycline | 0.97 | 1.16 | Tox | Tox | 0.94 | 0.98 | Tox | Tox | 0.81 | 0.78 | Tox | Tox |
| | | Oxytetracycline | 0.96 | 0.91 | 0.86 | 0.77 | 1.01 | 1.00 | 0.99 | 0.90 | 0.89 | 1.03 | 1.02 | 0.74 |
| | | Tetracycline | 0.92 | 0.85 | 1.15 | Tox | 0.93 | 0.88 | 0.88 | Tox | 1.03 | 0.91 | 0.50 | Tox |
| | | Demeclocycline | 0.95 | 0.87 | Tox | Tox | 0.95 | 0.96 | Tox | Tox | 0.72 | 0.88 | Tox | Tox |
| | | Minocycline | 0.82 | 0.77 | Tox | Tox | 0.98 | 1.03 | Tox | Tox | 0.66 | 1.04 | Tox | Tox |
| | | Penimepicycline | 1.04 | 1.10 | Tox | Tox | 0.91 | 0.91 | Tox | Tox | 0.49 | 0.34 | Tox | Tox |
| | | Rolitetracycline | 0.92 | 0.61 | Tox | Tox | 0.92 | 0.83 | Tox | Tox | 0.64 | 0.60 | Tox | Tox |
| | tRNA synthetase | Glycine hydroxamate | 0.74 | 0.72 | 0.79 | 0.76 | 0.95 | 0.99 | 0.95 | 1.07 | 1.00 | 0.95 | 1.09 | 0.88 |
| | | DL-Methionine hydroxamate | 0.88 | 1.04 | Tox | Tox | 1.04 | 0.99 | Tox | Tox | 0.71 | 0.42 | Tox | Tox |
| | | L-Aspartic-β-hydroxamate | 0.79 | 0.70 | 0.68 | 0.58 | 1.06 | 1.08 | 0.91 | 0.81 | 0.86 | 0.88 | 0.83 | 0.64 |
| | | L-Glutamic-g-hydroxamate | 0.93 | 0.75 | 0.61 | 0.49 | 1.12 | 0.97 | 0.93 | 0.71 | 1.00 | 0.85 | 0.71 | 0.34 |
| | | D,L-Serine hydroxamate | 0.90 | 0.66 | 0.31 | Tox | 0.89 | 0.77 | 0.62 | Tox | 0.82 | 0.61 | 0.53 | Tox |
| Respiration | Ionophore | Gallic acid | 0.96 | 0.96 | 0.87 | Tox | 0.90 | 2.15 | 1.00 | Tox | 1.04 | 1.17 | 0.72 | Tox |
| | | 3,5-Dinitro-benzene | 0.97 | 1.31 | Tox | Tox | 0.98 | 1.07 | Tox | Tox | 0.69 | 0.97 | Tox | Tox |
| | | FCCP | 0.80 | 0.43 | 0.52 | 1.09 | 0.89 | 0.75 | 0.83 | 1.07 | 1.69 | 1.45 | 1.07 | 0.98 |
| | | Sodium caprylate | 0.81 | 0.78 | Tox | Tox | 0.86 | 1.04 | Tox | Tox | 1.38 | 0.85 | Tox | Tox |
| | | Cimamic acid | 0.90 | 1.06 | 0.73 | Tox | 0.88 | 0.93 | 0.99 | Tox | 0.88 | 0.92 | 1.17 | Tox |
| | | 2,4-Dintrophenol | 0.72 | 0.80 | 0.86 | Tox | 0.91 | 0.83 | 1.02 | Tox | 1.10 | 1.04 | 1.04 | Tox |
| | | Sorbic acid | 0.66 | 0.71 | 0.62 | 0.98 | 0.98 | 0.98 | 0.86 | 0.98 | 0.74 | 0.82 | 0.31 | 0.28 |
| | | Pentachloro-phenol | 0.72 | 0.59 | 0.74 | 0.48 | 0.81 | 0.82 | 0.79 | 0.52 | 0.70 | 0.68 | 0.83 | 0.32 |
| | | 18-Crown-6 ether | 0.70 | 0.67 | 0.63 | 0.64 | 0.87 | 0.62 | 0.74 | 0.51 | 0.69 | 0.98 | 0.79 | 0.11 |
| | | CCCP | 0.79 | 0.62 | 0.70 | Tox | 0.83 | 0.83 | 0.69 | Tox | 0.32 | 0.31 | 0.38 | Tox |
| | Other | Iodonitro Tetrazolium Violet | 0.92 | 0.71 | 1.50 | 1.17 | 0.85 | 0.92 | 1.44 | 1.10 | 1.46 | 1.58 | 1.61 | 1.31 |
| | | Oxycarboxin | 1.04 | Tox | Tox | Tox | 0.92 | Tox | Tox | Tox | 0.56 | Tox | Tox | Tox |
| | | Ruthenium red | 0.78 | 0.79 | 0.75 | 0.69 | 0.87 | 0.89 | 0.83 | 0.34 | 0.68 | 0.34 | 0.38 | 0.19 |
| | Uncoupler | Crystal violet | 0.98 | 1.13 | 1.10 | 1.18 | 1.03 | 1.11 | 1.08 | 1.23 | 1.17 | 1.17 | 1.41 | 1.62 |
| | | Menadione | 1.10 | 0.98 | 0.82 | 0.68 | 1.07 | 1.00 | 1.03 | 0.84 | 1.31 | 1.30 | 1.50 | 0.83 |
| | | Sodium azide | 0.97 | Tox | Tox | Tox | 1.01 | Tox | Tox | Tox | 0.93 | Tox | Tox | Tox |
| | | Tetrazolium violet | 0.99 | 1.34 | Tox | Tox | 0.83 | 0.53 | Tox | Tox | 0.35 | 0.58 | Tox | Tox |
| Wall | β-lactam | Phenethicillin | 0.99 | Tox | Tox | Tox | 1.07 | Tox | Tox | Tox | 1.66 | Tox | Tox | Tox |
| | | Cloxacillin | 1.03 | 1.45 | Tox | Tox | 1.09 | 1.21 | Tox | Tox | 0.98 | 1.03 | Tox | Tox |
| | | Piperacillin | 1.11 | 1.18 | Tox | Tox | 0.91 | 1.08 | Tox | Tox | 1.11 | 0.94 | Tox | Tox |
| | | Nafcillin | 0.88 | 1.30 | Tox | Tox | 0.99 | 1.17 | Tox | Tox | 0.80 | 1.06 | Tox | Tox |
| | | Penicillin G | 0.89 | 0.99 | Tox | Tox | 0.95 | 0.88 | Tox | Tox | 1.04 | 1.28 | Tox | Tox |
| | | Aziocillin | 0.90 | 1.07 | 1.12 | Tox | 0.97 | 0.90 | 1.14 | Tox | 1.03 | 1.08 | 0.70 | Tox |
| | | Ampicillin | 0.91 | 1.03 | 1.09 | 1.03 | 0.92 | 0.89 | 0.91 | 0.91 | 1.14 | 0.94 | 0.98 | 1.13 |
| | | Amoxicillin | 0.81 | 1.02 | Tox | Tox | 0.88 | 0.98 | Tox | Tox | 1.06 | 1.00 | Tox | Tox |
| | | Carbenicillin | 0.88 | 0.94 | Tox | Tox | 0.98 | 1.01 | Tox | Tox | 1.01 | 0.84 | Tox | Tox |
| | | Carbenicillin | 0.95 | 0.66 | 0.61 | Tox | 0.92 | 0.83 | 0.52 | Tox | 0.89 | 0.90 | 0.95 | Tox |
| | | Oxacillin | 0.88 | 1.05 | Tox | Tox | 0.89 | 0.56 | Tox | Tox | 1.03 | 0.25 | Tox | Tox |
| | Cephalosporin | Cefamandole nafate | 0.87 | 0.92 | 1.00 | 1.66 | 0.99 | 1.14 | 0.96 | 1.64 | 1.25 | 1.20 | 1.10 | 1.53 |
| | | Cefsulodin | 0.81 | 0.90 | 0.87 | 1.46 | 0.98 | 1.00 | 0.99 | 1.11 | 1.14 | 1.43 | 1.44 | 1.92 |
| | | Cefoxitin | 0.94 | 0.98 | 0.93 | 1.06 | 0.99 | 0.98 | 1.03 | 1.13 | 1.04 | 1.07 | 1.33 | 1.36 |
| | | Cefuroxime | 0.99 | 1.12 | Tox | Tox | 0.97 | 0.87 | Tox | Tox | 1.10 | 1.17 | Tox | Tox |
| | | Cefoperazone | 0.91 | 1.08 | 0.96 | Tox | 0.95 | 0.69 | 0.79 | Tox | 0.9 | 50.95 | 1.49 | Tox |
| | | Cephalothin | 0.82 | 0.93 | 0.88 | Tox | 0.96 | 1.03 | 1.14 | Tox | 1.14 | 1.22 | 0.42 | Tox |
| | | Moxalactam | 0.90 | 0.88 | 0.82 | 0.75 | 0.97 | 0.96 | 0.96 | 0.93 | 1.07 | 1.08 | 0.96 | 0.91 |
| | | Ceftriaxone | 0.86 | 0.70 | Tox | Tox | 0.99 | 0.84 | Tox | Tox | 1.19 | 0.93 | Tox | Tox |
| | | Cefazolin | 0.84 | 0.97 | Tox | Tox | 0.90 | 0.92 | Tox | Tox | 0.61 | 1.05 | Tox | Tox |
| | | Cefmetazole | 0.84 | 0.74 | Tox | Tox | 0.85 | 0.89 | Tox | Tox | 0.73 | 0.80 | Tox | Tox |
| | | Cefotaxime | 1.07 | Tox | Tox | Tox | 0.91 | Tox | Tox | Tox | 0.18 | Tox | Tox | Tox |

TABLE 5-continued

| Drug Class | | Chemical | | | | | | | | | | | | |
|---|---|---|---|---|---|---|---|---|---|---|---|---|---|---|
| | Other | Aztreonam | 0.87 | 1.19 | 2.90 | Tox | 0.87 | 1.15 | 1.93 | Tox | 1.00 | 1.27 | 2.26 | Tox |
| | | Phosphomycin | 0.92 | 1.01 | Tox | Tox | 0.86 | 0.37 | Tox | Tox | 0.26 | 0.01 | Tox | Tox |
| | Peptidoglycan synthesis | D-Serine | 0.90 | 1.11 | 1.03 | Tox | 0.91 | 0.90 | 0.81 | Tox | 0.71 | 0.95 | 0.97 | Tox |
| | | D-Cycloserine | 0.70 | 1.08 | Tox | Tox | 0.99 | 0.81 | Tox | Tox | 0.93 | 0.90 | Tox | Tox |
| | | Glycine | 0.98 | 0.95 | 1.08 | 0.96 | 0.98 | 0.92 | 0.88 | 0.77 | 1.03 | 0.79 | 0.65 | 0.65 |
| | Polymyxin | Polymyxin B | 1.37 | Tox | Tox | Tox | 1.23 | Tox | Tox | Tox | 1.59 | Tox | Tox | Tox |
| | | Colistin | 0.95 | 0.75 | Tox | Tox | 0.97 | 0.24 | Tox | Tox | 0.84 | 0.08 | Tox | Tox |
| | | Polymyxin B | 0.79 | 0.75 | 0.26 | Tox | 0.85 | 0.83 | 0.05 | Tox | 0.40 | 0.35 | 0.01 | Tox |

| | | | Copper (mM) | | | | | | | | | | | |
|---|---|---|---|---|---|---|---|---|---|---|---|---|---|---|
| Drug Class | | Chemical | 0.1 | | | | 0.5 | | | | 1.0 | | | |
| Chelator | Carboxylic acid | EGTA | 1.05 | 1.25 | 1.28 | 1.06 | 0.87 | 1.02 | 1.06 | 1.04 | 0.94 | 1.30 | 1.59 | 1.44 |
| | | Fusaric acid | 0.73 | 1.37 | Tox | Tox | 0.28 | 1.20 | Tox | Tox | 0.38 | 2.34 | Tox | Tox |
| | | EDTA | 1.02 | 1.02 | 1.17 | 1.47 | 0.92 | 0.99 | 1.14 | 1.74 | 1.01 | 1.47 | 1.68 | 2.09 |
| | Hydroxyquinoline | 5,7-Dichloro-8-hydroxyquinoline | 1.15 | 1.14 | 1.43 | Tox | 0.91 | 0.74 | 1.17 | Tox | 0.93 | 0.66 | 0.73 | Tox |
| | | 8-Hydroxyquinoline | 0.90 | 0.95 | 1.40 | Tox | 0.74 | 0.69 | 0.98 | Tox | 0.66 | 0.70 | 1.08 | Tox |
| | | 5,7-Dichloro-8-hydroxyquinaldine | 0.90 | 1.03 | 1.48 | 2.10 | 0.66 | 0.87 | 1.53 | 2.83 | 0.62 | 0.70 | 1.00 | 1.73 |
| | | 5-Chloro-7-iodo-8-hydroxyquinoline | 1.47 | 1.60 | 1.56 | 1.35 | 1.30 | 1.79 | 1.57 | 1.57 | 0.91 | 1.10 | 1.22 | 1.80 |
| | Other | 2,2'-Dipyridyl | 0.76 | Tox | Tox | Tox | 0.61 | Tox | Tox | Tox | 0.76 | Tox | Tox | Tox |
| | | 1,10-Phenanthroline | 0.82 | 1.13 | Tox | Tox | 0.51 | 0.75 | Tox | Tox | 0.49 | 0.73 | Tox | Tox |
| | | Sodium pyrophosphate decahydrate | 1.09 | 0.93 | 1.00 | 1.09 | 0.86 | 0.88 | 1.00 | 1.03 | 0.69 | 0.69 | 1.07 | 1.24 |
| DNA & RNA | DNA Alkylation | 5-Azacytidine | 1.03 | 1.11 | 1.02 | 0.99 | 0.86 | 1.00 | 1.00 | 0.94 | 0.56 | 0.62 | 0.59 | 0.59 |
| | | Chlorambucil | 1.65 | 1.28 | 1.50 | 1.02 | 1.01 | 0.94 | 1.45 | 1.09 | 1.15 | 0.98 | 1.02 | 0.73 |
| | Fluoroquinolone | Enoxacin | 0.91 | 1.08 | Tox | Tox | 0.84 | Tox | Tox | Tox | 0.59 | 0.86 | Tox | Tox |
| | | Ciprofloxacin | 1.03 | 1.02 | 1.25 | Tox | 0.91 | 0.99 | Tox | Tox | 0.51 | 0.68 | 1.18 | Tox |
| | | Lomefloxacin | 1.05 | 0.97 | 1.46 | Tox | 0.88 | 0.90 | Tox | Tox | 0.70 | 0.64 | 2.08 | Tox |
| | | Norfloxacin | 1.18 | 1.08 | 1.07 | Tox | 1.00 | 0.89 | 1.60 | Tox | 1.01 | 0.70 | 1.12 | Tox |
| | | Ofloxacin | 0.89 | 0.90 | 0.88 | Tox | 0.86 | 0.84 | 1.18 | Tox | 0.77 | 0.80 | 0.89 | Tox |
| | Intercalator | 2-Phenylphenol | 1.05 | 1.12 | 0.92 | Tox | 0.73 | 0.56 | 0.37 | Tox | 0.60 | 0.56 | 0.46 | Tox |
| | | Umbelliferone | 1.04 | 0.94 | 0.73 | 1.26 | 0.74 | 0.82 | 0.82 | 1.28 | 0.65 | 0.75 | 1.22 | 1.72 |
| | | Coumarin | 0.94 | 0.93 | 0.92 | Tox | 0.82 | 0.77 | 0.85 | Tox | 0.62 | 0.56 | 0.64 | Tox |
| | | Proflavine | 0.96 | 1.04 | 1.03 | 1.21 | 0.88 | 0.92 | 0.92 | 1.33 | 0.91 | 0.80 | 0.76 | 0.95 |
| | | 4-Hydroxy-coumarin | 0.92 | 0.75 | 0.00 | Tox | 0.96 | 0.89 | 0.37 | 1.03 | 0.86 | 0.72 | 0.44 | Tox |
| | | Novobiocin | 1.01 | 1.07 | 0.99 | 1.06 | 0.71 | 0.55 | 0.79 | 1.08 | 0.53 | 0.59 | 1.17 | 1.80 |
| | | 9-Aminoacridine | 1.10 | 1.22 | 1.08 | 1.04 | 0.93 | 0.95 | 1.00 | Tox | 0.99 | 0.94 | 0.80 | 0.78 |
| | | Acriflavine | 1.00 | 1.03 | 0.95 | 1.04 | 0.88 | 0.91 | 0.95 | 1.04 | 0.89 | 0.82 | 0.81 | 0.78 |
| | Nitrofuran analog | Furaltadone | 0.96 | 0.98 | Tox | Tox | 0.88 | 0.86 | Tox | Tox | 0.71 | 0.68 | Tox | Tox |
| | | Nitrofurantoin | 0.99 | 1.01 | 1.05 | Tox | 0.74 | 0.77 | 0.82 | Tox | 0.62 | 0.57 | 0.62 | Tox |
| | | 5-nitro-2-furaldehyde semicarbazone | 0.86 | 0.77 | Tox | Tox | 0.83 | 0.71 | Tox | Tox | 0.83 | 0.74 | Tox | Tox |
| | Other | Hydroxylamine | 0.98 | 0.99 | 0.94 | 1.40 | 0.80 | 0.79 | 0.68 | 0.90 | 0.74 | 0.70 | 0.75 | 1.22 |
| | | Hexammine cobalt (III) chloride | 1.06 | 1.17 | 1.19 | 1.51 | 0.93 | 1.05 | 1.05 | 1.59 | 0.94 | 0.90 | 0.73 | 0.87 |
| | | Disulphiram | 1.07 | 1.03 | 1.08 | 2.30 | 0.94 | 0.76 | 0.75 | Tox | 0.75 | 0.45 | 0.41 | 0.90 |
| | | Myricetin | 1.04 | 0.88 | 0.95 | 0.90 | 0.41 | 0.42 | 0.76 | 0.77 | 0.45 | 0.47 | 0.61 | 0.76 |
| | Purine analog | 6-Mercapto-purine | 1.00 | 1.00 | 0.71 | 1.65 | 1.27 | 0.98 | 0.79 | 1.86 | 1.41 | 1.53 | 1.65 | 3.52 |
| | | Azathioprine | 0.96 | 0.96 | 1.15 | 1.26 | 0.85 | 1.00 | 1.22 | 1.50 | 0.45 | 0.82 | 1.07 | 1.79 |
| | Pyrimidine analog | 5-fluoro-5'-deoxyuridine | 1.07 | 1.20 | 1.20 | 1.06 | 0.88 | 0.95 | 0.88 | 0.89 | 0.79 | 0.80 | 0.72 | 0.63 |
| | | Trifluorothymidine | 1.14 | 1.18 | 1.06 | 1.08 | 1.10 | 1.02 | 0.99 | 0.98 | 0.90 | 0.76 | 0.61 | 0.62 |
| | | Cytosine-1-β-D-arabinofuranoside | 1.04 | 1.10 | 1.11 | 1.19 | 0.99 | 0.95 | 0.96 | 0.89 | 1.02 | 0.94 | 0.98 | 1.03 |
| | | 5-Fluorouracil | 0.98 | 0.85 | Tox | Tox | 0.65 | 0.71 | Tox | Tox | 0.61 | 0.57 | Tox | Tox |
| | | 5-Fluoroorotic acid | 0.91 | 0.97 | 0.97 | 0.99 | 0.73 | 0.77 | 0.81 | 0.85 | 0.56 | 0.61 | 0.66 | 0.81 |
| | Quinolone | Cinoxacin | 1.02 | 1.06 | Tox | Tox | 0.93 | 0.92 | Tox | Tox | 0.64 | 0.68 | Tox | Tox |
| | | Pipemidic Acid | 1.03 | 1.03 | Tox | Tox | 0.83 | 0.86 | Tox | Tox | 0.55 | 0.55 | Tox | Tox |
| | | Nalidixic Acid | 0.86 | 0.83 | Tox | Tox | 0.76 | 0.83 | Tox | Tox | 0.59 | 0.59 | Tox | Tox |
| | | Oxolinic acid | 0.90 | 0.93 | 0.87 | 0.92 | 0.53 | 0.64 | 0.74 | 0.83 | 0.52 | 0.53 | 0.56 | 0.72 |
| Folate | Other | 2,4-Diamino-6,7-diisopropylpteridine | 1.12 | 0.94 | 1.01 | Tox | 0.89 | 0.97 | 1.14 | Tox | 0.83 | 0.64 | 0.72 | Tox |
| | | Hydroxyurea | 1.17 | 1.24 | 1.08 | Tox | 1.20 | 1.69 | 1.53 | Tox | 1.41 | 1.87 | 0.80 | Tox |
| | | Trimethoprim | 0.95 | 1.51 | Tox | Tox | 0.86 | 1.37 | Tox | Tox | 0.63 | 1.03 | Tox | Tox |
| | Sulfonamide | Sulfanilamide | 0.96 | 0.95 | 0.93 | 0.94 | 1.00 | 0.90 | 0.84 | 1.30 | 0.61 | 0.61 | 0.58 | 0.59 |
| | | Sulfamethoxazole | 0.95 | 1.22 | 0.95 | 0.96 | 0.77 | 0.84 | 0.84 | 1.00 | 0.58 | 0.74 | 0.60 | 0.70 |
| | | Sulfamethazine | 0.94 | 1.08 | 0.92 | 0.94 | 0.77 | 0.86 | 0.79 | 0.95 | 0.54 | 0.59 | 0.56 | 0.58 |
| | | Sulfathiazole | 0.98 | 1.08 | 0.88 | 0.93 | 0.80 | 0.80 | 0.82 | 1.35 | 0.61 | 0.65 | 0.57 | 0.67 |
| | | Sulfadiazine | 0.92 | 1.09 | 0.89 | 0.98 | 0.78 | 0.80 | 0.88 | 1.70 | 0.56 | 0.66 | 0.56 | 0.74 |
| | | Sulfachloro-pyridazine | 1.03 | 1.08 | 0.93 | 0.72 | 0.81 | 0.78 | 0.76 | 0.93 | 0.78 | 0.68 | 0.69 | 0.76 |
| | | Sulfisoxazole | 0.98 | 0.95 | 0.85 | 0.87 | 0.85 | 1.44 | 2.60 | Tox | 0.49 | 0.48 | 0.86 | 1.71 |
| | | Sulfamono-methoxine | 0.97 | 1.06 | 0.85 | 0.73 | 0.70 | 0.74 | 0.81 | 1.06 | 0.73 | 0.73 | 0.74 | 0.89 |

TABLE 5-continued

| | | | | | | | | | | | | | | |
|---|---|---|---|---|---|---|---|---|---|---|---|---|---|---|
| Membrane | Cationic detergent | Methyltrioctyl NH4+ Br– | 1.05 | 1.22 | 1.39 | Tox | 1.08 | 1.14 | 1.05 | Tox | 0.87 | 0.80 | 0.44 | Tox |
| | | Poly-L-lysine | 1.15 | 0.95 | Tox | Tox | 1.03 | 0.96 | Tox | Tox | 1.01 | 0.59 | Tox | Tox |
| | | Domiphen bromide | 0.94 | 1.03 | Tox | Tox | 0.75 | 0.77 | Tox | Tox | 0.68 | 0.66 | Tox | Tox |
| | | Cetylpyridinium chloride | 1.02 | 0.99 | 1.17 | Tox | 0.84 | 0.97 | Tox | Tox | 0.62 | 0.62 | 3.06 | Tox |
| | | Dodecyltrimethyl NH$_4^+$ Br$^-$ | 1.20 | 1.17 | 1.51 | Tox | 1.02 | 1.04 | Tox | Tox | 0.77 | 0.73 | 1.63 | Tox |
| | | Benzethonium chloride | 0.94 | 0.99 | Tox | Tox | 0.68 | 0.51 | Tox | Tox | 0.45 | 0.31 | Tox | Tox |
| | Electron transport | Chlorhexidine | 1.06 | 1.14 | 1.20 | Tox | 1.05 | 0.86 | 0.90 | Tox | 0.98 | 0.71 | 0.69 | Tox |
| | | Hexa-chlorophene | 0.95 | 0.99 | 1.05 | 1.03 | 0.83 | 0.82 | 0.80 | 0.90 | 0.59 | 0.60 | 0.63 | 0.97 |
| | | Alexidine | 0.98 | 1.00 | Tox | Tox | 0.86 | 0.69 | Tox | Tox | 1.04 | 0.90 | Tox | Tox |
| | Guanidine | Dodine | 0.90 | 1.04 | 2.73 | Tox | 0.83 | 0.94 | Tox | Tox | 0.58 | 0.50 | 1.33 | Tox |
| | | Guanidine hydrochloride | 0.94 | 0.92 | 0.78 | Tox | 0.82 | 0.78 | 0.44 | Tox | 0.82 | 0.77 | 0.53 | Tox |
| | Other | Protamine sulfate | 0.79 | Tox | Tox | Tox | 1.09 | 1.26 | Tox | Tox | 0.56 | Tox | Tox | Tox |
| | | 1-Hydroxy-pyridine-2-thione | 1.03 | 1.06 | Tox | Tox | 0.81 | 0.72 | Tox | Tox | 0.56 | 0.50 | Tox | Tox |
| | | Amitriptyline | 1.06 | 1.20 | 0.72 | Tox | 0.85 | 1.10 | Tox | Tox | 0.92 | 0.96 | 0.90 | Tox |
| | | Niaproof | 1.26 | 1.45 | 0.74 | 0.91 | 1.09 | 1.20 | 0.43 | 0.46 | 1.19 | 1.00 | 0.73 | 1.32 |
| | | Lauryl sulfobetaine | 0.96 | 1.18 | 0.80 | 0.21 | 0.60 | 1.39 | 0.72 | 0.48 | 0.48 | 0.80 | 0.34 | 0.07 |
| | Phenothiazine | Promethazine | 1.10 | 1.21 | 1.04 | Tox | 1.07 | 1.27 | Tox | Tox | 0.90 | 1.07 | 1.33 | Tox |
| | | Chlorpromazine | 1.00 | 1.02 | 0.70 | Tox | 0.82 | 0.88 | Tox | Tox | 0.71 | 0.64 | 0.64 | Tox |
| | | Thioridazine | 1.02 | 0.68 | 1.42 | Tox | 0.78 | 0.81 | 0.77 | Tox | 0.62 | 0.70 | 1.07 | Tox |
| | | Trifluoperazine | 1.07 | 1.08 | 0.61 | 0.81 | 0.85 | 0.69 | 0.55 | 0.51 | 0.65 | 0.50 | 0.45 | 0.41 |
| Other biocide | Anti-capsule | Sodium salicylate | 0.85 | Tox | Tox | Tox | 1.11 | Tox | Tox | Tox | 0.43 | Tox | Tox | Tox |
| | | Thiosalicylic acid | 0.96 | 1.07 | 0.71 | 1.07 | 0.90 | 0.82 | 0.72 | 0.77 | 0.83 | 0.75 | 0.52 | 0.67 |
| | | Ketoprofen | 0.95 | 0.98 | 0.87 | Tox | 1.02 | 0.96 | 0.67 | Tox | 0.87 | 0.66 | 0.32 | Tox |
| | Acetylcholine antagonist | Pridinol | 0.81 | 1.00 | 1.54 | Tox | 0.90 | 1.54 | 1.37 | Tox | 0.75 | 1.05 | 0.33 | Tox |
| | | Atropine | 0.92 | 1.00 | Tox | Tox | 0.81 | 0.96 | Tox | Tox | 0.64 | 0.69 | Tox | Tox |
| | | Orphenadrine | 1.03 | 0.87 | Tox | Tox | 0.87 | 1.47 | Tox | Tox | 0.95 | 0.76 | Tox | Tox |
| | Glycopeptide | Phleomycin | 0.99 | 1.27 | Tox | Tox | 1.09 | 1.19 | Tox | Tox | 0.99 | 0.96 | Tox | Tox |
| | | Vancomycin | 0.96 | 1.18 | 1.21 | Tox | 0.76 | 0.94 | Tox | Tox | 0.52 | 0.57 | 0.51 | Tox |
| | | Bleomycin | 1.06 | 0.97 | 1.17 | Tox | 0.92 | 0.93 | Tox | Tox | 0.89 | 0.62 | 0.70 | Tox |
| | Fungicide | Nordihydroguaiaretic acid | 0.90 | 0.99 | 1.60 | 0.84 | 0.64 | 0.66 | 0.83 | 0.60 | 0.55 | 0.50 | 0.90 | 0.69 |
| | | Chloroxylenol | 1.16 | 1.30 | 1.11 | 0.76 | 0.98 | Tox | Tox | Tox | 0.84 | 0.99 | 0.82 | 0.76 |
| | Phenylsulfamide | Tolylfluanid | 0.79 | 0.82 | 0.87 | 0.79 | 0.80 | 0.80 | 0.63 | 0.59 | 0.84 | 0.78 | 0.68 | 0.54 |
| | | Dichlofluanid | 0.79 | 0.82 | 0.70 | Tox | Tox | 0.50 | 0.46 | Tox | 0.32 | 0.27 | 0.27 | Tox |
| | Ion (K+) blocker | 4-Aminopyridine | 1.16 | 1.14 | 0.95 | 0.97 | 0.86 | 0.87 | 0.81 | 1.01 | 1.10 | 0.88 | 0.81 | 0.72 |
| | | Dequalinium chloride | 0.87 | 0.82 | 0.80 | 0.79 | 0.82 | 0.71 | 0.58 | 0.55 | 0.56 | 0.60 | 0.61 | 0.65 |
| | Ion (Na+) blocker | Procaine | 1.03 | 1.07 | 1.06 | 0.96 | 0.87 | 0.95 | 1.06 | 0.91 | 0.96 | 0.94 | 0.97 | 1.04 |
| | | Lidocaine | 0.42 | 0.52 | 1.25 | Tox | 0.38 | 0.42 | Tox | Tox | 0.29 | 0.32 | 0.98 | Tox |
| | Nitroimidazole | Tinidazole | 1.05 | 0.98 | 1.11 | Tox | 0.64 | 0.54 | 0.88 | Tox | 0.66 | 0.65 | 0.71 | Tox |
| | | 2-Nitroimidazole | 0.97 | 1.15 | Tox | Tox | 0.79 | 0.76 | Tox | Tox | 1.01 | 1.09 | Tox | Tox |
| | | Ornidazole | 0.94 | 0.83 | 0.82 | Tox | 0.79 | 0.56 | 0.43 | Tox | 0.64 | 0.44 | 0.42 | Tox |
| | Other | Tannic acid | 0.93 | 0.91 | 1.12 | 1.07 | 0.88 | 1.39 | 0.73 | 1.17 | 1.08 | 1.69 | 1.68 | 2.14 |
| | | Semicarbazide | 1.12 | 1.29 | 0.96 | 0.91 | 0.98 | 1.22 | 1.17 | Tox | 0.79 | 0.83 | 0.63 | 0.36 |
| | | Captan | 0.88 | 0.79 | 0.77 | 0.93 | 0.61 | 0.52 | 0.47 | 1.14 | 0.55 | 0.53 | 0.46 | 0.62 |
| | | Ethionamide | 1.04 | 1.28 | 0.90 | 0.59 | 1.03 | 0.89 | 1.14 | 1.12 | 0.93 | 1.09 | 1.61 | 1.03 |
| | | D,L-Propranolol | 1.01 | 0.99 | Tox | Tox | 0.82 | 0.91 | Tox | Tox | 0.67 | 0.74 | Tox | Tox |
| | | Compound 48/80 | 1.08 | 1.25 | 1.17 | Tox | 0.94 | 1.02 | 1.49 | Tox | 0.78 | 0.76 | 0.96 | Tox |
| | | Chelerythrine | 1.27 | 1.15 | 1.07 | 1.29 | 1.01 | 1.02 | 1.29 | 1.89 | 1.00 | 0.81 | 1.06 | 1.71 |
| | | Sanguinarine | 0.84 | 0.93 | 0.83 | Tox | 0.79 | 0.96 | Tox | Tox | 0.66 | 0.88 | 1.36 | Tox |
| | | Patulin | Tox | Tox | Tox | Tox | Tox | Tox | Tox | Tox | Tox | Tox | Tox | Tox |
| | Rifamycin | Rifampicin | 1.10 | 1.33 | 0.97 | Tox | 0.97 | 0.99 | 1.42 | Tox | 0.82 | 0.96 | 0.46 | Tox |
| | | Rifamycin SV | 1.05 | 1.07 | 1.88 | 1.24 | 0.74 | 0.73 | 0.67 | 1.02 | 0.29 | 0.26 | 0.28 | 1.22 |
| | Triazole | Guanazole | 1.04 | 0.81 | Tox | Tox | 0.60 | 0.50 | Tox | Tox | 0.63 | 0.58 | Tox | Tox |
| | | 3-Amino-1,2,4-triazole | 0.97 | 0.94 | 1.65 | Tox | 0.63 | 0.62 | 0.63 | 0.54 | 0.48 | 0.51 | 1.41 | Tox |
| | Oxidizing agent | Diamide | 1.02 | 0.98 | 0.96 | 0.99 | 0.78 | 0.72 | Tox | Tox | 0.52 | 0.51 | 0.52 | 0.56 |
| | | 1-Chloro-2,4-dinitrobenzene | 1.21 | 1.04 | 1.02 | Tox | 0.92 | 0.83 | 0.66 | Tox | 0.71 | 0.54 | 0.48 | Tox |
| | | D,L-Thioctic Acid | 1.28 | 1.24 | 0.80 | Tox | 0.46 | 0.34 | 0.72 | Tox | 0.33 | 0.62 | 0.67 | Tox |
| | | Lawsone | 0.38 | 0.45 | 0.44 | 0.87 | 0.18 | 0.12 | 0.14 | 0.93 | 0.13 | 0.13 | 0.31 | 1.23 |
| | | Plumbagin | 0.83 | 0.80 | 0.67 | 0.66 | 0.36 | 0.38 | 0.32 | 0.25 | 0.37 | 0.35 | 0.30 | 0.26 |
| | | 3,4-Dimethoxybenzyl alcohol | 1.30 | 0.72 | 0.93 | Tox | 1.03 | 0.99 | 0.61 | Tox | 1.10 | 1.37 | 2.00 | Tox |
| | | Methyl viologen | 0.85 | 0.99 | Tox | Tox | 0.63 | 0.77 | Tox | Tox | 0.61 | 0.64 | Tox | Tox |
| | | Iodoacetate | 0.62 | Tox | Tox | Tox | 0.51 | Tox | 0.67 | Tox | 0.07 | Tox | Tox | Tox |
| | Aminoglycoside | Dihydro-streptomycin | 1.10 | 0.98 | 0.97 | 0.53 | 0.92 | 0.89 | Tox | Tox | 0.80 | 0.67 | 0.53 | 0.41 |
| | | Hygromycin B | 1.19 | 1.12 | 0.89 | 0.61 | 0.80 | 0.81 | 1.02 | Tox | 0.91 | 0.79 | 0.77 | 0.94 |
| | | Gentamicin | 0.89 | 0.87 | 0.79 | 0.86 | 0.78 | 0.80 | 0.74 | 1.54 | 0.61 | 0.59 | 0.58 | 0.61 |
| | | Sisomicin | 0.88 | 1.02 | 0.97 | 0.99 | 0.84 | 0.87 | 0.82 | 0.81 | 0.86 | 0.62 | 0.59 | 0.53 |
| | | Neomycin | 0.86 | 0.88 | 0.84 | 0.97 | 0.79 | 0.79 | 0.79 | Tox | 0.59 | 0.61 | 0.59 | 0.78 |
| | | Spectinomycin | 0.97 | 1.01 | 0.99 | 1.04 | 0.94 | 0.96 | 0.92 | Tox | 0.84 | 0.71 | 0.66 | 0.81 |
| | | Geneticin (G418) | 0.97 | 0.87 | 0.86 | 0.88 | 0.73 | 0.71 | 0.71 | Tox | 0.54 | 0.50 | 0.48 | 0.44 |
| | | Tobramycin | 0.92 | 1.02 | 0.96 | 1.01 | 0.98 | 0.92 | 0.98 | Tox | 0.83 | 0.66 | 0.56 | 0.57 |
| | | Paromomycin | 0.98 | 1.00 | 0.93 | 0.84 | 0.86 | 0.81 | 1.43 | Tox | 0.86 | 0.63 | 0.53 | 0.44 |

TABLE 5-continued

| | | | | | | | | | | | | | | | |
|---|---|---|---|---|---|---|---|---|---|---|---|---|---|---|---|
| | | Amikacin | 1.01 | 0.96 | 1.04 | 0.89 | 0.94 | 0.85 | 1.51 | Tox | 0.95 | 0.80 | 0.80 | 0.52 |
| | | Kanamycin | 0.89 | 0.90 | 0.91 | 0.85 | 0.90 | 0.91 | 1.13 | Tox | 0.76 | 0.77 | 0.77 | 0.67 |
| | | Apramycin | 1.07 | 1.02 | 0.89 | 0.88 | 0.89 | 0.85 | 0.93 | Tox | 0.74 | 0.69 | 0.59 | 0.57 |
| | | Capreomycin | 1.10 | 0.91 | 0.83 | 0.87 | 0.87 | 0.86 | 0.90 | Tox | 0.86 | 0.57 | 0.49 | 0.60 |
| | | Streptomycin | 1.22 | 1.22 | 1.16 | 1.16 | 1.47 | Tox | Tox | Tox | 0.89 | 0.80 | 0.64 | 0.53 |
| Protein | Macrolide | Josamycin | 0.96 | 1.20 | 1.17 | Tox | 0.96 | 0.75 | 1.60 | Tox | 0.70 | 0.71 | 0.69 | Tox |
| | | Spiramycin | 1.00 | 1.05 | 0.94 | Tox | 0.89 | Tox | Tox | Tox | 0.92 | 0.91 | 3.40 | Tox |
| | | Erythromycin | 0.91 | 0.91 | 0.86 | 0.85 | 0.79 | 0.77 | 0.85 | Tox | 0.64 | 0.61 | 0.66 | 0.73 |
| | | Oleandomycin | 1.01 | 0.89 | 0.97 | Tox | 0.78 | 0.73 | 0.91 | Tox | 0.86 | 0.64 | 0.44 | Tox |
| | | Tylosin | 1.10 | 0.98 | 0.93 | Tox | 0.76 | 0.73 | 2.02 | Tox | 0.86 | 0.86 | 0.98 | Tox |
| | | Troleandomycin | 0.90 | 1.13 | 2.39 | Tox | 0.89 | 1.29 | Tox | Tox | 0.75 | 0.93 | 2.93 | Tox |
| | Other | PMSF | 0.76 | 0.71 | 0.62 | 0.71 | 0.59 | 0.58 | 0.37 | 0.46 | 0.41 | 0.42 | 0.34 | 0.38 |
| | | Benserazide | 1.03 | 1.08 | 2.60 | 1.48 | 0.88 | 0.99 | 4.18 | 2.77 | 0.66 | 0.92 | 3.79 | 4.01 |
| | | B-Chloro-L-alanine HCl | 1.31 | 1.09 | 1.07 | 1.00 | 1.07 | 1.38 | 2.23 | Tox | 1.29 | 1.26 | 1.47 | 1.58 |
| | | Lincomycin | 0.91 | 0.93 | 1.10 | Tox | 0.83 | 1.05 | Tox | Tox | 0.73 | 0.72 | 0.92 | Tox |
| | Protein synthesis | Fusidic acid | 0.71 | 0.77 | Tox | Tox | 0.68 | 0.07 | Tox | 1.07 | 0.75 | 0.15 | Tox | Tox |
| | | Blasticidin S | 1.05 | 1.14 | 0.95 | Tox | 0.90 | 0.96 | Tox | Tox | 0.71 | 0.65 | 0.49 | Tox |
| | | Chloramphenicol | 1.05 | 0.73 | Tox | Tox | 1.03 | 1.92 | Tox | Tox | 0.74 | 0.56 | Tox | Tox |
| | | Puromycin | 0.88 | 0.90 | 2.22 | Tox | 0.52 | 0.52 | 2.57 | Tox | 0.47 | 0.56 | 1.79 | Tox |
| | | Chloramphenicol | 1.06 | 0.86 | 0.64 | Tox | 0.89 | 1.16 | Tox | Tox | 0.88 | 0.65 | 0.92 | Tox |
| | | Thiamphenicol | 0.98 | 0.99 | 1.17 | Tox | 0.55 | 0.76 | 1.64 | Tox | 0.46 | 0.48 | 0.68 | Tox |
| | Tetracycline | Doxycycline | 0.98 | 1.44 | Tox | Tox | 0.96 | 1.26 | Tox | Tox | 0.64 | 2.32 | Tox | Tox |
| | | Chlortetracycline | 1.01 | 2.82 | Tox | Tox | 0.83 | 1.67 | Tox | Tox | 0.76 | 3.28 | Tox | Tox |
| | | Oxytetracycline | 0.88 | 0.83 | 0.83 | 1.10 | 0.78 | 0.77 | 0.74 | 0.79 | 0.64 | 0.62 | 0.55 | 0.62 |
| | | Tetracycline | 0.92 | 1.05 | 0.92 | 0.87 | 0.93 | 0.94 | 0.96 | 0.89 | 0.70 | 0.81 | 0.65 | 1.09 |
| | | Demeclocycline | 0.95 | 0.91 | Tox | Tox | 0.89 | 1.00 | 0.36 | Tox | 0.59 | 0.56 | Tox | Tox |
| | | Minocycline | 1.01 | 0.84 | Tox | Tox | 0.89 | 1.10 | Tox | Tox | 0.68 | 0.64 | Tox | Tox |
| | | Penimepicycline | 0.91 | 1.07 | Tox | Tox | 0.70 | 0.87 | Tox | Tox | 0.51 | 0.64 | Tox | Tox |
| | | Rolitetracycline | 0.98 | 0.95 | Tox | Tox | 0.71 | 0.74 | Tox | Tox | 0.54 | 0.91 | Tox | Tox |
| | tRNA synthetase | Glycine hydroxamate | 1.36 | Tox | Tox | Tox | 1.06 | 0.47 | Tox | Tox | 1.73 | Tox | Tox | Tox |
| | | DL-Methionine hydroxamate | 1.15 | 1.19 | 1.02 | 0.91 | 0.84 | 0.95 | 2.26 | 3.51 | 0.98 | 1.23 | 1.51 | 1.54 |
| | | L-Aspartic-β-hydroxamate | 1.00 | 1.07 | 0.99 | 0.82 | 0.85 | 0.88 | 0.86 | 1.04 | 0.66 | 0.73 | 0.79 | 1.96 |
| | | L-Glutamic-g-hydroxamate | 1.14 | 1.16 | 0.97 | 1.01 | 0.87 | 0.90 | 0.92 | 0.96 | 0.75 | 0.80 | 0.69 | 0.74 |
| | | D,L-Serine hydroxamate | 0.98 | 0.94 | 1.13 | Tox | 0.77 | 0.78 | 1.03 | 3.47 | 0.62 | 0.66 | 1.18 | Tox |
| Respiration | Ionophore | Gallic acid | 1.01 | 0.98 | 1.16 | Tox | 0.78 | 1.50 | 1.51 | Tox | 0.77 | 0.64 | 1.11 | Tox |
| | | 3,5-Dinitro-benzene | 0.97 | 0.98 | Tox | Tox | 0.85 | 1.00 | 0.32 | Tox | 1.04 | 0.95 | Tox | Tox |
| | | FCCP | 0.96 | 0.78 | 0.77 | 1.00 | 0.53 | 0.43 | 0.67 | 0.60 | 0.64 | 0.48 | 0.48 | 1.04 |
| | | Sodium caprylate | 0.70 | 0.66 | 0.48 | Tox | 0.41 | 0.43 | 0.42 | Tox | 0.34 | 0.38 | 0.57 | Tox |
| | | Cimamic acid | 0.85 | 0.74 | 0.87 | Tox | 0.70 | 0.79 | 1.11 | Tox | 0.53 | 0.54 | 1.11 | Tox |
| | | 2,4-Dintrophenol | 0.87 | 0.83 | 1.10 | Tox | 0.76 | 0.64 | 0.99 | Tox | 0.50 | 0.49 | 1.14 | Tox |
| | | Sorbic acid | 1.01 | 1.11 | 1.10 | 1.02 | 0.94 | 1.05 | 1.03 | 0.91 | 0.79 | 0.97 | 1.12 | 1.02 |
| | | Pentachloro-phenol | 1.01 | 0.95 | 0.95 | 0.70 | 0.44 | 0.36 | 0.29 | 0.57 | 0.36 | 0.34 | 0.34 | 0.68 |
| | | 18-Crown-6 ether | 0.94 | 0.85 | 0.78 | 0.80 | 0.81 | 0.80 | 0.71 | 0.93 | 0.61 | 0.62 | 0.68 | 0.79 |
| | | CCCP | 0.76 | 0.53 | 1.01 | Tox | 0.44 | 0.34 | 0.39 | Tox | 0.75 | 0.76 | 1.35 | Tox |
| | Other | Iodonitro Tetrazolium Violet | 1.02 | #### | 0.06 | 0.33 | 0.84 | #### | 0.09 | 0.17 | 0.74 | #### | 0.36 | 0.58 |
| | | Oxycarboxin | 0.97 | 0.62 | Tox | Tox | 1.04 | 0.83 | Tox | Tox | 1.35 | 1.52 | Tox | Tox |
| | | Ruthenium red | 0.73 | 0.60 | 0.51 | 0.50 | 0.52 | 0.47 | 0.37 | 0.30 | 0.45 | 0.38 | 0.33 | 0.29 |
| | Uncoupler | Crystal violet | 1.00 | 1.06 | 1.08 | 1.00 | 1.02 | 1.36 | 1.16 | 1.13 | 0.97 | 1.03 | 1.42 | 1.47 |
| | | Menadione | 0.34 | 0.49 | 0.63 | 0.50 | 0.20 | 0.18 | 0.22 | 0.18 | 0.13 | 0.24 | 0.33 | 0.41 |
| | | Sodium azide | 0.99 | Tox | Tox | Tox | 0.88 | Tox | Tox | Tox | 0.94 | Tox | Tox | Tox |
| | | Tetrazolium violet | 0.91 | 0.77 | Tox | Tox | 0.83 | 0.75 | Tox | Tox | 0.46 | 0.78 | Tox | Tox |
| Wall | β-lactam | Phenethicillin | 1.33 | 1.26 | Tox | Tox | 1.40 | Tox | Tox | Tox | 0.83 | 0.58 | Tox | Tox |
| | | Cloxacillin | 0.96 | 1.37 | 1.84 | Tox | 0.81 | 1.24 | Tox | Tox | 0.61 | 0.83 | 0.70 | Tox |
| | | Piperacillin | 1.10 | 1.07 | 1.02 | 1.03 | 0.77 | 0.79 | 0.76 | 0.73 | 0.68 | 0.61 | 0.60 | 0.57 |
| | | Nafcillin | 0.94 | 1.08 | 0.57 | Tox | 0.81 | 1.15 | Tox | Tox | 0.62 | 0.69 | 0.61 | Tox |
| | | Penicillin G | 1.04 | 0.96 | 1.47 | Tox | 0.91 | 1.19 | 1.99 | Tox | 0.96 | 0.79 | 1.07 | Tox |
| | | Aziocillin | 0.97 | 1.05 | 1.08 | Tox | 0.94 | 0.90 | 0.97 | Tox | 0.78 | 0.70 | 0.61 | Tox |
| | | Ampicillin | 1.01 | 0.95 | 0.94 | 1.09 | 0.93 | 0.85 | 0.82 | 0.88 | 0.92 | 0.82 | 0.78 | 0.71 |
| | | Amoxicillin | 1.04 | 0.93 | 0.86 | Tox | 0.91 | 0.89 | 1.13 | Tox | 0.84 | 0.61 | 0.53 | Tox |
| | | Carbenicillin | 0.85 | 0.90 | 0.84 | 0.92 | 0.87 | 0.98 | 0.93 | 0.93 | 0.68 | 0.76 | 0.76 | 0.89 |
| | | Carbenicillin | 1.04 | 1.12 | 1.83 | 0.62 | 0.88 | 0.84 | Tox | Tox | 0.75 | 0.72 | 1.21 | 0.95 |
| | | Oxacillin | 1.05 | 1.63 | Tox | Tox | 1.00 | 1.23 | Tox | Tox | 0.74 | 0.68 | 0.86 | Tox |
| | Cephalosporin | Cefamandole nafate | 1.15 | 1.28 | 1.30 | 1.68 | 0.95 | 0.98 | 0.88 | 1.64 | 0.91 | 0.90 | 0.92 | 1.14 |
| | | Cefsulodin | 1.31 | 1.10 | 1.35 | 1.31 | 0.97 | 0.94 | 1.10 | 1.31 | 1.02 | 0.80 | 0.96 | 1.02 |
| | | Cefoxitin | 1.11 | 1.09 | 1.07 | 1.15 | 0.99 | 0.90 | 0.87 | 1.08 | 0.88 | 0.69 | 0.62 | 0.66 |
| | | Cefuroxime | 1.17 | 1.53 | Tox | Tox | 0.91 | 1.29 | Tox | Tox | 0.97 | 0.87 | Tox | Tox |
| | | Cefoperazone | 1.31 | 1.48 | 1.06 | Tox | 0.89 | 1.02 | 1.54 | 0.93 | 1.01 | 0.98 | 1.15 | Tox |
| | | Cephalothin | 0.90 | 0.91 | 1.89 | Tox | 0.92 | 0.87 | 1.94 | Tox | 0.89 | 0.76 | 1.32 | Tox |
| | | Moxalactam | 1.11 | 1.17 | 1.14 | 1.13 | 0.97 | 0.91 | 0.90 | 0.89 | 0.86 | 0.92 | 0.94 | 0.90 |
| | | Ceftriaxone | 0.93 | 0.95 | 0.65 | 1.12 | 0.90 | 0.84 | 0.57 | 0.05 | 0.84 | 0.63 | 0.73 | 0.68 |
| | | Cefazolin | 1.03 | 0.94 | 0.56 | Tox | 0.88 | 0.80 | 0.45 | Tox | 0.85 | 0.61 | 0.38 | Tox |
| | | Cefmetazole | 1.06 | 1.12 | Tox | Tox | 1.04 | 1.12 | Tox | Tox | 0.73 | 0.70 | Tox | Tox |
| | | Cefotaxime | 1.12 | 1.28 | Tox | Tox | 1.42 | Tox | Tox | Tox | 0.93 | 1.25 | Tox | Tox |

TABLE 5-continued

|  |  |  |  |  |  |  |  |  |  |  |  |  |  |
|---|---|---|---|---|---|---|---|---|---|---|---|---|---|
|  | Other | Aztreonam | 0.94 | 0.97 | 1.21 | 1.03 | 0.38 | 0.43 | 0.49 | 0.54 | 0.44 | 0.41 | 0.53 | 0.56 |
|  |  | Phosphomycin | 1.16 | 1.01 | 0.99 | 0.95 | 0.94 | 0.91 | 0.86 | 0.95 | 0.79 | 0.77 | 0.76 | 0.72 |
|  | Peptidoglycan synthesis | D-Serine | 1.75 | 1.58 | 1.41 | Tox | 0.99 | 1.29 | 1.01 | Tox | 1.15 | 1.24 | 1.52 | Tox |
|  |  | D-Cycloserine | 1.13 | 2.02 | Tox | Tox | 1.16 | 2.08 | Tox | Tox | 1.14 | 1.58 | Tox | Tox |
|  |  | Glycine | 0.94 | 0.96 | 0.91 | 0.99 | 0.80 | 0.81 | 0.81 | 0.92 | 0.55 | 0.59 | 0.61 | 0.76 |
|  | Polymyxin | Polymyxin B | 1.13 | Tox | Tox | Tox | 0.97 | Tox | Tox | Tox | 0.82 | Tox | Tox | Tox |
|  |  | Colistin | 0.95 | 0.98 | Tox | Tox | 0.82 | 0.87 | Tox | Tox | 0.63 | 0.45 | Tox | Tox |
|  |  | Polymyxin B | 0.90 | 0.91 | Tox | Tox | 0.75 | 0.77 | Tox | Tox | 0.56 | 0.61 | Tox | Tox |

|  |  |  | Gold (μM) | | | | | | | | | | | |
|---|---|---|---|---|---|---|---|---|---|---|---|---|---|
| Drug Class | | Chemical | 5 | | | | 25 | | | | 50 | | | |
| Chelator | Carboxylic acid | EGTA | 1.05 | 0.88 | 0.94 | 0.92 | 1.07 | 1.00 | 0.95 | 0.97 | 1.02 | 1.13 | 1.04 | 1.11 |
|  |  | Fusaric acid | 1.07 | 1.01 | Tox | Tox | 0.95 | 1.06 | Tox | Tox | 0.79 | 0.81 | Tox | Tox |
|  |  | EDTA | 1.07 | 1.11 | 1.02 | 1.16 | 0.98 | 0.94 | 0.93 | 0.74 | 0.80 | 0.88 | 0.76 | 0.34 |
|  | Hydroxyquinoline | 5,7-Dichloro-8-hydroxyquinoline | 1.04 | 1.08 | 1.28 | 1.14 | 1.04 | 1.01 | 0.89 | 0.91 | 0.98 | 0.93 | 0.99 | 0.78 |
|  |  | 8-Hydroxyquinoline | 1.02 | 1.07 | 1.26 | Tox | 1.03 | 0.99 | 1.11 | Tox | 0.75 | 0.73 | 1.06 | Tox |
|  |  | 5,7-Dichloro-8-hydroxyquinaldine | 1.07 | 1.24 | 1.02 | 1.10 | 1.02 | 1.05 | 0.84 | 0.83 | 0.84 | 0.76 | 0.71 | 0.86 |
|  |  | 5-Chloro-7-iodo-8-hydroxyquinoline | 0.90 | 0.86 | 0.93 | 1.18 | 0.99 | 0.90 | 0.89 | 0.84 | 0.72 | 0.76 | 0.71 | 0.89 |
|  | Other | 2,2'-Dipyridyl | 1.15 | Tox | Tox | Tox | 1.09 | Tox | Tox | Tox | 0.72 | Tox | Tox | Tox |
|  |  | 1,10-Phenanthroline | 1.01 | 0.95 | 1.05 | Tox | 1.05 | 0.88 | 1.15 | Tox | 0.90 | 0.72 | 0.80 | Tox |
|  |  | Sodium pyrophosphate decahydrate | 1.05 | 1.02 | 1.04 | 1.28 | 1.06 | 0.95 | 0.96 | 0.95 | 0.87 | 0.81 | 0.83 | 0.59 |
| DNA & RNA | DNA Alkylation | 5-Azacytidine | 1.02 | 1.04 | 0.85 | 0.96 | 0.97 | 1.03 | 1.02 | 1.01 | 0.92 | 0.90 | 0.79 | 0.82 |
|  |  | Chlorambucil | 0.95 | 1.11 | 1.09 | 1.11 | 1.03 | 0.98 | 1.01 | 0.96 | 0.92 | 1.15 | 0.97 | 0.98 |
|  | Fluoroquinolone | Enoxacin | 1.04 | 0.92 | Tox | Tox | 1.03 | 1.20 | Tox | Tox | 1.07 | 1.21 | Tox | Tox |
|  |  | Ciprofloxacin | 1.01 | 1.07 | 1.04 | Tox | 1.09 | 1.13 | 1.26 | Tox | 0.99 | 1.10 | 2.09 | Tox |
|  |  | Lomefloxacin | 1.03 | 1.07 | 0.91 | Tox | 1.03 | 1.04 | 1.36 | Tox | 1.04 | 1.06 | 0.64 | Tox |
|  |  | Norfloxacin | 0.92 | 0.94 | 1.13 | Tox | 1.00 | 0.99 | 1.03 | Tox | 0.80 | 0.78 | 0.74 | Tox |
|  |  | Ofloxacin | 1.01 | 0.98 | 0.95 | Tox | 1.01 | 0.99 | 0.96 | Tox | 1.05 | 1.04 | 1.13 | Tox |
|  | Intercalator | 2-Phenylphenol | 1.03 | 1.13 | 2.51 | Tox | 1.17 | 1.15 | 0.67 | Tox | 1.08 | 1.15 | 1.51 | Tox |
|  |  | Umbelliferone | 1.02 | 0.85 | 1.44 | 1.15 | 0.95 | 0.96 | 1.41 | 1.09 | 0.90 | 0.90 | 1.46 | 1.26 |
|  |  | Coumarin | 1.10 | 1.09 | 1.23 | Tox | 1.02 | 0.98 | 0.91 | Tox | 0.91 | 0.83 | 0.74 | Tox |
|  |  | Proflavine | 0.97 | 1.02 | 1.04 | 1.11 | 1.09 | 1.10 | 1.05 | 0.90 | 0.95 | 1.03 | 0.97 | 0.71 |
|  |  | 4-Hydroxy-coumarin | 1.01 | 1.14 | 1.10 | Tox | 1.08 | 1.11 | 1.13 | Tox | 1.03 | 1.02 | 0.83 | Tox |
|  |  | Novobiocin | 0.90 | 0.85 | 0.98 | 1.11 | 0.69 | 0.87 | 0.93 | 1.15 | 0.13 | 0.07 | 1.09 | 1.35 |
|  |  | 9-Aminoacridine | 0.97 | 0.98 | 0.99 | 1.05 | 1.00 | 1.03 | 0.98 | 0.83 | 0.96 | 0.83 | 0.97 | 0.87 |
|  |  | Acriflavine | 0.92 | 0.94 | 0.94 | 1.02 | 0.96 | 1.04 | 0.96 | 0.87 | 0.86 | 1.00 | 0.96 | 0.84 |
|  | Nitrofuran analog | Furaltadone | 1.04 | 1.13 | 1.49 | Tox | 1.03 | 1.04 | 1.64 | Tox | 1.02 | 0.98 | 1.99 | Tox |
|  |  | Nitrofurantoin | 1.02 | 1.07 | 1.13 | Tox | 1.07 | 1.06 | 1.05 | Tox | 0.98 | 1.03 | 1.04 | Tox |
|  |  | 5-nitro-2-furaldehyde semicarbazone | 1.01 | 1.04 | Tox | Tox | 0.93 | 0.99 | Tox | Tox | 0.87 | 0.98 | Tox | Tox |
|  | Other | Hydroxylamine | 1.06 | 0.99 | 1.05 | 1.20 | 1.20 | 1.10 | 1.12 | 1.17 | 1.17 | 1.12 | 1.15 | 1.23 |
|  |  | Hexammine cobalt (III) chloride | 1.09 | 1.23 | 1.12 | 1.10 | 1.09 | 1.15 | 1.08 | 1.25 | 1.15 | 1.23 | 1.25 | 1.62 |
|  |  | Disulphiram | 0.01 | 0.01 | Tox | Tox | 0.18 | 0.08 | Tox | Tox | 0.27 | 0.02 | Tox | Tox |
|  |  | Myricetin | 1.11 | 0.96 | 1.46 | 1.09 | 1.02 | 1.00 | 1.30 | 1.36 | 1.02 | 1.05 | 1.46 | 1.32 |
|  | Purine analog | 6-Mercapto-purine | 1.05 | 1.13 | 1.07 | 1.15 | 0.85 | 1.03 | 1.17 | 1.27 | 0.19 | 0.88 | 1.52 | 1.33 |
|  |  | Azathioprine | 1.03 | 0.99 | 1.37 | 1.23 | 0.94 | 0.96 | 1.07 | 1.08 | 0.87 | 0.85 | 0.97 | 1.10 |
|  | Pyrimidine analog | 5-fluoro-5'-deoxyuridine | 1.05 | 1.08 | 1.04 | 1.04 | 1.17 | 1.13 | 1.22 | 1.24 | 1.00 | 1.00 | 0.98 | 1.04 |
|  |  | Trifluorothymidine | 1.00 | 0.99 | 1.00 | 1.01 | 0.97 | 1.05 | 1.06 | 1.07 | 0.82 | 0.92 | 0.88 | 0.92 |
|  |  | Cytosine-1-β-D-arabinofuranoside | 1.08 | 1.06 | 1.04 | 1.18 | 1.01 | 1.04 | 0.95 | 0.88 | 1.00 | 1.07 | 0.97 | 0.98 |
|  |  | 5-Fluorouracil | 1.17 | 1.30 | Tox | Tox | 0.97 | 1.13 | Tox | Tox | 0.91 | 1.11 | Tox | Tox |
|  |  | 5-Fluoroorotic acid | 1.09 | 1.04 | 0.97 | 0.97 | 1.06 | 1.02 | 0.99 | 0.98 | 1.08 | 0.99 | 0.91 | 0.96 |
|  | Quinolone | Cinoxacin | 0.95 | 0.89 | Tox | Tox | 0.96 | 0.98 | Tox | Tox | 0.95 | 0.93 | Tox | Tox |
|  |  | Pipemidic Acid | 0.96 | 1.04 | 0.96 | 0.98 | 0.97 | 1.04 | 1.09 | 1.01 | 0.87 | 0.92 | 0.90 | 0.93 |
|  |  | Nalidixic Acid | 1.00 | 0.93 | Tox | Tox | 1.02 | 0.98 | Tox | Tox | 0.92 | 0.63 | Tox | Tox |
|  |  | Oxolinic acid | 1.07 | 1.05 | 1.15 | 1.04 | 1.05 | 1.13 | 1.10 | 0.99 | 0.93 | 0.97 | 1.01 | 0.82 |
| Folate | Other | 2,4-Diamino-6,7-diisopropylpteridine | 1.02 | 1.05 | 1.23 | Tox | 1.04 | 0.91 | 1.00 | Tox | 0.95 | 0.90 | 1.20 | Tox |
|  |  | Hydroxyurea | 1.51 | 1.23 | 0.79 | Tox | 1.19 | 1.04 | 0.79 | Tox | 1.19 | 1.24 | 1.21 | Tox |
|  |  | Trimethoprim | 1.01 | 0.84 | Tox | Tox | 0.98 | 0.94 | Tox | Tox | 0.77 | 0.77 | Tox | Tox |
|  | Sulfonamide | Sulfanilamide | 0.90 | 0.99 | 0.94 | 0.82 | 0.99 | 0.98 | 0.97 | 1.00 | 0.64 | 0.77 | 0.74 | 0.59 |
|  |  | Sulfamethoxazole | 1.03 | 1.11 | 1.12 | 1.06 | 1.05 | 1.08 | 1.11 | 1.02 | 1.06 | 1.08 | 1.10 | 1.10 |
|  |  | Sulfamethazine | 0.97 | 0.95 | 1.01 | 0.96 | 0.96 | 0.95 | 0.96 | 0.95 | 1.00 | 1.03 | 0.95 | 1.03 |
|  |  | Sulfathiazole | 1.03 | 1.10 | 1.07 | 1.14 | 1.02 | 1.05 | 1.06 | 1.07 | 1.02 | 1.11 | 1.07 | 1.05 |
|  |  | Sulfadiazine | 1.02 | 1.04 | 1.03 | 1.09 | 0.98 | 1.02 | 0.99 | 0.97 | 0.97 | 1.05 | 1.04 | 1.11 |
|  |  | Sulfachloro-pyridazine | 1.03 | 1.04 | 1.53 | 1.02 | 0.90 | 1.02 | 1.14 | 0.93 | 0.82 | 0.91 | 1.04 | 0.77 |
|  |  | Sulfisoxazole | 0.94 | 1.04 | 1.14 | 1.35 | 1.03 | 1.01 | 1.07 | 1.05 | 0.79 | 0.77 | 0.80 | 1.04 |
|  |  | Sulfamono-methoxine | 1.02 | 1.00 | 1.09 | 1.56 | 0.87 | 0.84 | 0.91 | 1.12 | 0.83 | 0.78 | 0.85 | 1.01 |

TABLE 5-continued

| | | | 1 | 2 | 3 | 4 | 5 | 6 | 7 | 8 | 9 | 10 | 11 | 12 |
|---|---|---|---|---|---|---|---|---|---|---|---|---|---|---|
| Membrane | Cationic detergent | Methyltrioctyl NH4+ Br− | 1.06 | 1.05 | 1.00 | Tox | 1.14 | 0.98 | 0.37 | Tox | 0.96 | 1.01 | 0.91 | Tox |
| | | Poly-L-lysine | 1.07 | 0.98 | Tox | Tox | 1.08 | 1.06 | Tox | Tox | 0.93 | 0.88 | Tox | Tox |
| | | Domiphen bromide | 0.98 | 0.98 | 0.96 | Tox | 0.96 | 0.91 | 0.71 | Tox | 0.87 | 0.93 | 0.39 | Tox |
| | | Cetylpyridinium chloride | 1.11 | 1.06 | 0.61 | Tox | 1.03 | 0.98 | 0.58 | Tox | 0.99 | 0.86 | 0.58 | Tox |
| | | Dodecyltrimethyl NH$_4^+$ Br$^-$ | 0.96 | 1.00 | 0.95 | Tox | 0.96 | 0.94 | 1.11 | Tox | 1.02 | 1.14 | 1.05 | Tox |
| | | Benzethonium chloride | 0.98 | 1.02 | Tox | Tox | 1.00 | 1.05 | Tox | Tox | 1.02 | 0.93 | Tox | Tox |
| | Electron transport | Chlorhexidine | 1.02 | 1.03 | 0.98 | 0.19 | 1.02 | 1.04 | 0.99 | 0.78 | 0.94 | 0.96 | 0.93 | 1.02 |
| | | Hexa-chlorophene | 1.09 | 1.05 | 1.06 | 1.01 | 1.04 | 1.05 | 1.12 | 1.09 | 1.00 | 1.07 | 1.06 | 1.06 |
| | | Alexidine | 0.91 | 1.09 | Tox | Tox | 1.01 | 0.96 | Tox | Tox | 0.81 | 0.81 | Tox | Tox |
| | Guanidine | Dodine | 1.01 | 1.03 | 0.91 | Tox | 1.05 | 1.01 | 1.02 | Tox | 0.99 | 0.96 | 0.46 | Tox |
| | | Guanidine hydrochloride | 0.98 | 1.01 | 1.03 | Tox | 0.98 | 0.96 | 1.04 | Tox | 0.72 | 0.65 | 0.33 | Tox |
| | Other | Protamine sulfate | 1.01 | 0.96 | 0.49 | Tox | 0.99 | 0.94 | 2.22 | Tox | 0.92 | 1.09 | 1.56 | Tox |
| | | 1-Hydroxy-pyridine-2-thione | 0.99 | 1.03 | 1.33 | Tox | 1.04 | 1.06 | 0.66 | Tox | 0.92 | 0.89 | 0.23 | Tox |
| | | Amitriptyline | 0.98 | 0.95 | Tox | Tox | 1.18 | 1.12 | Tox | Tox | 0.84 | 0.99 | Tox | Tox |
| | | Niaproof | 1.32 | 1.13 | 1.01 | 1.27 | 1.21 | 1.03 | 1.09 | 1.15 | 1.35 | 1.20 | 0.95 | 1.51 |
| | | Lauryl sulfobetaine | 0.86 | 1.26 | 0.86 | 0.99 | 0.96 | 0.87 | 1.00 | 1.09 | 1.13 | 1.04 | 0.96 | 1.17 |
| | Phenothiazine | Promethazine | 0.95 | 1.07 | 0.67 | Tox | 1.00 | 1.05 | 0.80 | Tox | 1.03 | 1.15 | 0.54 | Tox |
| | | Chlorpromazine | 1.40 | 1.08 | 1.09 | Tox | 1.04 | 0.92 | 0.71 | Tox | 0.95 | 0.75 | 0.04 | Tox |
| | | Thioridazine | 0.97 | 1.16 | 0.79 | Tox | 1.04 | 0.95 | 0.64 | Tox | 0.80 | 0.72 | 0.59 | Tox |
| | | Trifluoperazine | 1.16 | 1.11 | 1.01 | 0.96 | 1.01 | 0.93 | 0.96 | 0.94 | 1.18 | 0.91 | 0.87 | 0.57 |
| Other biocide | Anti-capsule | Sodium salicylate | 1.98 | Tox | Tox | Tox | 1.25 | Tox | Tox | Tox | 1.47 | Tox | Tox | Tox |
| | | Thiosalicylic acid | 1.61 | 1.09 | 1.12 | 1.37 | 1.24 | 0.96 | 0.64 | 0.51 | 1.10 | 0.11 | 0.07 | 0.08 |
| | | Ketoprofen | 1.06 | 1.16 | 1.04 | Tox | 1.18 | 1.05 | 0.89 | Tox | 0.97 | 0.76 | 0.78 | Tox |
| | Acetylcholine antagonist | Pridinol | 1.08 | 1.15 | 0.83 | Tox | 0.99 | 0.96 | Tox | Tox | 0.78 | 0.97 | Tox | Tox |
| | | Atropine | 1.02 | 1.06 | Tox | Tox | 1.02 | 1.12 | Tox | Tox | 0.91 | 0.83 | Tox | Tox |
| | | Orphenadrine | 1.01 | 1.08 | Tox | Tox | 1.11 | 0.98 | Tox | Tox | 0.92 | 0.82 | Tox | Tox |
| | Glycopeptide | Phleomycin | 0.98 | 1.06 | 1.05 | 1.33 | 1.01 | 1.03 | 0.88 | 0.87 | 0.99 | 0.96 | 0.92 | 1.29 |
| | | Vancomycin | 0.94 | 1.03 | 1.14 | Tox | 0.96 | 0.94 | 0.48 | Tox | 0.91 | 0.73 | 0.06 | Tox |
| | | Bleomycin | 1.08 | 1.08 | 1.09 | 0.95 | 1.00 | 0.96 | 0.91 | Tox | 0.87 | 0.83 | 0.02 | Tox |
| | Fungicide | Nordihydroguaiaretic acid | 0.96 | 0.95 | 1.01 | 0.94 | 0.93 | 0.83 | 0.90 | 0.75 | 0.92 | 0.92 | 0.94 | 0.70 |
| | | Chloroxylenol | 0.95 | 0.34 | Tox | Tox | 1.13 | 1.07 | Tox | Tox | 0.97 | 0.35 | Tox | Tox |
| | Phenylsulfamide | Tolylfluanid | 1.00 | 1.01 | 1.00 | 0.95 | 1.05 | 1.04 | 1.07 | 1.19 | 0.80 | 0.74 | 0.76 | 0.94 |
| | | Dichlofluanid | 1.02 | Tox | 0.95 | 0.65 | 0.91 | Tox | 1.01 | 0.85 | 0.88 | Tox | 0.83 | 0.60 |
| | Ion (K+) blocker | 4-Aminopyridine | 1.62 | 1.41 | 1.09 | 1.03 | 1.18 | 1.10 | 0.94 | 1.00 | 1.20 | 0.96 | 0.93 | 0.78 |
| | | Dequalinium chloride | 0.93 | 1.02 | 0.95 | 0.93 | 1.04 | 1.05 | 1.09 | 0.98 | 1.00 | 0.96 | 0.83 | 0.71 |
| | Ion (Na+) blocker | Procaine | 0.98 | 0.99 | 1.00 | 1.16 | 1.01 | 0.98 | 1.01 | 0.95 | 0.72 | 0.68 | 0.78 | 0.28 |
| | | Lidocaine | 1.10 | 0.92 | 0.91 | Tox | 1.02 | 0.91 | 0.91 | Tox | 0.88 | 0.80 | 0.32 | Tox |
| | Nitroimidazole | Tinidazole | 1.11 | 1.11 | 1.38 | Tox | 1.04 | 1.07 | 0.97 | Tox | 0.95 | 0.99 | 1.04 | Tox |
| | | 2-Nitroimidazole | 1.01 | 0.87 | Tox | Tox | 0.97 | 1.02 | Tox | Tox | 0.87 | 0.86 | Tox | Tox |
| | | Ornidazole | 1.07 | 1.10 | 1.08 | Tox | 1.06 | 1.07 | 1.00 | Tox | 0.95 | 0.75 | 1.71 | Tox |
| | Other | Tannic acid | 0.97 | 1.16 | 1.24 | 1.05 | 0.92 | 1.06 | 1.11 | 1.10 | 1.13 | 1.31 | 1.12 | 1.16 |
| | | Semicarbazide | 1.13 | 1.06 | 1.14 | 1.23 | 1.09 | 1.19 | 1.29 | 1.13 | 0.97 | 1.12 | 1.18 | 1.14 |
| | | Captan | 0.97 | 0.89 | 0.82 | 1.11 | 0.99 | 0.82 | 0.83 | 0.60 | 0.95 | 0.92 | 0.65 | 0.79 |
| | | Ethionamide | 0.99 | 1.05 | 1.09 | 0.98 | 0.97 | 0.83 | 0.84 | 0.75 | 0.87 | 0.86 | 0.79 | 0.74 |
| | | D,L-Propranolol | 1.04 | 1.09 | Tox | Tox | 1.06 | 1.04 | Tox | Tox | 0.77 | 0.69 | Tox | Tox |
| | | Compound 48/80 | 1.49 | 0.98 | 0.97 | Tox | 1.12 | 0.99 | 0.96 | Tox | 1.03 | 0.88 | 0.85 | Tox |
| | | Chelerythrine | 0.99 | 0.96 | 1.16 | 1.16 | 0.98 | 0.95 | 1.00 | 1.11 | 0.91 | 0.85 | 0.68 | 0.93 |
| | | Sanguinarine | 0.91 | 1.21 | Tox | Tox | 1.03 | 0.89 | Tox | Tox | 0.87 | 0.79 | Tox | Tox |
| | | Patulin | 1.02 | Tox | Tox | Tox | 1.12 | Tox | Tox | Tox | 0.74 | Tox | Tox | Tox |
| | Rifamycin | Rifampicin | 1.06 | 1.04 | 1.21 | Tox | 1.02 | 1.00 | 0.93 | Tox | 1.02 | 1.07 | 0.44 | Tox |
| | | Rifamycin SV | 1.00 | 1.05 | 0.74 | 0.95 | 0.97 | 0.99 | 0.68 | 0.88 | 0.94 | 0.95 | 1.00 | 0.77 |
| | Triazole | Guanazole | 1.02 | 1.04 | Tox | Tox | 1.08 | 1.07 | Tox | Tox | 0.84 | 0.93 | Tox | Tox |
| | | 3-Amino-1,2,4-triazole | 1.21 | 1.12 | 1.22 | Tox | 1.06 | 0.93 | 1.25 | Tox | 0.88 | 0.68 | 0.59 | Tox |
| | Oxidizing agent | Diamide | 0.99 | 0.86 | Tox | Tox | 0.98 | 0.89 | Tox | Tox | 0.98 | 0.93 | Tox | Tox |
| | | 1-Chloro-2,4-dinitrobenzene | 1.16 | 1.03 | 0.98 | 0.60 | 1.09 | 0.98 | 1.00 | 1.12 | 0.98 | 0.95 | 0.86 | 0.85 |
| | | D,L-Thioctic Acid | 1.13 | 1.13 | 1.08 | Tox | 1.03 | 1.05 | 1.03 | Tox | 1.36 | 1.55 | 1.06 | Tox |
| | | Lawsone | 1.09 | 1.08 | 1.21 | Tox | 1.15 | 1.16 | 1.31 | Tox | 1.26 | 1.62 | 0.98 | Tox |
| | | Plumbagin | 1.03 | 1.01 | 1.00 | 0.98 | 1.05 | 1.00 | 1.00 | 1.02 | 0.98 | 0.99 | 0.98 | 1.01 |
| | | 3,4-Dimethoxybenzyl alcohol | 1.05 | 1.07 | 0.94 | Tox | 1.04 | 1.03 | 0.89 | Tox | 0.86 | 0.87 | 1.03 | Tox |
| | | Methyl viologen | 0.99 | 1.07 | 0.82 | 0.08 | 1.01 | 1.01 | 0.66 | 0.78 | 1.04 | 0.98 | 0.50 | 0.28 |
| | | Iodoacetate | 0.77 | Tox | Tox | Tox | 1.00 | Tox | Tox | Tox | 0.98 | Tox | Tox | Tox |
| Protein | Aminoglycoside | Dihydro-streptomycin | 1.07 | 1.14 | 1.07 | 0.93 | 1.18 | 1.22 | 1.18 | 1.30 | 1.17 | 1.29 | 1.19 | 1.26 |
| | | Hygromycin B | 1.23 | 0.82 | Tox | Tox | 0.96 | 1.13 | Tox | Tox | 0.97 | 1.27 | Tox | Tox |
| | | Gentamicin | 0.97 | 1.00 | 0.99 | 1.04 | 0.97 | 0.99 | 1.00 | 1.00 | 1.04 | 0.97 | 1.00 | 1.01 |
| | | Sisomicin | 1.01 | 0.99 | 0.98 | 0.90 | 0.99 | 0.98 | 1.00 | 0.97 | 0.94 | 0.97 | 1.03 | |
| | | Neomycin | 1.01 | 1.02 | 1.00 | 1.03 | 0.95 | 0.96 | 0.94 | 1.02 | 1.02 | 1.06 | 1.01 | 1.13 |
| | | Spectinomycin | 0.98 | 1.02 | Tox | Tox | 1.06 | 1.09 | Tox | Tox | 0.98 | 1.20 | Tox | Tox |
| | | Geneticin (G418) | 1.08 | 1.00 | 1.01 | 0.95 | 1.05 | 1.03 | 1.00 | 1.02 | 1.05 | 1.04 | 1.05 | 1.11 |
| | | Tobramycin | 1.07 | 1.05 | 0.99 | 0.96 | 1.01 | 1.10 | 1.01 | 1.01 | 1.00 | 1.04 | 1.07 | 0.97 |
| | | Paromomycin | 1.02 | 1.02 | 0.99 | 1.01 | 0.98 | 1.02 | 1.02 | 1.06 | 0.87 | 0.92 | 1.00 | 1.03 |

TABLE 5-continued

| | | | | | | | | | | | | | | |
|---|---|---|---|---|---|---|---|---|---|---|---|---|---|---|
| | | Amikacin | 1.02 | 1.10 | 1.09 | 1.13 | 1.06 | 1.10 | 1.02 | 0.95 | 0.90 | 1.03 | 1.02 | 1.13 |
| | | Kanamycin | 1.06 | 1.03 | 1.01 | 0.93 | 1.01 | 0.95 | 0.99 | 0.91 | 1.03 | 1.04 | 1.07 | 1.05 |
| | | Apramycin | 1.03 | 1.06 | 1.04 | 1.04 | 1.13 | 1.09 | 1.18 | 1.17 | 0.91 | 0.90 | 0.97 | 0.98 |
| | | Capreomycin | 1.05 | 1.05 | 1.02 | 1.03 | 1.03 | 1.01 | 0.97 | 1.06 | 1.00 | 0.98 | 1.01 | 1.14 |
| | | Streptomycin | 0.94 | 0.88 | Tox | Tox | 1.01 | 0.58 | Tox | Tox | 0.87 | 1.10 | Tox | Tox |
| | Macrolide | Josamycin | 1.04 | 0.96 | 1.02 | 1.82 | 1.13 | 1.08 | 1.00 | 1.09 | 1.00 | 0.79 | 0.70 | 0.78 |
| | | Spiramycin | 1.03 | 1.00 | Tox | Tox | 1.02 | 0.67 | Tox | Tox | 0.84 | 0.33 | Tox | Tox |
| | | Erythromycin | 0.98 | 1.06 | 0.99 | 0.82 | 0.98 | 0.97 | 0.88 | 0.51 | 0.99 | 0.91 | 0.80 | 0.22 |
| | | Oleandomycin | 1.01 | 1.02 | 0.98 | 0.72 | 0.96 | 0.95 | 0.88 | 0.47 | 0.87 | 0.80 | 0.85 | 0.17 |
| | | Tylosin | 1.00 | 0.97 | 0.86 | 0.73 | 0.99 | 0.95 | 0.35 | 0.30 | 0.91 | 0.74 | 0.08 | 0.04 |
| | | Troleandomycin | 0.97 | 0.89 | 0.69 | 0.11 | 0.91 | 0.66 | 0.76 | 0.40 | 0.61 | 0.29 | 0.05 | 0.07 |
| | Other | PMSF | 1.07 | 0.96 | 0.93 | 0.74 | 1.03 | 1.05 | 1.11 | 0.85 | 1.07 | 1.16 | 1.21 | 2.21 |
| | | Benserazide | 1.07 | 1.13 | 1.18 | 1.13 | 1.03 | 1.18 | 1.15 | 1.22 | 0.89 | 0.98 | 0.61 | 0.78 |
| | | B-Chloro-L-alanine HCl | 1.01 | 1.16 | 1.28 | 1.30 | 1.01 | 1.09 | 1.28 | 1.31 | 0.93 | 1.06 | 1.12 | 1.20 |
| | | Lincomycin | 1.06 | 1.11 | 1.13 | Tox | 1.05 | 1.00 | 1.07 | Tox | 1.08 | 1.05 | 0.98 | Tox |
| | Protein synthesis | Fusidic acid | 1.05 | 0.95 | Tox | 0.77 | 0.74 | 0.48 | Tox | 0.63 | 0.73 | 0.70 | Tox | 0.62 |
| | | Blasticidin S | 1.05 | 0.95 | 0.97 | Tox | 1.06 | 1.08 | 1.11 | Tox | 1.09 | 1.06 | 1.11 | Tox |
| | | Chloramphenicol | 0.97 | 0.71 | Tox | Tox | 0.99 | 0.88 | Tox | Tox | 0.88 | 0.74 | Tox | Tox |
| | | Puromycin | 1.04 | 1.08 | 1.01 | Tox | 0.96 | 0.95 | 0.73 | Tox | 0.99 | 0.95 | 0.59 | Tox |
| | | Chloramphenicol | 0.97 | 0.91 | Tox | Tox | 1.04 | 0.97 | Tox | Tox | 0.84 | 0.74 | Tox | Tox |
| | | Thiamphenicol | 0.93 | 1.37 | Tox | Tox | 0.92 | 0.65 | Tox | Tox | 0.64 | 0.53 | Tox | Tox |
| | Tetracycline | Doxycycline | 1.09 | 1.28 | Tox | Tox | 1.03 | 0.80 | Tox | Tox | 0.94 | 0.64 | Tox | Tox |
| | | Chlortetracycline | 1.04 | 1.00 | Tox | Tox | 0.83 | 0.82 | Tox | Tox | 1.11 | 0.85 | Tox | Tox |
| | | Oxytetracycline | 1.08 | 1.05 | 1.12 | 1.13 | 1.04 | 1.03 | 1.04 | 1.08 | 0.91 | 0.90 | 0.90 | 0.91 |
| | | Tetracycline | 1.04 | 1.03 | 1.13 | 1.03 | 1.03 | 1.07 | 1.17 | 1.04 | 0.95 | 0.98 | 0.96 | 0.91 |
| | | Demeclocycline | 1.03 | 1.04 | Tox | Tox | 0.98 | 0.98 | Tox | Tox | 1.04 | 1.01 | Tox | Tox |
| | | Minocycline | 1.09 | 1.04 | 0.81 | Tox | 1.03 | 1.03 | Tox | Tox | 1.04 | 0.93 | Tox | Tox |
| | | Penimepicycline | 1.07 | 1.12 | Tox | Tox | 1.02 | 1.04 | Tox | Tox | 0.90 | 0.80 | Tox | Tox |
| | | Rolitetracycline | 1.10 | 0.99 | Tox | Tox | 0.99 | 0.89 | Tox | Tox | 1.03 | 0.90 | Tox | Tox |
| | tRNA synthetase | Glycine hydroxamate | 1.08 | 0.95 | 1.13 | 1.01 | 1.07 | 1.11 | 1.19 | 1.12 | 1.00 | 1.07 | 1.39 | 1.22 |
| | | DL-Methionine hydroxamate | 1.08 | 1.10 | 1.06 | Tox | 1.03 | 1.04 | 1.08 | Tox | 0.92 | 0.96 | 0.93 | Tox |
| | | L-Aspartic-β-hydroxamate | 1.06 | 1.05 | 1.05 | 1.19 | 1.02 | 1.02 | 1.01 | 1.03 | 1.06 | 1.05 | 1.11 | 1.19 |
| | | L-Glutamic-g-hydroxamate | 1.03 | 1.03 | 1.08 | 1.08 | 1.02 | 1.01 | 1.09 | 1.04 | 1.01 | 1.01 | 1.02 | 1.01 |
| | | D,L-Serine hydroxamate | 1.04 | 0.95 | 1.45 | 0.71 | 1.02 | 1.00 | 1.22 | Tox | 0.96 | 0.94 | 1.00 | Tox |
| Respiration | Ionophore | Gallic acid | 1.04 | 1.09 | 1.00 | Tox | 1.10 | 1.00 | 0.95 | Tox | 0.90 | 0.84 | 0.99 | Tox |
| | | 3,5-Dinitro-benzene | 0.98 | 1.10 | Tox | Tox | 1.02 | 0.97 | Tox | Tox | 0.94 | 0.87 | Tox | Tox |
| | | FCCP | 0.86 | 0.67 | 0.56 | 0.86 | 0.91 | 1.01 | 1.04 | 0.98 | 1.03 | 1.20 | 1.33 | 1.79 |
| | | Sodium caprylate | 1.02 | 1.12 | Tox | Tox | 1.13 | 0.98 | Tox | Tox | 0.92 | 0.79 | Tox | Tox |
| | | Cinamic acid | 1.12 | 1.09 | 1.19 | Tox | 0.99 | 1.11 | 0.95 | Tox | 0.98 | 0.85 | 0.96 | Tox |
| | | 2,4-Dintrophenol | 1.05 | 1.02 | 1.27 | Tox | 1.02 | 0.94 | 1.02 | Tox | 0.85 | 0.74 | 0.61 | Tox |
| | | Sorbic acid | 0.92 | 0.91 | 1.01 | 0.89 | 1.06 | 1.08 | 0.92 | 0.92 | 0.98 | 1.02 | 0.97 | 0.89 |
| | | Pentachloro-phenol | 0.98 | 0.93 | 1.22 | 1.11 | 0.97 | 0.95 | 0.91 | 0.70 | 0.84 | 0.84 | 1.05 | 1.21 |
| | | 18-Crown-6 ether | 1.05 | 1.05 | 0.99 | 1.40 | 0.99 | 1.01 | 0.99 | 1.08 | 0.92 | 0.72 | 0.70 | 0.66 |
| | | CCCP | 0.97 | 1.30 | 1.55 | 0.33 | 1.05 | 1.14 | 1.63 | 0.60 | 0.80 | 0.83 | 1.22 | 0.39 |
| | Other | odonitro Tetrazolium Violet | 0.96 | 0.96 | 0.90 | 0.87 | 0.91 | 0.99 | 0.81 | 0.78 | 1.12 | 1.03 | 0.60 | 0.61 |
| | | Oxycarboxin | 2.58 | Tox | Tox | Tox | 1.29 | Tox | Tox | Tox | 1.67 | Tox | Tox | Tox |
| | | Ruthenium red | 1.04 | 0.94 | 1.05 | 1.06 | 1.03 | 1.02 | 1.14 | 1.07 | 1.08 | 1.05 | 1.13 | 1.09 |
| | Uncoupler | Crystal violet | 1.04 | 1.03 | 1.03 | 1.04 | 1.04 | 1.07 | 1.11 | 1.04 | 1.04 | 1.05 | 0.99 | 1.03 |
| | | Menadione | 1.00 | 1.12 | 0.93 | 1.13 | 0.97 | 1.11 | 0.97 | 1.11 | 0.90 | 1.09 | 1.03 | 1.17 |
| | | Sodium azide | 1.02 | Tox | Tox | Tox | 1.00 | Tox | Tox | Tox | 1.01 | Tox | Tox | Tox |
| | | Tetrazolium violet | #### | 1.41 | Tox | Tox | 1.28 | 0.76 | Tox | Tox | 0.76 | 0.47 | Tox | Tox |
| Wall | β-lactam | Phenethicillin | 0.95 | 0.91 | Tox | Tox | 0.96 | 1.19 | Tox | Tox | 1.06 | 1.24 | Tox | Tox |
| | | Cloxacillin | 1.02 | 1.13 | 1.29 | Tox | 0.99 | 1.01 | 0.93 | Tox | 1.03 | 1.09 | 0.04 | Tox |
| | | Piperacillin | 0.98 | 1.01 | 0.78 | Tox | 1.02 | 1.10 | 1.36 | Tox | 0.81 | 0.91 | 2.22 | Tox |
| | | Nafcillin | 1.03 | 0.99 | 0.83 | 0.62 | 1.01 | 1.01 | 0.97 | Tox | 1.04 | 1.06 | 1.41 | Tox |
| | | Penicillin G | 0.96 | 1.13 | 1.31 | Tox | 1.04 | 1.10 | 0.84 | Tox | 0.88 | 1.06 | 1.01 | Tox |
| | | Aziocillin | 0.92 | 1.01 | 0.94 | 0.64 | 1.05 | 1.09 | 0.89 | 0.64 | 0.94 | 0.93 | 0.93 | 0.47 |
| | | Ampicillin | 0.97 | 0.95 | 0.95 | 1.00 | 1.05 | 1.03 | 1.02 | 1.01 | 0.97 | 0.92 | 0.95 | 0.97 |
| | | Amoxicillin | 1.05 | 1.00 | 0.60 | Tox | 1.03 | 1.02 | 0.74 | Tox | 0.98 | 0.94 | 0.89 | Tox |
| | | Carbenicillin | 0.95 | 0.67 | 0.86 | Tox | 1.07 | 1.04 | 0.74 | Tox | 0.95 | 0.85 | 1.08 | Tox |
| | | Carbenicillin | 1.13 | 1.08 | Tox | Tox | 1.05 | 1.02 | Tox | Tox | 1.09 | 1.05 | Tox | Tox |
| | | Oxacillin | 0.95 | 1.03 | Tox | Tox | 0.88 | 0.85 | 1.19 | Tox | 1.00 | 0.87 | 0.94 | 0.72 |
| | Cephalosporin | Cefamandole nafate | 1.05 | 1.02 | 0.97 | 0.90 | 1.12 | 1.10 | 0.96 | 0.91 | 1.02 | 1.12 | 1.00 | 0.91 |
| | | Cefsulodin | 1.14 | 1.26 | 1.24 | 1.70 | 1.02 | 1.05 | 1.04 | 1.20 | 1.00 | 1.08 | 1.25 | 1.42 |
| | | Cefoxitin | 1.00 | 1.06 | 1.04 | 0.98 | 0.95 | 1.05 | 1.05 | 0.92 | 0.88 | 1.00 | 1.03 | 1.03 |
| | | Cefuroxime | 0.99 | 1.34 | 1.10 | Tox | 1.03 | 0.99 | 0.28 | Tox | 0.97 | 1.10 | 0.94 | Tox |
| | | Cefoperazone | 0.95 | 0.91 | 0.74 | 0.64 | 1.03 | 0.89 | 0.83 | 0.94 | 1.07 | 1.06 | 0.89 | 0.79 |
| | | Cephalothin | 0.96 | 0.98 | Tox | Tox | 1.02 | 1.01 | 0.86 | Tox | 0.94 | 1.01 | 1.01 | Tox |
| | | Moxalactam | 1.05 | 0.99 | 1.02 | 0.98 | 1.01 | 0.91 | 0.97 | 0.95 | 1.06 | 1.00 | 1.03 | 1.13 |
| | | Ceftriaxone | 1.02 | 1.51 | 1.27 | Tox | 1.06 | 0.96 | 0.97 | Tox | 0.98 | 1.30 | 0.49 | Tox |
| | | Cefazolin | 1.07 | 1.09 | 0.61 | Tox | 1.05 | 1.01 | 1.12 | Tox | 1.00 | 1.00 | 1.21 | Tox |
| | | Cefmetazole | 1.01 | 1.05 | 1.36 | Tox | 1.09 | 1.04 | 0.58 | Tox | 0.92 | 0.87 | 1.10 | Tox |
| | | Cefotaxime | 0.63 | Tox | Tox | Tox | 0.89 | Tox | Tox | Tox | 0.68 | Tox | Tox | Tox |

TABLE 5-continued

| | | | | | | | | | | | | | |
|---|---|---|---|---|---|---|---|---|---|---|---|---|---|
| Other | Aztreonam | 1.00 | 0.92 | 0.82 | Tox | 1.01 | 0.90 | 1.02 | Tox | 0.93 | 1.02 | 1.11 | Tox |
| | Phosphomycin | 0.96 | 1.04 | 0.59 | Tox | 0.98 | 0.87 | 0.45 | Tox | 0.94 | 0.58 | 0.01 | Tox |
| Peptidoglycan | D-Serine | 1.08 | 2.68 | 1.49 | Tox | 0.81 | 1.75 | 1.13 | Tox | 0.99 | 1.74 | 0.97 | Tox |
| synthesis | D-Cycloserine | 0.89 | 1.16 | 0.95 | Tox | 1.02 | 1.07 | 1.13 | Tox | 0.93 | 1.08 | 1.43 | Tox |
| | Glycine | 1.01 | 1.04 | 0.97 | 0.91 | 0.99 | 1.00 | 0.96 | 0.95 | 1.03 | 1.05 | 1.00 | 1.05 |
| Polymyxin | Polymyxin B | 1.07 | Tox | Tox | Tox | 1.10 | Tox | Tox | Tox | 1.00 | Tox | Tox | Tox |
| | Colistin | 1.10 | 1.18 | Tox | Tox | 1.05 | 0.95 | Tox | Tox | 1.09 | 0.14 | Tox | Tox |
| | Polymyxin B | 0.97 | 0.96 | 1.01 | Tox | 0.99 | 0.97 | 0.47 | Tox | 0.92 | 0.92 | 0.23 | Tox |

I claim:

1. A method of screening for synergistically effective metal-biocide combinations, the method comprising:
    contacting a microorganism to a test biocide, which is a drug compound or isotope which is not a metal ion, deposited on a solid surface, wherein the microorganism is in a culture medium comprising a soluble Group IB metal;
    culturing the contacted microorganism in the culture medium;
    screening for a synergistically effective combination of the test biocide and the metal, wherein screening comprises measuring relative growth and determining for the metal-biocide combination a coefficient of drug interaction (CDI) of $(A+B)/A \times B$, wherein A is growth in the presence of the culture medium comprising the soluble Group IB metal but lacking the test biocide normalized to growth in LB medium, B is growth in a same culture medium comprising the test biocide but lacking the Group IB metal normalized to growth in LB medium, and $A \times B$ is growth in the culture medium comprising the soluble Group IB metal and the test biocide normalized to growth in LB medium, wherein a combination is synergistically effective against the microorganisms if CDI<0.5; and
    repeating the aforementioned steps with additional test biocides.

2. The method of claim 1, wherein the microorganism is a bacterium.

3. The method of claim 1, wherein the contacted microorganism is cultured in the culture medium for about 12 to about 24 hours.

4. The method of claim 3, wherein the contacted microorganism is cultured in the culture medium for about 16 hours.

5. The method of claim 1, wherein the test biocides each comprise a radioactive isotope, nanomaterial, or plasmid curing agent.

* * * * *